(12) United States Patent
Vester et al.

(10) Patent No.: US 10,239,063 B2
(45) Date of Patent: Mar. 26, 2019

(54) APPLICATION-SPECIFIC SAMPLE PROCESSING BY MODULES SURROUNDING A ROTOR MECHANISM FOR SAMPLE MIXING AND SAMPLE SEPARATION

(71) Applicant: QUANTIFOIL INSTRUMENTS GMBH, Jena (DE)

(72) Inventors: Andreas Vester, Jena (DE); Falko Schulz, Jena (DE)

(73) Assignee: Quantifoil Instruments GmbH, Jena (DE)

( * ) Notice: Subject to any disclaimer, the term of this patent is extended or adjusted under 35 U.S.C. 154(b) by 407 days.

(21) Appl. No.: 14/901,228

(22) PCT Filed: Jun. 27, 2014

(86) PCT No.: PCT/EP2014/063774
§ 371 (c)(1),
(2) Date: Dec. 28, 2015

(87) PCT Pub. No.: WO2014/207243
PCT Pub. Date: Dec. 31, 2014

(65) Prior Publication Data
US 2016/0368003 A1     Dec. 22, 2016

(30) Foreign Application Priority Data

Jun. 28, 2013 (EP) .................................... 13174416
Jun. 28, 2013 (GB) .................................... 1311667.8

(51) Int. Cl.
*B04B 5/04* (2006.01)
*B04B 5/10* (2006.01)
(Continued)

(52) U.S. Cl.
CPC .............. *B04B 5/10* (2013.01); *B04B 5/0421* (2013.01); *B04B 9/08* (2013.01); *B04B 11/04* (2013.01);
(Continued)

(58) Field of Classification Search
CPC  B04B 5/10; B04B 11/04; B04B 13/00; B04B 5/0421; B04B 9/08; G01N 35/04;
(Continued)

(56) References Cited

U.S. PATENT DOCUMENTS 4,990,130 A     2/1991  Prais
5,167,448 A  *  12/1992 Herold .................. B01F 9/0001
                                                        366/213
(Continued)

FOREIGN PATENT DOCUMENTS

GB         2498953 A       8/2013
JP         10277434        10/1998
(Continued)

OTHER PUBLICATIONS

European Patent Office, Communication pursuant to Article 94(3) EPC in European Patent Application No. 14734461.8-1553 (dated Mar. 20, 2017).
(Continued)

*Primary Examiner* — Walter D. Griffin
*Assistant Examiner* — Shuyi S. Liu
(74) *Attorney, Agent, or Firm* — Leydig, Voit & Mayer, Ltd.

(57) ABSTRACT

A sample processing arrangement for processing a fluidic sample, the sample processing arrangement including a sample holder for accommodating the fluidic sample, an apparatus having a rotor mechanism and being configured for selectively operating the sample holder in an orbital motion mode for sample mixing, particularly for shaking, or
(Continued)

in a rotary motion mode for sample separation, particularly for centrifuging, a mounting platform having a central portion on which the apparatus and the sample holder are mounted and having a surrounding portion circumferentially surrounding the central portion, and a plurality of module accommodation positions circumferentially distributed in the surrounding portion to surround the rotor mechanism and the sample holder, wherein each of the module accommodation positions is configured for detachably accommodating a selectable one of a plurality of sample processing modules, each being configured for fulfilling an assigned sample processing task, by accommodating the respective sample processing module in the respective one of the module accommodation positions.

42 Claims, 30 Drawing Sheets

(51) Int. Cl.
    B04B 9/08     (2006.01)
    B04B 11/04    (2006.01)
    B04B 13/00    (2006.01)
    G01N 35/00    (2006.01)
    G01N 35/04    (2006.01)
(52) U.S. Cl.
    CPC ......... *B04B 13/00* (2013.01); *G01N 35/04* (2013.01); *G01N 2035/00326* (2013.01); *G01N 2035/00495* (2013.01); *G01N 2035/00504* (2013.01); *G01N 2035/0439* (2013.01); *G01N 2035/0446* (2013.01); *G01N 2035/0448* (2013.01)
(58) Field of Classification Search
    CPC . G01N 2035/0439; G01N 2035/00495; G01N 2035/00326; G01N 2035/0446; G01N 2035/0448; G01N 2035/00504; B01F 11/0025; B01F 11/0005; B01F 11/00028
    USPC ......... 494/16, 17, 20, 21, 84, 85, 33, 37, 43
    See application file for complete search history.

(56) References Cited

U.S. PATENT DOCUMENTS

| | | | |
|---|---|---|---|
| 6,060,022 A | 5/2000 | Pang et al. | |
| 7,520,660 B2 * | 4/2009 | Schulz | B01F 9/0001 366/217 |
| 9,126,162 B2 | 9/2015 | Simmat et al. | |
| 2002/0052042 A1 * | 5/2002 | Gordon | B04B 5/02 435/287.2 |
| 2003/0032191 A1 * | 2/2003 | Nilson | C01N 35/00029 436/47 |
| 2003/0155312 A1 * | 8/2003 | Ivansons | A61M 1/16 210/787 |
| 2004/0087426 A1 * | 5/2004 | Lattanzi | B04B 5/0421 494/20 |
| 2006/0073584 A1 | 4/2006 | Sasaki et al. | |
| 2007/0036686 A1 | 2/2007 | Hatamian et al. | |
| 2008/0300148 A1 * | 12/2008 | Lee | B01L 3/502738 506/39 |
| 2010/0055766 A1 | 3/2010 | Hwang et al. | |
| 2010/0261595 A1 * | 10/2010 | Schaefer | B04B 7/08 494/20 |
| 2012/0291538 A1 * | 11/2012 | Ludowise | B01L 3/5027 73/149 |
| 2013/0011224 A1 | 1/2013 | Hoyer et al. | |
| 2013/0042704 A1 * | 2/2013 | Van Duyne | B04B 9/08 73/864.91 |
| 2013/0078624 A1 * | 3/2013 | Holmes | C12Q 1/00 435/6.11 |
| 2013/0218352 A1 * | 8/2013 | Iovanni | G05D 7/0617 700/282 |
| 2014/0208813 A1 * | 7/2014 | Reeb | B65F 1/1615 70/277 |

FOREIGN PATENT DOCUMENTS

| | | | |
|---|---|---|---|
| JP | 2007-237036 A | | 9/2007 |
| KR | 803063 | * | 2/2008 |
| WO | WO 2000/060362 A1 | | 10/2000 |
| WO | WO 2011/113858 A1 | | 9/2011 |

OTHER PUBLICATIONS

European Patent Office, International Search Report in International Application No. PCT/EP2014/063774 (dated Oct. 13, 2014).
European Patent Office, Written Opinion in International Application No. PCT/EP2014/063774 (dated Oct. 13, 2014).
International Bureau of WIPO, International Preliminary Report on Patentability in International Application No. PCT/EP2014/063774 (dated Dec. 29, 2015).

* cited by examiner

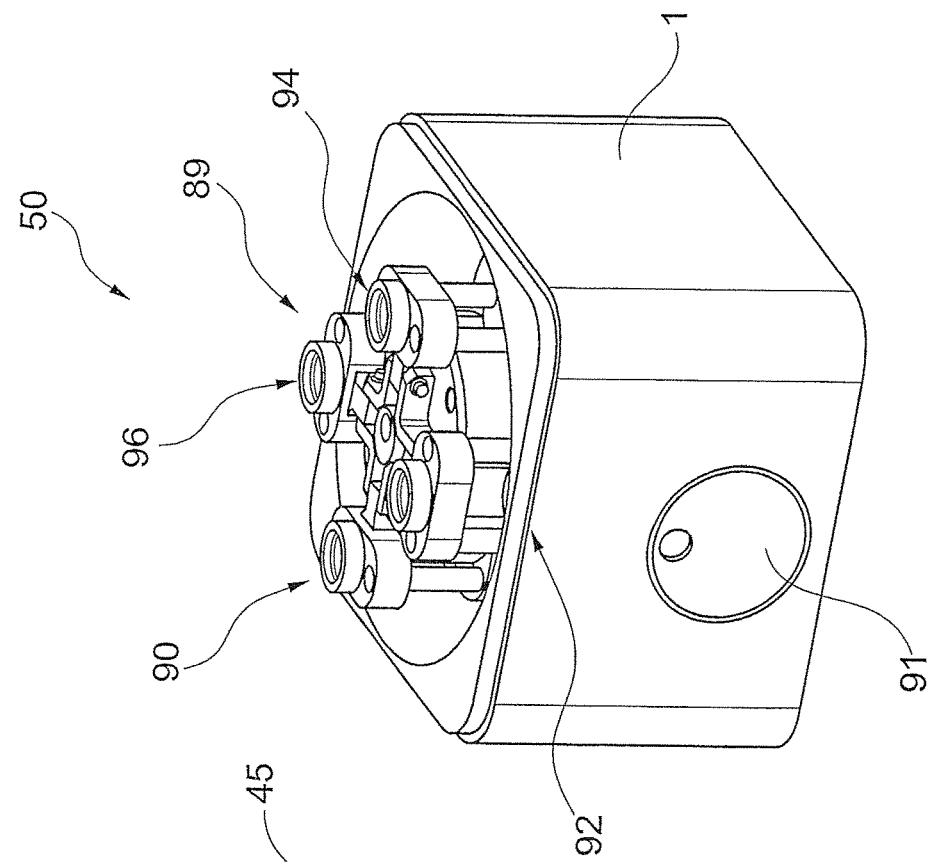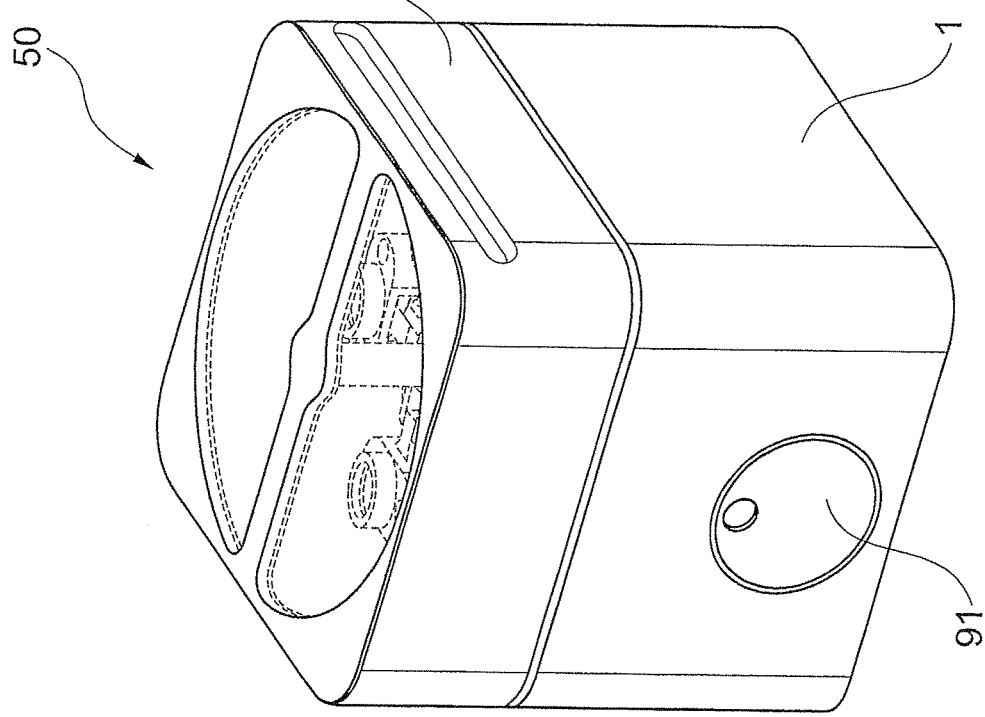

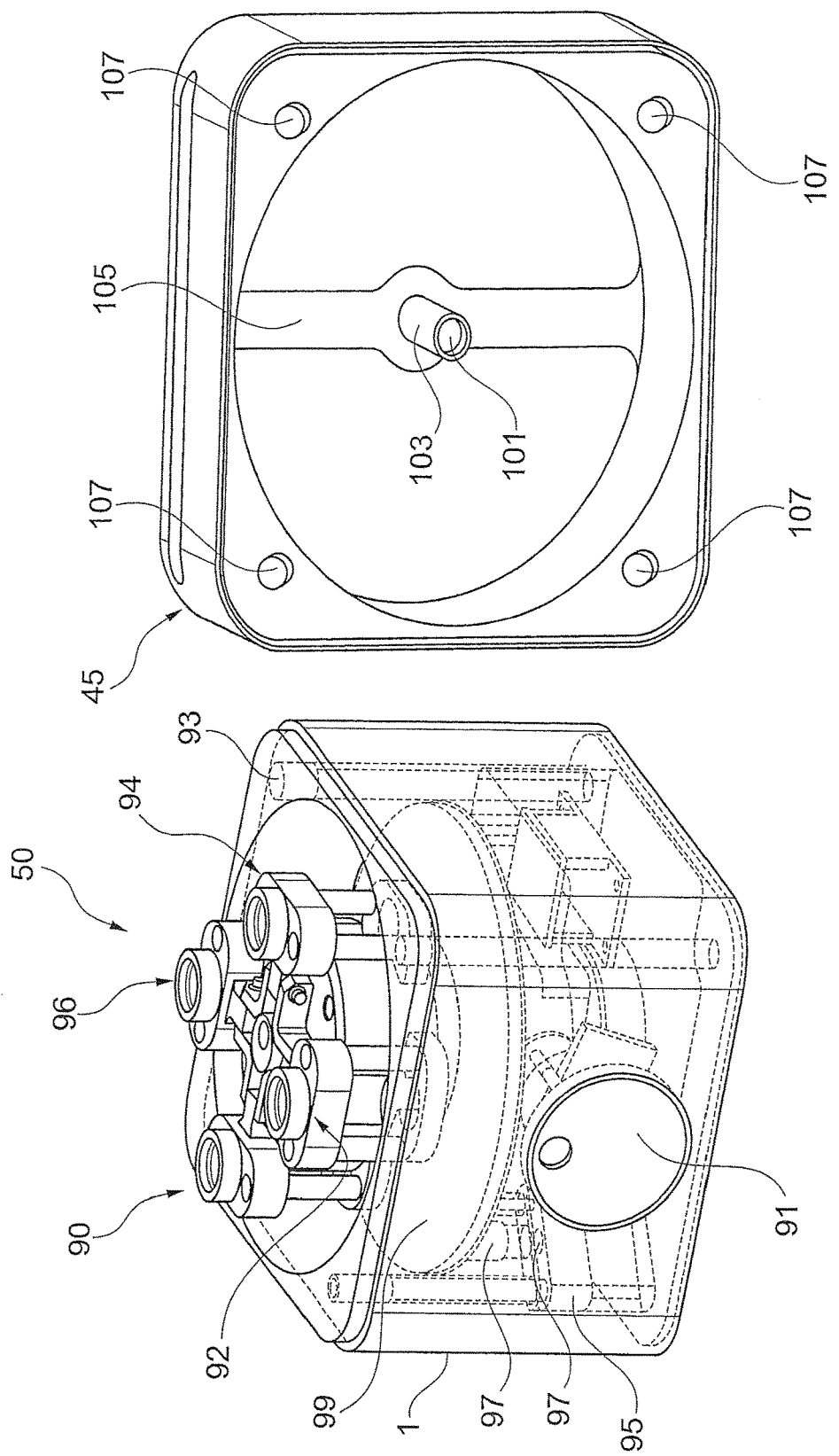

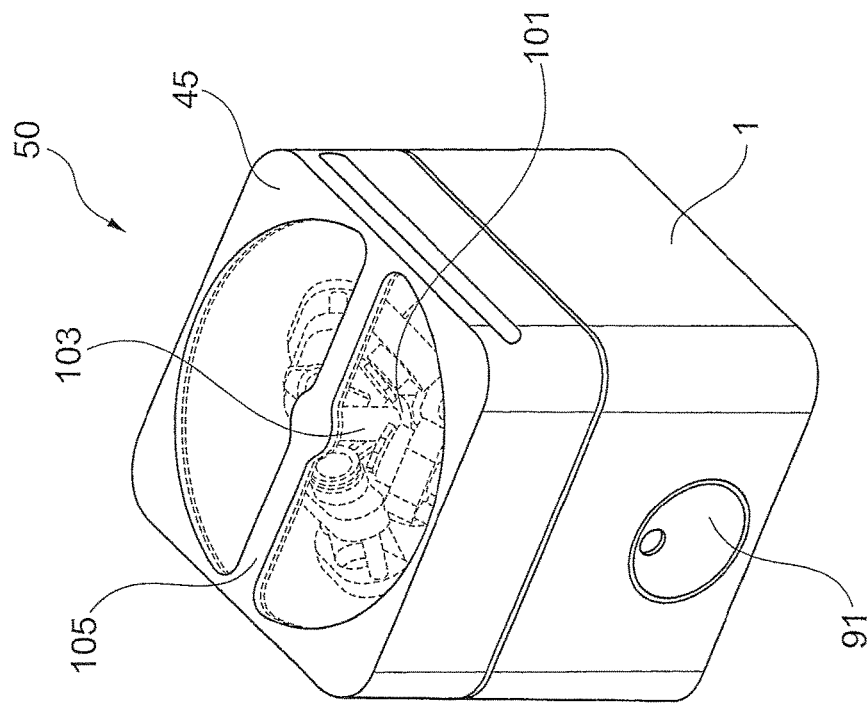
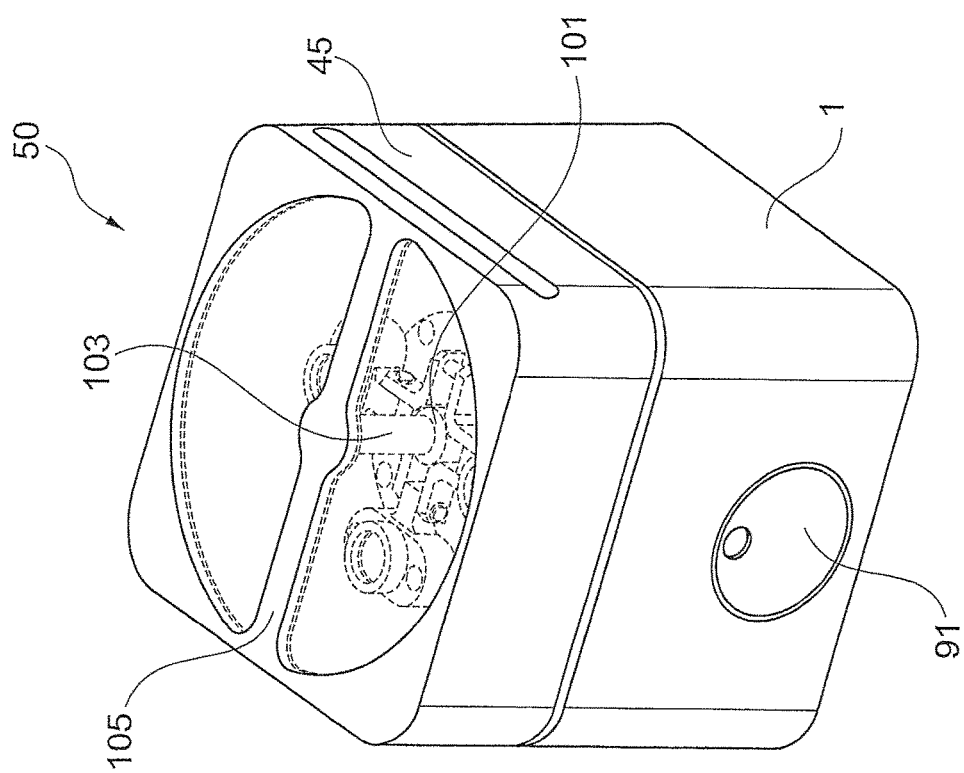

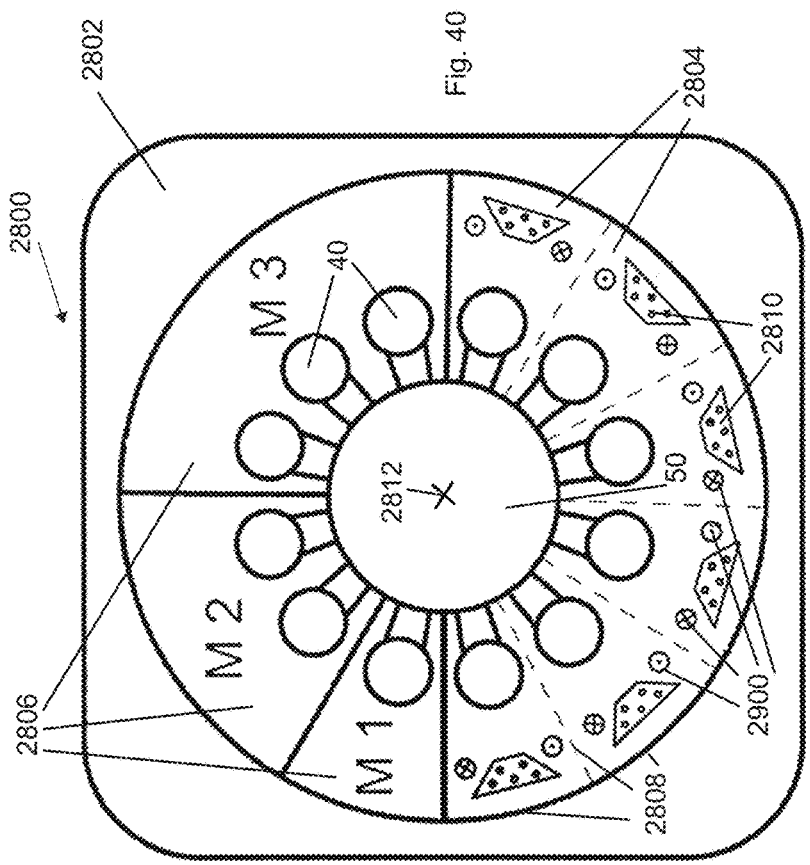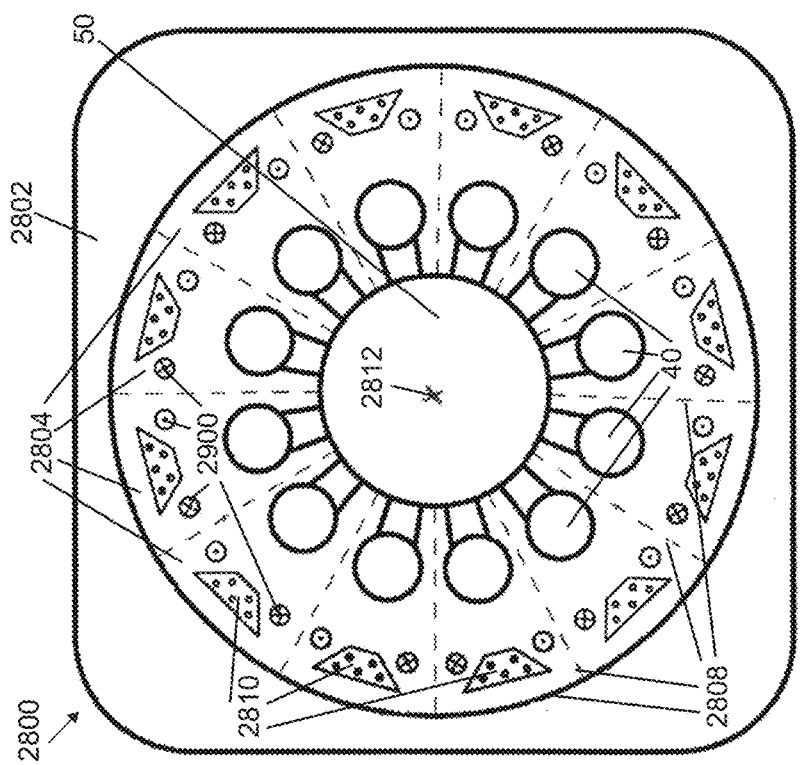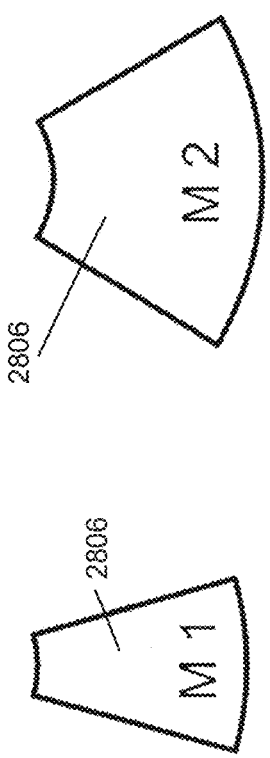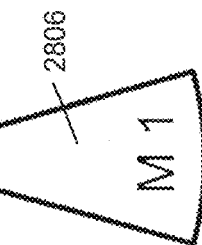

APPLICATION-SPECIFIC SAMPLE PROCESSING BY MODULES SURROUNDING A ROTOR MECHANISM FOR SAMPLE MIXING AND SAMPLE SEPARATION

CROSS-REFERENCE TO RELATED APPLICATIONS

This patent application is the U.S. national phase of International Application No. PCT/EP/2014/063774, filed on Jun. 27, 2014, which claims the benefit of Great Britain Patent Application No. 13174416.1, filed Jun. 28, 2013, and European Patent Application No. 1311667.8 filed Jun. 28, 2013, the disclosures of which are incorporated herein by reference in their entireties.

BACKGROUND OF THE INVENTION

The invention relates to a sample processing arrangement for processing a fluidic sample and a method of configuring a sample processing arrangement for processing a fluidic sample in accordance with a user selection.

U.S. Pat. No. 4,990,130 discloses a device for imparting sequentially centrifugal force or agitation to a fluid sample placed in the device, comprising a source of power, reversible rotatable motor means, flow communication means extending between said power source and said rotatable motor means, control means in said flow communication means for controlling the direction of rotation of said rotatable motor means, a drive shaft extending from said reversible motor means, a first clutch mounted on said drive shaft, said first clutch fixed for driving with said drive shaft in a first direction, and freely rotatable on said shaft in a second direction, a second clutch mounted on said drive shaft, said second clutch freely rotatable on said drive shaft in said first direction, and fixed for rotation on said shaft in said second direction, a rotor connected to said first clutch, a cam follower mounted for rotation with said rotor, a cam connected to said second clutch, means connected to said control means and movable for preventing rotation of said rotor with said first clutch in said second direction of rotation, and means for supporting fluid samples on each end of said rotor.

JP 2007-237036 discloses to provide a small sized and lightweight agitating and spin-down device for physical and chemical experiments. In this agitating and spin-down device in physical and chemical apparatus, an eccentric cam is provided at the lower face of a movable shaft, two inner and outer one-way clutches controlling rotation and non-rotation are provided between the movable shaft and a rotor stage fit to the upper part, and shaft alignment is performed by making an eccentric amount zero by winding of the eccentric cam accompanied with the normal rotation of a power shaft. A head rubber on the rotor stage is rotated by the rotation control of the one-way clutch, the shaft alignment is released by return of the eccentric cam to the original position accompanied with reverse rotation of the power shaft, the head rubber is switched to vibration by the non-rotation control of the one-way clutch to vibrate and agitate liquid in a test tube on the head rubber, and then agitation liquid attached to the inner face of the test tube is spun down by switching the head rubber to rotation.

However, it may be cumbersome to combine such conventional systems with other fluid processing tasks.

BRIEF SUMMARY OF THE INVENTION

It is an object of the invention to efficiently enable mixing, separating and further processing fluidic samples with a high level of flexibility.

In order to achieve the object defined above, the subject-matter according to the independent claims is provided. Further embodiments are shown by the dependent claims.

According to an exemplary embodiment of the invention, a sample processing arrangement for processing a fluidic sample is provided, the sample processing arrangement comprising a sample holder for accommodating the fluidic sample (in one or more sample containers), an apparatus having a rotor mechanism and being configured for selectively operating the sample holder (for accommodating the fluidic sample) in an orbital motion mode for sample mixing, particularly for shaking, or in a rotary motion mode for sample separation, particularly for centrifuging, a mounting platform having a central portion on which the apparatus and the sample holder are mounted and having a surrounding portion circumferentially surrounding the central portion, and a plurality of module accommodation positions (such as plug-in positions) circumferentially distributed in the surrounding portion to surround the rotor mechanism and the sample holder, wherein each of the module accommodation positions is configured for detachably (particularly for manual detachment by a user) accommodating a selectable one of a plurality of sample processing modules, each being configured for fulfilling an assigned sample processing task (which may differ from the tasks of sample mixing and sample separation), by accommodating (for example by plugging) the respective sample processing module in the respective one of the module accommodation positions.

According to another exemplary embodiment of the invention, a method of configuring a sample processing arrangement for processing a fluidic sample in accordance with a user selection is provided, wherein the method comprises accommodating the fluidic sample in a sample holder, selectively operating the sample holder accommodating the fluidic sample in an orbital motion mode for sample mixing, particularly for shaking, or in a rotary motion mode for sample separation, particularly for centrifuging, using an apparatus having a rotor mechanism and being mounted on a central portion of a mounting platform, detachably accommodating selected ones of a plurality of sample processing modules, each being configured for fulfilling an assigned sample processing task, in a plurality of module accommodation positions being circumferentially distributed in a surrounding portion of the mounting platform circumferentially surrounding the central portion to surround the rotor mechanism, and processing the fluidic sample by the sample processing modules being accommodated in the module accommodation positions.

In the context of this application, the term "sample holder" may particularly denote any physical structure delimiting a sample accommodation volume and hence being configured for holding a fluidic sample or a fluidic sample container. Examples are circularly arranged sample containers, matrix-like well plates, or individual fluid containers such as vials of any shape and dimension.

In the context of this application, the term "fluidic sample" may particularly denote a sample comprising a fluid, i.e. a liquid and/or gaseous medium, optionally comprising solid particles as well. Examples for fluidic samples are chemical or biochemical solutions which may comprise, for instance, one or more fractions of cells, proteins, genes, etc.

In the context of this application, the term "orbital motion", particularly orientation-fixed orbital motion, may particularly denote a motion along a trajectory which is obtained when a structure is rotating with a first angular frequency around a first central rotation axis with a superposed additional rotation with a second angular frequency around a second rotation axis, which may be parallel to the first rotation axis. The second angular frequency may have an opposite sign and may have the same absolute value as the first angular frequency.

In the context of this application, the term "rotary motion" may particularly denote a motion along a trajectory which is obtained when a structure is rotating with a certain angular frequency around one rotation axis.

In the context of this application, the term "shaking" may particularly denote a treatment of the fluidic sample for mixing components thereof. Shaking may be performed in a contamination-free and gentle manner by exposing the fluidic sample to an acceleration triggered by orbital motion.

In the context of this application, the term "centrifuging" may particularly denote a treatment of the fluidic sample for separating components thereof into different fractions. Centrifuging may be performed in an efficient manner by rotating the fluidic sample, thereby separating components thereof due to different behavior of different fraction upon exerting a centrifugal force.

According to an exemplary embodiment of the invention, a fully modular and user-adaptable sample processing arrangement is provided having in a center thereof a rotor-based mechanism for selectively centrifuging fluidic samples in a rotary motion mode or shaking the fluidic sample in an orbital motion mode. Such a rotor-based mechanism may perform the described tasks with a single rotor driven by a single drive unit around a single rotation axis (apart from the fact that the orbital motion mode implements a second, slightly parallel shifted rotation axis which however is driven with the same drive unit). Such a mechanism is an appropriate basis to handle sample containers of a sample holder by rotating them until they reach a desired working position, simply by operating the rotary motion mode only along a predefined rotation angle. A particular sample container may then be brought in spatial alignment with a sample processing module to perform a specific sample processing task. This architecture allows for an integrated sample processing arrangement which implements, circumferentially distributed around the rotor-based mechanism, several module accommodation positions or plug-in ports or docket stations, each configured for temporarily receiving and accommodating a desired a sample processing module. Thus, one or more sample processing modules appropriate for a specific application may simply be plugged into (or connected in another way) selectable ones of the module accommodation positions to obtain a completely user-defined modular and freely selectable configuration of sample processing modules fulfilling in combination a selectable plurality of sample processing tasks. The rotational symmetry of the orbital shaking and sample separation mechanism in the center in combination with the easily implementable sample alignment feature cooperates synergetically with the rotationally symmetric arrangement of the module accommodation positions, thereby obtaining a highly compact and rapidly operable integrated sample processing system. It is particularly dispensable to handle sample containers in a complex and time-consuming way for performing the individual sample processing tasks. In contrast to this, it is sufficient to simply surround the rotor-based mechanism including also the fluidic sample containers by the selecting specifiable sample processing modules to establish a desired fluid processing configuration or protocol.

In the following, further exemplary embodiments of the sample processing arrangement and the method will be explained.

In an embodiment, a user rearranges at least a part of the plurality of sample processing modules over the plurality of module accommodation positions for a subsequent use of the system. Particularly, this rearrangement may be performed by detaching at least one of the previously accommodated sample processing modules from the respective module accommodation position and/or by accommodating another one of the plurality of sample processing modules in a previously unoccupied one of the plurality of module accommodation positions. Thus, by a simple unplugging and re-plugging operation, the user may reconfigure the system for another task. This allows to use one and the same sample processing arrangement for very different applications without the need of a time-consuming and complex completely new formation of an arrangement. In contrast to this, it is sufficient according to exemplary embodiments of the invention to simply use the various module accommodation positions for mounting thereon specific sample processing modules fulfilling the tasks required for certain application.

In an embodiment, at least a part of the plurality of module accommodation positions has a mechanical interface configured for accommodating the respective sample processing module by a form closure. Involving such a form factor makes it impossible to erroneously mount sample processing modules on module accommodation positions. The mechanical interface can be formed by shaping the module accommodation position so as to configure it in accordance with a counter-shape of a sample processing module (i.e. having a mechanical counter-interface) to be received by this module accommodation position. In one embodiment, the module accommodation position may comprise a recess shaped and dimensioned for receiving the corresponding sample processing device. It is however also possible that the module accommodation position has a protrusion which receives a corresponding recess of a sample processing module. By such corresponding form factors which require a match between a sample processing module and a module accommodation position to establish a mechanical connection between the module accommodation position and the sample processing module avoids an erroneous coupling between a non-fitting pair of module accommodation position and sample processing module, thereby improving the operation safety.

In an embodiment, at least a part of the plurality of module accommodation positions has a mechanical interface configured for accommodating the respective sample processing module by a force closure. It is for instance also possible that the sample processing modules are connected to the module accommodation positions by a spring mechanism or by a magnetic mechanism.

In an embodiment, at least a part of the plurality of module accommodation positions has an electrical interface configured for supplying electric energy and/or configured for an electrical data exchange with the respective sample processing module (i.e. having an electrical counter-interface) when being accommodated in the respective module accommodation position. Such an electrical interface may have one or more of multiple purposes. A first purpose is the supply of electric energy from the sample processing arrangement to an accommodated sample processing module. Therefore, the sample processing modules may remain free of a separate intrinsic energy supply unit and can therefore all be supplied with electric energy provided by the mounting platform. Thus, the sample processing modules may be configured with low weight, in a compact size and without own energy supply resources. For example, it may be sufficient that an electric cable of the mounting platform is connected to a mains supply to thereby supply all connected sample separation modules as well as the rotor mechanism with electrical energy. On the other hand, the electrical connection may serve for a data communication (for instance for transmitting control commands, or for sending detection data) from the mounting platform to the modules, or vice versa. For example, a central control unit may be integrated in the mounting platform for the purpose of a unidirectional or bidirectional transmission of data.

The skilled person will understand that, additionally or alternatively to the provision of an electrical interface for data exchange (in an unidirectional or bidirectional way), it is for instance also possible to handle the data transmission by means of an optical interface at the module accommodation positions allowing for an optical or optoelectronic communication between an accommodated sample processing module and the mounting platform. It is also possible to perform data communication by a wireless data communication system such as based on radiofrequency communication, Bluetooth, etc.

In an embodiment, at least a part of the plurality of module accommodation positions has a fluidic interface configured for an exchange of a fluid (such as a liquid and/or a gas) with the respective sample processing module (which may therefore have a cooperating fluidic counter-interface) when being accommodated at the respective module accommodation position. Hence, also the supply of fluids may be performed via the module accommodation positions. For instance, at least a part of the module accommodation positions may comprise a fluid supply interface configured for supplying fluid to a sample processing module received in the corresponding module accommodation position. It is also possible that at least a part of the module accommodation positions comprises a fluid drain unit configured for draining fluid (such as a waste fluid or a sample fluid) from a corresponding one of the fluid processing modules accommodated in the corresponding module accommodation position. Thereby, also the fluid supply of the fluid processing modules may be handled via a universally usable interface.

In an embodiment, the respective mechanical, electrical, data communication or fluidic interface between the respective module accommodation position and the respective sample processing module is activated by accommodating the respective sample processing module in the respective module accommodation position. In other words, the module accommodation positions in combination with the correspondingly designed sample processing modules may allow to establish a mechanical and/or electrical and/or data communication and/or fluidic coupling between the mounting platform and the fluid processing modules by simply plugging or inserting the fluid processing modules into the corresponding module accommodation positions. In other words, upon accommodating a fluid processing module in the module accommodation position the mechanical, electrical, data communication and/or fluidic coupling between the module and the platform is established. Hence, a user may form one or multiple of such different kinds of connections with a single intuitive action, i.e. the insertion of a fluid processing module into the corresponding module accommodation position.

In an embodiment, the plurality of module accommodation positions are circularly and concentrically distributed around a rotor axis of the rotor mechanism. More precisely, the arrangement of the fluid processing modules may be concentric around a rotor axis assigned to the rotary motion mode. Therefore, the distance between each of the sample processing modules and the center of the rotor may be the same or basically the same.

In an embodiment, the fluidic sample, when accommodated in the sample holder, is arranged between the plurality of module accommodation positions and the rotor axis. Particularly, multiple sample containers may be distributed circularly and concentrically around the rotor axis (relating to the rotary motion mode). Also the circular arrangement of sample containers may be concentric with the circular arrangement of the module accommodation positions. Therefore, a highly symmetric configuration is achieved in which each individual sample container can be brought in equidistant alignment and therefore functional correlation with any desired one of the fluid processing modules. The transport paths of fluidic sample towards a fluid processing module may be therefore kept very small and constant regardless of which sample processing module is presently used, also allowing for a rapid fluid processing.

In an embodiment, at least a part of the plurality of module accommodation positions is configured for accommodating the same sample processing module. By configuring two or more of the module accommodation positions in the same way, standard or universally usable module accommodation positions may be provided. Therefore, since the shape and dimension of two or more of such module accommodation positions may be identical, each of them may receive the same fluid processing module so that a user can configure a complete sample processing arrangement in accordance with her or his preferences.

In an embodiment, the plurality of module accommodation positions are grouped into multiple groups of module accommodation positions, each group being configured for accommodating only an assigned group of same sample processing modules. For example, the module accommodation positions of a first group may all have the same shape and dimensions so as to be capable of receiving the same type of fluid processing module. A second group of module accommodation positions may have another shape and/or dimension, thereby being capable of receiving another type of sample processing modules. Hence, different groups of module accommodation positions may be distinguished which may intuitively guide a user to use appropriate sample processing modules only in combination with appropriate module accommodation positions. Therefore, it may be possible to intuitively guide even an unskilled user through a complex sample processing arrangement without the danger that erroneous connections between modules and positions are made.

In an embodiment, the sample holder comprises a plurality of sample containers each configured for accommodating a respective fluidic sample and each configured for being rotatable around a common rotor axis of the rotor mechanism. Sample holders of very different configurations may be implemented. It is for instance possible to use a microtiter plate or well plate as sample holder in which multiple fluidic sample containers are arranged in a matrix-like pattern, i.e. in rows and columns. It is alternatively also possible to use a plurality of circumferentially arranged fluidic sample containers rotating concentrically around the rotation axis in the rotary motion mode. The latter embodiment is particularly preferred, since it extends the rotationally symmetric arrangement of the rotor and of the module accommodation positions and the assigned sample processing modules also with regard to the sample containers. Therefore, a distance between one of the sample containers and one of the sample processing modules presently brought in alignment with the sample container may be identical for all sample containers, thereby allowing for a very simple and universal operation of the system.

In an embodiment, the apparatus is configured for selectively operating the sample holder in a module alignment mode in which the rotor mechanism is operated to move a predefined one of the plurality of sample containers in alignment with a predefined one of the plurality of module accommodation positions so as to spatially align the predefined sample container with a sample processing module in the predefined module accommodation position for subsequently executing the assigned sample processing task. The system may be further controlled so that, after the sample container has been moved to flush with the sample processing module, the sample container may cooperate with the sample processing module for sample processing. As described above, a rotor mechanism is required anyway in the sample processing arrangement so as to be capable of providing the rotary motion mode and the orbital motion mode. The present inventors have identified that this hardware already provides the basis for another operation mode which only requires a correspondingly adapted control mechanism of the rotor mechanism. Namely, in the alignment mode, the rotor may drive the sample holder towards a predefined target position in which a specific sample container is brought into functional and positional alignment with a target sample processing module in which position a desired interaction or functional cooperation between sample processing module and aligned sample container is enabled. Also for this purpose, the rotationally symmetric arrangement of the sample processing arrangement is advantageous.

In an embodiment, the sample processing arrangement comprises a control unit configured for operating the apparatus in the rotary motion mode, the orbital motion mode and the module alignment mode and for operating at least one sample processing module accommodated in an assigned module accommodation position for executing the assigned sample processing task so as to perform a fluidic sample processing in accordance with a predefined processing protocol (which may involve sample mixing, sample separation, and at least one further fluid processing task). Hence, a user may define a desired processing protocol according to which a fluidic sample is to be processed. Such a processing protocol may be sent in the form of control commands to the control unit. The sample processing arrangement may be correspondingly equipped with an appropriate number of certain sample processing modules. After such a configuration or calibration, the sample processing arrangement processes the fluidic samples in accordance with the predefined processing protocol, thus this process may be partly or even entirely controlled by the control unit (such as a microprocessor, central processing unit or the like). Therefore, even complex combinations of sample treatment sequences are possible.

In an embodiment, the sample processing arrangement comprises the plurality of sample processing modules each being configured for being accommodated in one or more of the plurality of module accommodation positions. Therefore, by providing the sample processing arrangement together with a set of fluid processing modules, a freely combinable system is provided which allows a user to use any desired module combination to perform fluidic sample processing tasks.

Still referring to the previously described embodiment, at least one of the plurality of sample processing modules may be configured for being accommodated in at least two of the plurality of module accommodation positions at the same time. Thus, it is possible to configure the arrangement so that sample processing modules having a particularly high demand in terms of provided services (for instance concerning accommodation space, number and/or kind of supply energy interfaces, data communication interfaces, fluidic interfaces, etc.) can be plugged into multiple (particularly juxtaposed) module accommodation positions (see for instance FIG. 39 to FIG. 41).

In an embodiment, the plurality of sample processing modules comprise at least one of the group consisting of a temperature adjustment module configured for adjusting a temperature of the fluidic sample, a metering module configured for metering substance to be inserted into the sample holder, a collection module configured for collecting at least a part the fluidic sample from the sample holder, a sensing module configured for sensing at least one parameter of the fluidic sample in the sample holder, an analysis module configured for analyzing the fluidic sample in the sample holder, a magnetic separation module configured for magnetically separating the fluidic sample in the sample holder, a waste module configured for removing a waste substance from the fluidic sample in the sample holder, and a storage module configured for storing at least one substance. Temperature adjustment may include heating, cooling or regulating a temperature or temperature profile for a certain fluidic sample. This may also involve the application of a complex temperature-time protocol as may be required for instance for biological treatments such as polymerase chain reaction or the like. A metering or dosing module may allow to supply a predefined amount of solid, liquid and/or gaseous components to the fluidic sample and/or a defined withdrawal of sample material from the sample containers. Collecting a certain amount of fluidic sample from the sample containers, for instance after a treatment, allows to perform a proper analysis of the success or the result of a fluid processing task. A sensing module may sense or detect one or more parameters of a fluidic sample after treatment. Even a magnetic separation module may be added which is capable of separating different components of the fluidic sample based on different magnetic behavior of their components. Parts of the fluidic sample which are no longer needed can be drained by a waste module into a waste container. A storage module may allow to store buffers, fluidic samples, or even solid or gaseous components to be used for the fluid processing. The given list of sample processing modules is not exhaustive and can be extended to further fluid processing tasks in the framework of the modular architecture of embodiments of the invention.

In an embodiment, the sample processing arrangement comprises a sample and/or sample container handling unit configured for handling fluidic sample with regard to the sample holder and/or configured for handling one or more sample containers of the sample holder. Such a sample and/or sample container handling unit may fulfil the task of equipping the sample holder with sample containers on the one hand and/or may fulfil the task of supplying fluidic sample into such fluidic sample containers.

In an embodiment, the sample and/or sample container handling unit comprises at least one of the group consisting of a sample supply robot, a sample container handling robot, a pipetting system and a metering pump. A sample supply robot may grip and handle sample containers using movable robot arms or the like. In a similar way, a sample container handling robot may also handle fluidic samples to transport them into the sample containers of the sample processing arrangement and away from them. A pipetting system may comprise one or a plurality of pipettes being controllable so as to either supply fluidic sample to one or more sample containers of the sample holder or to withdraw sample material from the sample containers for use apart from the sample processing arrangement. A metering pump can be a syringe pump or the like which is capable of intaking fluidic sample and subsequently supplying the metered fluidic sample into fluid containers of the sample holder.

In an embodiment, the sample and/or sample container handling unit forms at least one of the plurality of sample processing modules. Therefore, in one embodiment, the sampling supply and draining may be integrated in the sample processing modules. However, in an alternative embodiment, this task may be fulfilled by an external handling arrangement such as a robot.

In an embodiment, the apparatus has a support body (or stator) being stationarily mounted in the central portion of the mounting platform and has an accessible, particularly an openable and/or detachable and/or pivotable, lid covering the sample holder in a closed state and exposing the sample holder with regard to an environment in an open state. In such an embodiment, the support body may form one common device with the mounting platform, thereby constituting the stator part of the sample processing arrangement. The sample holder is coupled with the rotor mechanism so as to rotate within this stator. However, it is advantageous to get easy access to the sample containers within the sample processing arrangement. For this purpose, a lid is attached in a removable or movable way on the stationarily mounted support body. By manually or automatically moving the lid it can be actuated to get access to the sample containers. It can however also be closed so as to hermetically seal the fluidic containers in an interior thereof which is for instance required for safety reasons in a centrifuging mode or an orbital shaking mode.

In an embodiment, the lid has a recess (such as an opening) in a top surface thereof which is selectively closable or openable by moving a slidable plate so that the plate covers the recess in the lid in a closed state and uncovers or exposes the recess in the lid in an opened state. The provision of a recess in a top surface of the lid which recess is selectively coverable or covered by a slidable plate or exposable or exposed by removing the slidable plate from the recess provides an automatically operable system which allows both operation safety in the closed state of the lid and easy automatic access to sample containers within the lid and the support body for sample handling and sample container handling purposes on the other hand.

In an embodiment, the plate comprises an actuation pin being operable (for instance being grippable and slidable by a user) along a rotation trajectory for sliding the plate below an upper surface of the lid for exposing an interior of the apparatus to an external environment and for sliding the plate to cover the recess of the lid for closing the apparatus. The actuator pin may be rigidly coupled with the slidable plate so that motion and actuation of the actuation pin also actuates the slidable plate. By moving the actuation pin along a first direction along the rotation trajectory allows to open the recess by removing the plate therefrom, and motion in the opposite direction allows to cover the recess by the plate to close the lid.

In an embodiment, the sample processing arrangement comprises a lid actuation unit (particularly being motor-controlled) configured for actuating the lid to convert the lid between the closed state and the open state. In other words, a motor driven system of actuating the actuation pin may be provided so that the covering or uncovering of the recess in the lid can be integrated in the sample processing protocol as well. Therefore, a fully automatic sample processing system may be provided which meets all safety requirements.

In an embodiment, the lid actuation unit is a belt drive mechanism. Such a belt driven mechanism allows with a simple electric motor to transfer a rotation motion of a drive shaft of the electric motor into an actuation force which moves the cover plate in a forward or backward direction to selectively open or close the recess.

In an embodiment, the sample holder, the rotor mechanism, the mounting platform and the plurality of module accommodation positions are arranged within a volume delimited by the support body and the lid. Such an embodiment provides for a very compact arrangement in which damage of the components within the interior volume by external influences is safely prevented as well as a risk of injury for a user by these components when being in operation. For example, the sample holder, the rotor mechanism and the module accommodation positions including the accommodated sample processing modules may be securely received within an outermost casing of the apparatus.

In an embodiment, the lid has an actuator configured for actuating a movably mounted latch so as selectively lock the latch within an indentation in the slidable plate (for instance an indentation at a circumference of the plate) so that the latch locks the plate to the lid in a closed state of the recess in the top surface of the lid. Thus, the lid comprises an additional indentation (such as a groove or a notch or a through hole or a blind hole). This indentation, in combination with an actuator (such as a lift solenoid) may allow to keep the lid in place during operation of the system, particularly during a rotational or an orbital motion of a sample carrier between support body and lid. Hence, a user is only enabled to manually open the lid when the lid is unlocked by the actuator. This serves as an additional safety feature for protecting a user from injury.

In an embodiment, the rotor mechanism of the sample processing arrangement is configured for switching the sample holder accommodating the fluidic sample between the orbital motion mode for sample mixing, particularly for shaking, and the rotary motion mode for sample separation, particularly for centrifuging. For this purpose, the rotor mechanism may comprise a gear element being drivable by a drive unit to move (particularly to rotate) selectively in a first direction or in a second direction being inverse to the first direction, an orbital motion generator configured for generating an orbital motion of the sample holder when being operated in the orbital motion mode, and a rotary motion generator configured for generating a rotary motion of the sample holder when being operated in the rotary motion mode. A one-way clutch arrangement is provided and (particularly a first part or first one-way clutch of the one-way clutch arrangement) is configured for selectively coupling the gear element with the orbital motion generator to transfer a driving force from the gear element to the orbital motion generator for generating the orbital motion when the gear element is driven in the first direction and to freewheel when the gear element is driven in the second direction (i.e. the corresponding functional part of the one-way clutch arrangement may freewheel without transmitting a force when the gear element is driven in the second direction). The one-way clutch arrangement (particularly a second part or second one-way clutch of the one-way clutch arrangement) may be further configured for, in an alternative operation mode, selectively coupling the gear element with the rotary motion generator to transfer a driving force from the gear element to the rotary motion generator for generating the rotary motion when the gear element is driven in the second direction and to freewheel when the gear element is driven in the first direction (i.e. the corresponding other functional part of the one-way clutch arrangement may freewheel without transmitting a force when the gear element is driven in the first direction). In the context of this application, the term "gear element" may particularly denote a physical structure capable of transmitting a force between two members which are mechanically coupled by the gear element. Such a gear element may be a hollow shaft coupling a first member accommodated within the hollow shaft with a second member accommodated around the hollow shaft. Alternatively, such a gear element may be a reciprocating element coupling a member coupled to one section of the reciprocating element with another member coupled to another section of the reciprocating element, etc. In the context of this application, the term "drive unit" may particularly denote a device capable of generating a mechanical driving force. Such a driving force may be applied by an engine drive unit as engine power, by a user actuating a manual drive via muscle force, etc. In the context of this application, the term "one-way clutch" may particularly denote a clutch, i.e. a force coupling element, which transmits a drive force between two connected members in one motion direction (for instance in one rotation direction such as a clockwise rotation) but which inhibits or disables transmission of a drive force in another, particularly opposite, direction (for instance in an inverse rotation direction such as a counterclockwise rotation). In the context of this application, the term "freewheel" may particularly denote a characteristic of a one-way clutch to be incapable of transmitting a drive force to a coupled member in a certain direction so that the one way-clutch rotates freely around the certain direction without taking along the other member. Hence, a mechanism is provided for activating either an orbital motion mode (particularly an orientation-fixed orbital shaking motion) or a rotary motion mode (particularly a centrifuging motion) merely by inversing a drive direction of a drive unit which only provides the drive power. Particularly, a one-way clutch arrangement couples a gear element selectively to an orbital motion generator assembly for generating an orbital motion or to a rotary motion generator assembly for generating a rotary motion of a sample holder accommodating a sample. When the one-way clutch arrangement couples the gear element to one of the orbital motion generator or the rotary motion generator for force transmission, the respectively other motion generator is deactivated by a freewheeling of the one-way clutch arrangement in this coupling direction. The selection whether the orbital motion mode or the rotary motion mode shall be activated can be made merely by selecting a rotation direction of a drive unit such as an electric engine. Therefore, an easily operable dual-mode system is provided allowing to flexibly switch between an orbital mixing mode of the fluidic sample and a centrifuging mode of the fluidic sample merely by changing a rotation direction of the gear element. Hence, both functions may be integrated in a single device.

In an embodiment, the orbital motion generator and the rotary motion generator may be at least partially constituted by the same components (such as three cogwheels which contribute to the orbital motion generation as well as to the rotary motion generation). In this embodiment, the orbital motion generator and the rotary motion generator may at the same time be at least partially constituted by different components (such as a drive shaft which contributes only to the orbital motion generation, but not to the rotary motion generation).

In an embodiment, the one-way clutch arrangement comprises a first one-way clutch configured for coupling the gear element with the orbital motion generator to transfer the driving force from the gear element to the orbital motion generator for generating the orbital motion when the gear element is driven in the first direction and to freewheel when the gear element is driven in the second direction. Such a one-way clutch arrangement comprises a second one-way clutch (being a separate physical structure than the first one-way clutch) configured for coupling the gear element with the rotary motion generator to transfer the driving force from the gear element to the rotary motion generator for generating the rotary motion when the gear element is driven in the second direction and to freewheel when the gear element is driven in the first direction. Hence, it is possible to constitute the one-way clutch arrangement from two different one-way clutches—one coupling a first section of the gear element with the orbital motion generator and the other one coupling a second section of the gear element with the rotary motion generator. In this scenario, always only one of the two one-way clutches is active for force transmission and the respective other one is inactive or freewheels. This provides a mechanism which allows to select the motion mode merely by adjusting the rotation direction of the gear element.

However, as an alternative to two separate one-way clutches, the one-way clutch arrangement may for instance be also realized by a shiftable locking pin (or any other kind of locking element) in combination with two freewheeling bearings between the gear element on the one hand and the orbital motion generator and the rotary motion generator, respectively, on the other hand. By engaging the locking pin between gear element and orbital motion generator, these two components may be rigidly coupled so that an orbital motion mode is selected. At the same time, the locking pin has no influence on the freewheeling bearing between the gear element and the rotary motion generator so that the rotary motion mode is deactivated in this configuration. Upon shifting the locking pin to another position in which it rigidly couples the gear element with the rotary motion generator while allowing the orbital motion generator to freewheel relative to the gear element by the freewheeling bearing, the rotary motion mode may be selected. The skilled person will understand that other alternatives for realizing the function of the one-way clutch arrangement are possible.

In an embodiment, the first one-way clutch and the second one-way clutch freewheel in opposite directions and lock in opposite directions. For instance, the first one-way clutch may freewheel in a clockwise rotation direction while locking in a counterclockwise rotation direction, or vice versa. The second one-way clutch may then freewheel in the counterclockwise rotation direction while locking in the clockwise rotation direction, or vice versa. Therefore, by selecting a rotation direction of the gear element, it is selectable which one of the one-way clutches locks and which one freewheels.

In an embodiment, the gear element is configured as a hollow shaft. Such a hollow shaft, which may have a tubular or hollow cylindrical geometry, may be directly coupled to a drive unit for providing the driving force or power, such as an electric motor.

In an embodiment, the first one-way clutch is arranged between an interior surface of the hollow shaft and an exterior surface of a drive shaft of the orbital motion generator. The second one-way clutch may be arranged between an exterior surface of the hollow shaft and an interior surface of a movably mounted cogwheel (or a tubular cogwheel extension shaft thereof) of the rotary motion generator. Thus, an outer surface of the hollow cylindrical shaft may be coupled for transmitting rotary motion force, while an inner surface of the cylindrical hollow shaft may be coupled for transmitting orbital motion force. However, the arrangement may be also vice versa.

In an embodiment, the rotary motion generator comprises a selectively lockable first cogwheel in an unlocked movably mounted state, coupled to the gear element via the one-way clutch arrangement and having a plurality of first cogs arranged along an outer circumference of the first cogwheel, and a movably mounted second cogwheel having a plurality of second cogs arranged along an outer circumference of the second cogwheel. A coupling body is provided having a plurality of third cogs arranged along an inner circumference of the coupling body. The coupling body is mounted with the first cogwheel and with the second cogwheel to engage part of the first cogs and part of the second cogs by part of the third cogs to thereby generate the rotary motion of the second cogwheel and a sample holder to be mounted to follow a motion of the second cogwheel upon rotating the gear element in the first direction. In the context of this application, the term "cogs" may particularly denote physical structures such as rips, teeth or any other kind of protrusions of a physical body which are arranged in a sequence for being subsequently (and optionally partially simultaneously) engaged by corresponding cooperating grooves or indentations of another cooperating physical body for providing a force coupling between the physical bodies. Upon activating the rotary motion mode, the gear element may transmit a driving force to the movably configured first cogwheel which, via the coupling body, also drives the second cogwheel which in turn rotates the sample holder for centrifugation.

In an embodiment, the orbital motion generator comprises the selectively lockable first cogwheel in a locked stationarily mounted state and having a first through hole, the second cogwheel having a second through hole, and a drive shaft coupled to the gear element via the one-way clutch arrangement and having a concentric first section and an eccentric second section, wherein the first section is guided through the first through hole and the second section is guided through the second through hole, wherein the coupling body is mounted with the first cogwheel and with the second cogwheel to engage part of the first cogs and part of the second cogs by part of the third cogs to thereby generate the orbital motion of the second cogwheel and a sample holder to be mounted to follow a motion of the second cogwheel upon rotating the gear element in the second direction. In the context of this application, the term "concentric shaft section" may particularly denote a portion of a shaft in length direction which portion has a length axis being aligned to or identical to the rotation axis. In the context of this application, the term "eccentric shaft section" may particularly denote a portion of a shaft in length direction which portion has a length axis being parallel shifted or laterally spaced or displaced with regard to the rotation axis. Hence, by merely locking the first cogwheel to a support body or the like to fix it, a rotation force is transmitted via the eccentric second section of the drive shaft to the second cogwheel. By the weak coupling between the first cogwheel and the second cogwheel mediated by the coupling element, the orbital motion is then automatically generated.

In an embodiment, the mechanism further comprises a cogwheel locking element configured for selectively locking the first cogwheel in the locked stationarily mounted state or for unlocking the first cogwheel in the unlocked movably mounted state. Such a cogwheel locking element may be a locking pin which can be spatially shifted so as to trigger a rigid coupling between the first cogwheel and a support body or the like, or for decoupling these two elements from one another by disengaging the locking pin from the first cogwheel.

In an embodiment, the mechanism further comprises a shaft locking element configured for selectively locking the drive shaft in a locked stationarily mounted state or for unlocking the drive shaft in an unlocked movably mounted state. Also the shaft locking element may be embodied as a shiftable pin which selectably allows to lock the drive shaft to a support body or the like, or to decouple these two components from one another.

In an embodiment, each of the first cogwheel and the second cogwheel is a toothed belt disc and the coupling body is a toothed belt. Such a toothed belt disk may be a disk-shaped or cylindrical body having a curved surface which includes a circumferential arrangement of rips. Correspondingly, the coupling body may be a belt, i.e. made of a flexible material and having indentations which have a shape corresponding to the rips of the first and second cogwheels. Hence, engagement between the rips and the indentations is possible to provide for a form closure based force transmission.

In an embodiment, the mechanism comprises a support body accommodating a part or all of the components of the mechanism and comprises a lid to be attached onto the support body, wherein the support body and the lid are configured to correspond to one another so that upon attaching the lid onto the support body, the mechanism is triggered to be switched from the orbital motion mode to the rotary motion mode. Particularly, a lid attaching sensor may be provided at the lid and/or at the support body which may be configured for sensing attachment of the lid onto the support body and/or detachment of the lid from the support body. Such a provision acts as a safety feature while at the same time allowing a user to easily adjust the rotary motion mode or the orbital motion mode. In this embodiment, when the support body is uncovered (i.e. the lid is detached), the orbital motion or shaking mode is activated. Upon attaching the lid to the support body, a switch may be actuated (for instance based on a sensor signal) which changes rotation direction of the gear element. Merely by taking this measure, the motion mode is changed from the orbital motion mode to the rotary motion mode. Since centrifuging in the rotary motion mode involves in many cases significantly larger rotational forces and hence an increased risk in a lab, activating the centrifuging only upon putting the lid on the support body also increases the safety for a user.

In an embodiment, each of the first cogwheel and the second cogwheel is a sprocket and the coupling body is a sprocket chain. Therefore, several alternatives to a toothed belt configuration of the cogwheels are possible. For instance, a regular arrangement of indentations in a sprocket chain may cooperate with a corresponding arrangement of protrusions in a circumferential surface of a sprocket for force transmission.

In an embodiment, the coupling body is a flexible structure being deformable but basically non-elongatable (a slight elongation might be possible in view of a slight flexibility of the material of the coupling body) upon rotating the drive shaft so as to adapt its shape to follow motion of the second cogwheel while maintaining the coupling between the first cogwheel and the second cogwheel. The term "deformable but non-elongatable" may denote a characteristic according to which the shape of the coupling body may be changed by applying a deforming force, but that the entire length along a circumference of the coupling body may remain constant or basically constant upon applying a deforming force. Hence, the coupling body may have an inelastic behavior. By manufacturing the coupling body as a slightly flexible, but non-expandable structure, a weak coupling between the two cogwheels is enabled which provides for the necessary force transmission to generate an orbital motion. The coupling body may for instance be an annular structure made of a bendable material such as rubber covered by a non-expandable fabric or web so as to show, as a whole, the described properties.

In an alternative embodiment, the coupling body is a rigid, non-deformable structure which, upon rotating the drive shaft, follows, as a whole, motion of the second cogwheel while maintaining the coupling between the first cogwheel and the second cogwheel. In contrast to the previously described embodiment, the coupling body can also be configured as an undeformable solid body (for example made of plastic), for instance a ring with an internal toothing.

In an embodiment, the coupling body is a closed annular structure, particularly a structure being quasi-rotationally symmetric in a force-free state. Such a ring-like structure may be basically rotationally symmetric with the particularity that the internal toothing provides for a slight deviation as compared to a completely rotationally symmetric arrangement.

In an embodiment, the coupling body is an annular structure having an inner diameter which is larger than an outer diameter of the first cogwheel and the second cogwheel, particularly about one times of an eccentricity of the second section of the drive shaft larger. The largest inner extension of the coupling body may be larger, by the eccentricity, than the diameter of one of the cogwheels. The term "eccentricity" may denote a spatial, lateral shift of the eccentric portion (more particularly of a center of gravity thereof) as compared to the concentric portion (more particularly of a center of gravity thereof) and the rotation axis of the shaft.

In an embodiment, a number of the first cogs is the same as a number of the second cogs. In this case a smooth and low friction rolling of the two cogwheels on one another, coupled by the coupling element, can be obtained.

In an embodiment, the number of the first cogs and the number of the second cogs is smaller than a number of the third cogs. If the number of third cogs is larger than the number of the first cogs and the number of the second cogs, it can be ensured that in each operation mode only a portion of the first and second cogs is contacted by the third cogs, thereby promoting the desired orbital motion.

In an embodiment, in the orbital motion mode, a coupling force resulting from the form closure of the coupling body with both the first cogwheel and the second cogwheel is larger than a friction force (for instance a bearing force or bearing load in bearings of the device) between the first cogwheel and the second cogwheel. The form closure is generated by an engagement of the cogs of the cogwheels between cogs of the coupling body. The friction force between the cogwheels has the tendency to prevent relative motion between the cogwheels, while the coupling force triggers such a motion. By configuring the bearings, materials, surface roughness, driving force, etc., correspondingly, the requirement of a coupling force exceeding the friction force can be met.

In an embodiment, in the orbital motion mode, the coupling body is mounted with the first cogwheel and with the second cogwheel so as to form a form closure which superposes, to a rotating motion of the second cogwheel transmitted by the drive shaft, a rolling motion of the second cogwheel during which the second cogwheel rolls up on the coupling body limited by a rolling motion during which the coupling body rolls up on the first cogwheel. The two overlaid rotations of the second cogwheel with two parallel rotation axes allows for the generation of the orbital motion. This particularly holds when the two rotational frequencies have the same absolute values but opposite signs.

In an embodiment, the mechanism comprises a drive unit, particularly an electric motor, being configured for moving, particularly rotating, the gear element. However, it is also possible that the drive unit is a handle or the like which is operable by a user so as to initiate rotation by muscle force.

In an embodiment, the mechanism comprises a compensation weight mounted asymmetrically on the drive shaft and being configured so as to at least partially compensate for a mechanical load acting on the drive shaft upon generating the orbital motion. By providing a compensation weight which is mounted asymmetrically on the drive shaft (for instance shaped as a half disk) it is possible to compensate for unbalanced forces acting around the circumference of the drift shaft in the orbital motion mode. Therefore, by providing such a compensation weight, wear of the mechanism may be efficiently suppressed. The system may also comprise a mechanism for spatially fixing the compensation weight upon switching from the orbital motion mode to the rotary motion mode. Such a mechanism may be realized as a pin on a lid for covering a support body, wherein covering the support body with the lid may press the pin against the compensation weight thereby preventing motion of the compensation weight in the centrifuging mode.

In an embodiment, the force flow for the orbital motion mode goes from the drive unit, via the gear element, one of the one way clutches, an eccentric drive shaft, to the sample holder. The force flow for the rotary motion mode goes from the drive unit, via the gear element, another one of the one way clutches, cooperating cogwheels, to the sample holder.

In an embodiment, the mechanism further comprises a locking one-way clutch configured for coupling a drive shaft of the orbital motion generator with a stationary housing so as to selectively lock the drive shaft with the stationary housing to a locked stationarily mounted state when the gear element is driven in one direction, or to freewheel in an unlocked movably mounted state of the drive shaft when the gear element is driven in another (particularly the opposite) direction. In such an embodiment, the provision of a locking element (such as a slidable pin drivable in a groove of the shaft) for locking an eccentric drive shaft to prevent its orbital rotation during a rotary motion mode can be omitted. The simple provision of a locking one-way clutch to prevent orbital rotation of an eccentric drive shaft during a rotary motion mode allows to automatically achieve such a locking effect without the need to actively control a slidable locking element to drive in engagement with or out of engagement with the shaft.

In an embodiment, the stationary housing comprises a lid which is detachably connectable (or connected) to and/or pivotably mounted (so as to be pivotable between a closed housing state and an open housing state) on a spatially fixed support body of the stationary housing, wherein the locking one-way clutch is configured for coupling the drive shaft with the lid. Thus, the automatic locking arrangement may be easily accessible at a top of the mechanism where a lot of space is available for such a provision.

In an embodiment, the one direction equals to the second direction and the other direction equals to the first direction. Therefore, it can be ensured that the disablement of the eccentric shaft rotation occurs selectively in the rotary motion mode, but not in the orbital motion mode.

In an alternative embodiment (which does not have a locking one-way clutch), the mechanism further comprises a locking element configured for selectively locking a drive shaft of the orbital motion generator in a locked stationarily mounted state, particularly in the rotary motion mode, or for unlocking the drive shaft in an unlocked movably mounted state, particularly in the orbital motion mode. Such an alternative embodiment has the advantage that, whenever desired, a shaft motion may be safely disabled not limited to a situation in which the shaft shall be prevented against rotation in an undesired direction. This provides a user with a high degree of freedom to control of the entire mechanism in accordance with any user selections.

In an embodiment, the second one-way clutch is arranged to circumferentially surround the first one-way clutch. This allows to obtain a very compact mechanism with a particularly low height. In view of the high forces which may act on the mechanism during centrifuging and orbital mixing, such a flat construction offers a high degree of safety in operation.

In an embodiment, the first one-way clutch and the second one-way clutch are arranged concentrically around a rotation axis of the mechanism, particularly around a rotation axis of a concentric portion of a drive shaft of the orbital motion generator. Particularly, the mechanism may have a lower portion (i.e. juxtaposed to a bottom of the device) with a concentric arrangement and may have an upper portion (i.e. juxtaposed to the sample holder) with an eccentric arrangement. The one-way clutch arrangement may entirely form part of the concentric bottom arrangement which may keep the mechanical load acting on the one-way clutch arrangement small.

In an embodiment, the first one-way clutch and the second one-way clutch are arranged at at least overlapping height ranges, particularly extend over the same height range, in relation to a (particularly vertical) rotation axis of the mechanism, particularly in relation to a rotation axis of a drive shaft of the orbital motion generator. Also this contributes to the compact construction of the mechanism.

In an embodiment, the one-way clutch arrangement is mounted so as to be immovable along a rotation axis of the mechanism, particularly around a rotation axis of a drive shaft of the orbital motion generator. By maintaining the one-way clutch arrangement spatially fixed along a rotation axis of the mechanism during both the rotary motion mode and the orbital motion mode, the technical effort for moving components remains very small. This allows to operate the mechanism with a low amount of energy and keeps the construction simple and robust against failure. Hence, the one-way clutches may be assembled so as to be disabled to be displaced in a translative way along the vertical or rotation axis. However, in the rotary motion mode one of the one-way clutches rotates around the rotation axis of the hollow shaft/of the drive unit, and in the orbital motion mode the other one of the one-way clutches rotates around the rotation axis of the hollow shaft/of the drive unit.

In an embodiment, the gear element comprises a hollow shaft being located (particularly laterally) between the first one-way clutch and the second one-way clutch so as to surround the first one-way clutch and to be surrounded by the second one-way clutch. Therefore, a simple tubular gear element may organize both operation of components within the first one-way clutch as well as operation of components surrounding the second one-way clutch merely by adjusting the present rotation direction of the tubular gear element.

In an embodiment, the orbital motion generator comprises a drive shaft having an eccentric section being eccentric with regard to a rotation axis around which the gear element is rotatable driven by the drive unit, wherein the eccentric section extends through the sample holder, particularly through a recessed sample holder plate of the sample holder. Thus, the eccentric portion of the shaft may act directly on the sample holder without any further components in between. This results in a simple, failure-robust and spatially uninterrupted force transmission from the eccentric shaft section to the sample holder rendering the mechanism compact, light in weight and accurate.

In an embodiment, the drive shaft has a concentric section being concentric with regard to the rotation axis, wherein at least a part of the concentric section, but not the eccentric section, is surrounded by at least a part of the one-way clutch arrangement. Thus, a clear spatial separation between a concentric portion including the force transmitting one-way clutches on the one hand and an eccentric portion on the other hand can be implemented.

In an embodiment, the concentric section forms a bottom part of the drive shaft and the eccentric section forms a top part of the drive shaft. The terms "bottom" and "top" refer to an ordinary use position of the mechanism in which the sample containers are arranged above the drive and force transmission components.

In an embodiment, the drive shaft extends over or bridges the entire range from the drive unit to the sample holder. Therefore, a single stiff member may transfer the driving force from the drive unit to the sample holder to thereby ensure a failure robust orbital motion operation.

In an embodiment, the mechanism comprises cooperating cogwheels forming part of both the orbital motion generator and the rotary motion generator. A force transmission via two cogwheels which may be coupled by a coupling body (such as a toothed belt) is a rigid, simple and accurately reproducible way of transferring force. More precisely, the coupling body transfers a rotative motion from a lower cogwheel to an upper cogwheel during the rotary motion mode (for centrifugation), similar as in a belt drive. In the orbital motion mode, the coupling body prevents a turning of the upper cogwheel relative to the lower cogwheel. In other words, the upper cogwheel maintains its spatial orientation with regard to the lower cogwheel during the orbital revolution. Thus, there is a force coupling between the cogwheels in the orbital motion mode.

In an embodiment, the mechanism comprises a drive shaft to be coupled to the gear element via the one-way clutch arrangement and forming part of the orbital motion generator, but not of the rotary motion generator. Thus, construction of the partially eccentric drive shaft may be focused specifically to the task of transmitting an orbital motion In an embodiment, the sample holder comprises one or more accommodation sections each having an accommodation recess each configured for receiving a container including one or more fluidic samples. In one embodiment, exactly one fluidic sample is treated by the apparatus. Such a sample may be accommodated within a vial or any other container. It is however also possible that an arrangement of multiple fluidic samples is treated for mixing and/or centrifuging in the same apparatus at the same time. For instance, a circumferential arrangement of accommodation recesses and corresponding samples may be provided. Alternatively, it is also possible that for instance two dimensional arrays of samples are treated by the apparatus such as well plates or the like. For instance, a 96 well plate sample holder may be used in conjunction with the apparatus. With regard to suitable sample holders, it is possible to have four tubes, four well plates, any other number of tubes or well plates, common or separate structures for accommodating them, multiple samples, etc.

In an embodiment, each of the one or more accommodation sections is mounted to be pivotable around a pivoting axis being perpendicular to a rotation axis of the orbital motion and the rotary motion so as to be pivoted only upon exceeding a predefined rotation force. By mounting the accommodation sections to be pivotable allows to increase the centrifuging efficiency while rotating the sample holders.

It is also possible to operate the apparatus in combination with an automatic sample transfer system. For example, it is possible to pipette fluidic samples into sample containers of the apparatus. It is also possible to provide a temperature adjustment unit within the apparatus, for instance to perform PCR (Polymerase Chain Reaction) with the fluidic samples. It is also possible that the apparatus itself includes detector components such as an optical detector for detecting separated components of the sample. Alternatively, it is possible to move the apparatus into a separate detection system. For instance, a robot driven gripper arm may grip the apparatus and may transfer the apparatus towards a detector position.

It is possible that the samples are cooled (for instance by injecting an air stream into the interior accommodation space of the apparatus) or heated during centrifuging and/or during mixing.

Merely as examples, apparatuses according to exemplary embodiments of the invention may be realized as one or more of the following: an orbital shaker for lab containers; an orbital shaker for well plates with a flat construction and a high mixing frequency; a combination of an orbital shaker and a centrifuge for lab containers (also well plates); a combination of orbital shaker, centrifuge and a homogenizer (such a function may be implemented, for instance by a linear motion of a rotor, for instance reciprocating upwardly and downwardly); integration of an automatic container locking (for instance an edge locking mechanism); an integration of a sample supply and/or sample remove unit or a pipette device; integration of an evaluation device (for instance an optical detector); integration of a precise positioning unit for positioning fluidic sample containers (for example, the containers may be pivoted at defined points in order to provide for a sample supply or an evaluation here); integration of a temperature adjustment unit; etc.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

BRIEF DESCRIPTION OF THE SEVERAL VIEWS OF THE DRAWINGS

FIG. 10 illustrates a sample handling apparatus, which may be implemented in a sample processing arrangement according to an exemplary embodiment of the invention, in an operation mode in which a lid is attached to cover an interior of a support body.

FIG. 11 shows the sample handling apparatus of FIG. 10 in an operation mode in which the lid is detached.

FIG. 12 shows an internal constitution of the apparatus of FIG. 10, wherein a support body is omitted to expose various internal parts.

FIG. 13 shows a detailed view of the lid of the apparatus of FIG. 10.

FIG. 15 shows another view of the apparatus of FIG. 10 while the accommodation sections are in an upright position.

FIG. 16 shows another operation mode of the apparatus of FIG. 10, wherein the accommodation sections are in a pivoted position.

FIG. 39 is a schematic plan view of a sample processing arrangement according to an exemplary embodiment of the invention in which all twelve module accommodation positions of identical dimension are presently free of sample processing modules.

FIG. 40 is another view of the sample processing arrangement of FIG. 39 in which six module accommodation positions remain unoccupied by sample processing modules, one module accommodation position is presently occupied by one sample processing module, two module accommodation positions are presently occupied by another sample processing module, and three further module accommodation positions are presently occupied by still another sample processing module.

FIG. 41 illustrates the sample processing modules according to FIG. 40.

DETAILED DESCRIPTION OF THE INVENTION

Figure 1:
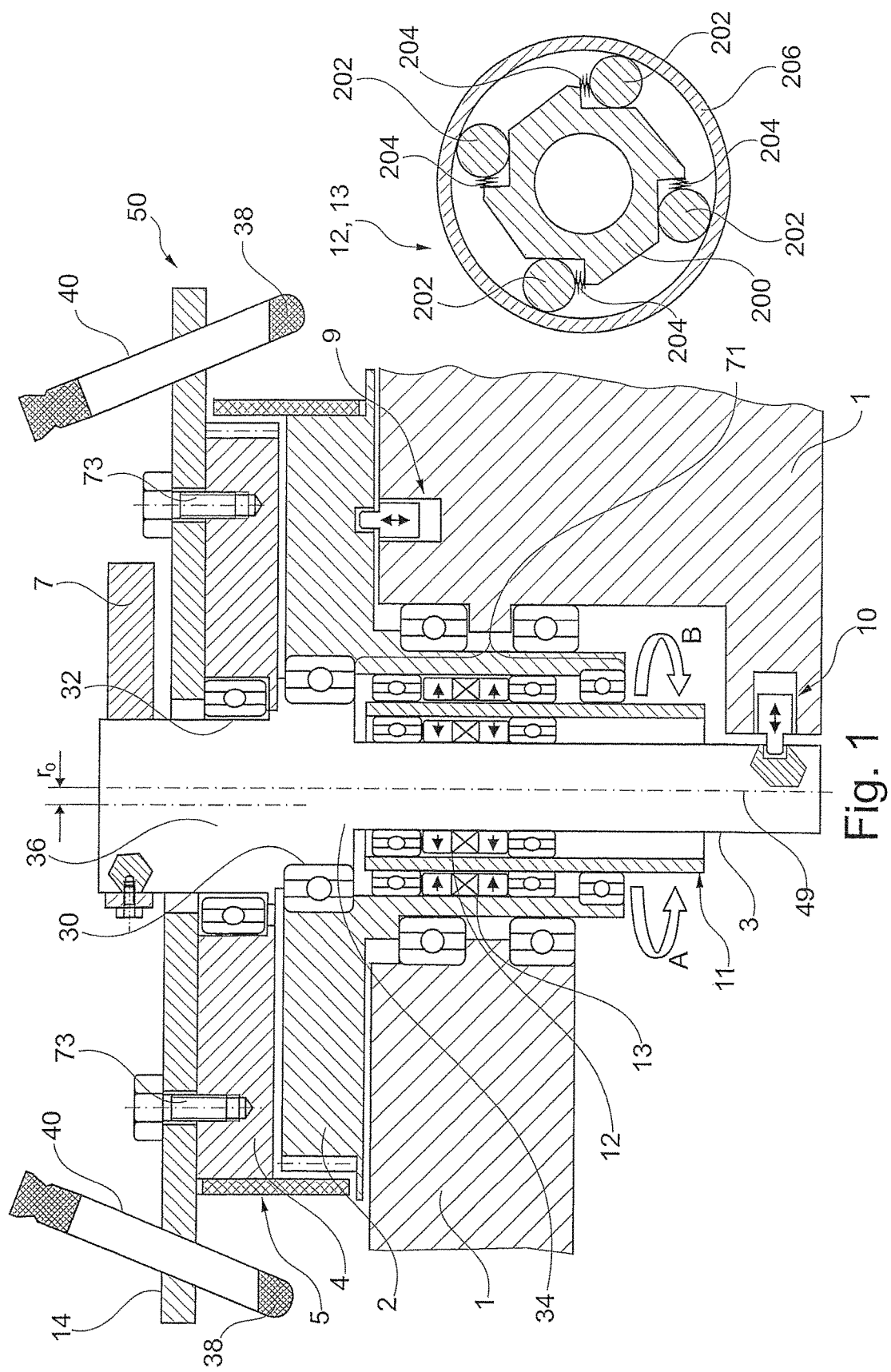
FIG. 1 shows a sample handling apparatus, which may be implemented in a sample processing arrangement according to an exemplary embodiment of the invention, for selectively operating a sample holder accommodating fluidic samples in an orbital motion mode for shaking or in a rotary motion mode for centrifuging.

The illustration in the drawing is schematically. In different drawings, similar or identical elements are provided with the same reference signs.

In the following, sample processing arrangements according to exemplary embodiments of the invention will be explained. These sample processing arrangements comprise mechanisms and apparatuses as shown in FIG. 1 to FIG. 27. In FIG. 28 to FIG. 35, it will then be described how such and other apparatuses and mechanisms can be implemented in sample processing arrangements in which they are integrated with a mounting platform providing the opportunity of plugging selectively combinable sample processing modules into plug-in positions of the mounting platform.

A basis for a sample processing arrangement according to exemplary embodiments of the invention is a rotor-based system (having a high degree of rotational symmetry) enabling sample containers mounted on a sample holder to be subjected to a rotary motion mode for sample separation or an orbital motion mode for agitation of the sample. According to an exemplary embodiment, such a system is extended by a mounting platform providing the opportunity of integrating multiple sample separation modules of different type of functionality on the same platform or even within the same casing. In view of the rotor-based mechanism, the sample containers are already functionally coupled to a rotatable rotor and can be moved and processed in different ways. Particularly, it is possible to perform mixing procedures, separation procedures and to transport individual ones of the fluidic sample containers in alignment with assigned sample processing modules.

Since the sample containers are arranged on a rotatable rotor, a simple positioning of the samples on a circular trajectory is possible. This makes it possible to position certain different processing stations or sample processing modules along a perimeter of the system and to move the samples by a simple rotation mechanism of the rotor to the respectively next processing station or sample processing module. No separate drive unit is required to perform this task, because the rotational drive used for the mixing and centrifugation can be used as well for positioning individual sample containers relative to individual sample processing modules. The supply and the extraction or sampling of substances (for instance for metering) can for instance be performed via a single linear axis in connection with a pipetting unit or a metering pump being arranged parallel to the rotor axis. Kinetic energy required for mixing and separation can be provided via the same rotor and motor and can be transmitted to the fluidic samples in the sample containers attached thereto.

By this construction it becomes possible to combine important analytical tasks and methods in a very compact device which using only two motion axes. Optionally and advantageously, further processes such as for instance tempering and magnetic separation may be integrated in the arrangement as well.

Just as an example, it is possible to integrate the following and other modules for the following and other purposes along a circumference of the device:

- trigger chemical reaction/tempering samples (for instance heating, cooling, mixing)
- metering (for instance adding solid, liquid or gaseous substances to a fluid container)
- sample collection (for instance collection of substances from a fluid container)
- characterization of sample by measurement techniques (for instance analytic, particularly optical detection)
- magnetic separation
- sucking off/disposal of auxiliary substances and waste
- storage (for instance containers of auxiliary substances, tempering of the auxiliary substances, etc.)

The sample processing modules can be configured to be accommodated substitutably (for instance by plugging them into plug-in positions). Electric interfaces may be provided in the plug-in positions of the mounting platform for supply of the sample separation modules with electric power. Also, such electric interfaces can be used for a communication of a sample separation module with other sample separation modules or a central control unit of the mounting platform. Moreover, mechanical interfaces may be provided for attaching or fastening the sample separation modules to the mounting platform. In the sample processing arrangement, the sample processing modules are placed around the rotor driving one or more sample containers in the rotary motion mode or in the orbital motion mode. Hence, a simple and flexible adjustment of the entire system is enabled. Such a modular system with standardized modules allows to adapt the system flexibly to different protocols and process chains. By an intelligent combination of different modules, many different analytical methods may be carried out. The system is particularly suitable for the execution of complex and difficult sample preparation sequences which have conventionally been performed manually (see for instance FIG. 38).

The outer casing of such an arrangement can be advantageously equipped with an automatically openable lid for integration in an automatic lab system (for instance using a lab robot). For this purpose, the arrangement can be automatically equipped by an automatic lab system (for example using a gripper or handling tool) with sample containers (for instance tubes, vials, microtiter plates, well plates, etc.). Particularly, removal of fluid from the sample containers may also be automated. The system can then carry out complex sample preparation tasks in an autonomous way. The above-mentioned lid may serve as a mechanical protection of the entire system in case of a possible damage by forces which result from the execution of rapid rotation motions, as they occur for instance during centrifugation but also during orbital mixing. On the other hand, this provides for the opportunity to provide a closed incubation volume. The incubation volume can be tempered or can be provided with a desired gas atmosphere (for instance $CO_2$, nitrogen substances) which may influence the incubation or reaction in a desired way. In order to introduce fluidic samples into the incubation volume or to remove samples therefrom, the automatically openable lid may be integrated in the arrangement. The lid may be openable or closable in a vertical and/or horizontal direction by means of drive units (such as a linear motor, a stepper motor, a servomotor, etc.).

For the purpose of performing various biological and biochemical treatments of fluidic sample, the sample processing arrangement may be equipped with different standardized modules (such as a handling unit, a pipetting unit, a temperature adjustment unit, an analysis unit for read out of data, etc.).

Exemplary embodiments of the invention allow operating an apparatus in an operation mode in which an orientation fixed orbital motion is possible. A corresponding embodiment of the invention therefore relates to a mechanism for transferring a rotation motion of a driving motor into an orientation fixed orbital motion which is advantageous for a contamination free mixing of samples in laboratory containers. In this kind of motion, a shaking shelf board with at least one laboratory container attached thereto is moved with an angular frequency $\omega_1$ around a rotational axis of a drive unit. In order to keep the spatial orientation of the lab container constant, the shaking shelf board can additionally be rotated by an angular frequency $\omega_2$ around an axis which is not identical to an axis of the drive unit but which is parallel to this axis with a distance $r_0$ (eccentricity/orbital radius). In order to maintain this spatial orientation of the shaking shelf board during the rotation, it is advantageous that the condition $-\omega_1 = \omega_2$ shall be fulfilled.

In contrast to such an orbital motion, centrifugation denotes a sample separation procedure which is based on a different behavior of different molecules in the gravitational field. The gravitational field required for separating such components thereby defines or determines the technical effort for realizing the separation. Therefore, a sufficiently high gravitational force shall be generated artificially. For this purpose, it is possible to rotate the samples within the containers around a certain spatial axis. In the thus generated centrifugal field, the separation procedures are more efficiently and faster as in the gravitational field of the earth, since the required separation forces can be significantly higher. Also a separation of mixtures of fractions of a fluidic sample with very small differences concerning density can be made possible by this procedure.

In biotechnology, centrifugation can be used for separating cells after fermentation, separating of cell fragments after cell exposure, the separation of precipitated or crystallized products from liquids and the separation of liquid systems (extraction). Another application of centrifugation in a biotechnological lab is to collect sample amounts adhering to the surface of the container after execution of tempering or mixture procedures by a centrifugal force in direction of the bottom of the container, for sample collection.

FIG. 1 illustrates a sample handling apparatus 50 according to an exemplary embodiment of the invention.

The apparatus 50 comprises a sample holder constituted by a recessed sample holder plate 14 and tubes or test glasses 40 mounted on the sample holder plate 14. As can be taken from FIG. 1, fluidic samples 38 such as biological liquids are accommodated within the test glasses 40. The apparatus 50 combines two functions in one device, i.e. a shaking function by which the liquid samples 38 are shaken for mixing purposes and a rotary function by which the liquid samples 38 are centrifuged for separating components or fractions thereof.

The sample holder 14, 40 is coupled to a mechanism for switching the sample holder 14, 40 between the orbital motion mode (for shaking) and the rotary motion mode (for centrifuging).

This mechanism comprises a hollow cylindrical shaft 11 as a gear element which can be rotated selectively in a first rotation direction A or in a second rotation direction B around a rotation axis 49. The second rotation direction B is opposite or inverse to the first rotation direction A. The rotation can be powered by a drive engine (not shown in FIG. 1).

Reference numerals 2, 3, 4 and 5 denote components of an orbital motion generator which is configured for generating the orbital motion of the sample holder 14, 40 when the apparatus 50 is operated in the orbital motion mode for mixing in accordance with the first rotation direction A. Furthermore, reference numerals 2, 4 and 5 denote components of a rotary motion generator which is configured to generating a rotary motion of the sample holder 14, 40 when the apparatus 50 is operated in the rotary motion mode in accordance with the second rotation direction B. Reference numerals 12 and 13 denote independently operating components of a one-way clutch arrangement, embodied as a first one-way clutch 12 and a second one-way clutch 13. The skilled person is aware of the fact that a one-way clutch may freewheel in one rotation direction, thereby disabling a force transmission between two connected components, while it enables a force transmission between two connected components in the opposite rotation direction. The two one-way clutches 12, 13 freewheeling in opposite directions are provided for switching between the centrifuging mechanism and the orbital shaking mechanism. Coupling between the two one-way clutches 12, 13 is performed by the hollow shaft 11.

A detail in FIG. 1 shows an example as to how a one-way clutch 12, 13 may be configured. A plurality of circumferentially arranged balls 202 are connected via biasing springs 204 to a central hub 200. The balls 202 are further sandwiched between the hub 200 and an exterior annulus 206. In clockwise direction, rotation of the hub 200 is disabled (for reasons of form closure or force closure), while it is enabled in counterclockwise direction.

As can be taken from FIG. 1, the first one-way clutch 12 is arranged between the hollow shaft 11 and a drive shaft 3. The one-way clutch 12 is configured in such a way that the driving force from the rotated hollow shaft 11 can be transferred to the orbital motion generator 2 to 5 for generating the orbital motion when the hollow shaft 11 is rotated in the first direction A. In other words, the first one-way clutch 12 couples the hollow shaft 11 with the drive shaft 3 when the first motion direction A of the hollow shaft 11 is activated. In contrast to this, the first one-way clutch 12 freewheels when the hollow shaft 11 is rotated in the second direction B. In this operation mode, no force transmission from the hollow shaft 11 to the drive shaft 3 is possible.

The second one-way clutch 13 is configured for coupling the hollow shaft 11 with the rotary motion generator 2, 4, 5, particularly with a first cogwheel 2 of the rotary motion generator 2, 4, 5, to transfer the driving force from the rotating hollow shaft 11 to the rotary motion generator 2, 4, 5 for generating the rotary motion when the hollow shaft 11 is driven in the second direction B. In other words, in this operation mode, force is transmitted from the hollow shaft 11 rotating in direction B via the second one-way clutch 13 to the first cogwheel 2, more precisely to a shaft extension 71 of the first cogwheel 2. In contrast to this, the second one-way clutch 13 freewheels, i.e. does not transmit a force from the rotating hollow shaft 11 to the extension shaft 71 of the first cogwheel 2, when the hollow shaft 11 rotates in the first direction A.

Hence, by simply adjusting the rotation direction of the hollow shaft 11, it is possible for a user to select either the rotary motion mode or the orbital motion mode.

Most specifically, the rotary motion generator 2, 4, 5 comprises the selectively lockable first cogwheel 2. When the mechanism is operated in the rotary motion mode, the first cogwheel 2 is unlocked by correspondingly operating a cogwheel locking element 9. The cogwheel locking element 9 is configured for selectively locking the first cogwheel 2 to a support body 1 (see operation mode shown in FIG. 1) or for unlocking the first cogwheel 2 to assume the unlocked movably mounted state required for the rotary motion mode (in which the cogwheel locking element 9 is not in engagement with the first cogwheel 2, not shown in the figure). In the rotary motion mode, the cogwheel locking element 9 does not protrude into a corresponding recess in the first cogwheel 2. Therefore, the first cogwheel 2 can freely rotate relative to the support body 1 in the rotary motion mode. The first cogwheel 2 is coupled to the hollow shaft 11 via the second one-way clutch 13 and has a plurality of first cogs (see reference numeral 80 in FIG. 6 to FIG. 9) arranged along an outer circumference of the substantially disk-shaped first cogwheel 2.

A second cogwheel 4, also contributing to the rotary motion generator 2, 4, 5, is arranged on top of the first cogwheel 2 and is mounted in a permanently movably way. Hence, the second cogwheel 4 cannot be fastened in the present embodiment, but can freely follow a rotation motion when a corresponding rotation force is exerted to the second cogwheel 4. The second cogwheel 4 also has a plurality of second cogs arranged along an outer circumference of the second cogwheel 4 (see reference numerals 82 in FIG. 6 to FIG. 9).

Furthermore, a toothed belt 5, also contributing to the rotary motion generator 2, 4, 5, is provided as a deformable but non-elongatable coupling body which encloses or surrounds the entire circumference of both the first cogwheel 2 and the second cogwheel 4. The toothed belt 5 has, as can best be taken from reference numeral 84 in FIG. 6 to FIG. 9, a plurality of third cogs arranged along an inner circumference of the toothed belt 5. The toothed belt 5 is mounted with regard to the first cogwheel 2 and with regard to the second cogwheel 4 so as to engage, in each state during the rotation, a corresponding part of the first cogs 80 and a corresponding part of the second cogs 82 by a corresponding part of the third cogs 84.

In this way, the rotary motion of the second cogwheel 4 and of the sample holder 14, 40 (rigidly connected to the second cogwheel 4 by fastening elements such as screws 73) is generated when the hollow shaft 11 is rotated in the second direction B. This transmits force from the hollow shaft 11 via the second one-way clutch 13 to the first cogwheel 2, and from the first cogwheel 2 via the toothed belt 5 to the second cogwheel 4 and from the second cogwheel 4 to the sample holder 14, 40.

For centrifugation by the rotary motion, the locking device 10 connects drive shaft 3 with the support body 1, whereas locking device 9 is not in engagement with the first cogwheel 33. Via a rotary drive (direct drive or transmission by means of gears) a rotation of the hollow shaft 11 in direction B is generated. The introduced torque is transmitted at the exterior diameter of the hollow shaft 11 via the second one-way clutch 13 locking in this direction onto the cogwheel 2. The first one-way clutch 12 does not transmit any torque in this rotation direction B and freewheels. Via the toothed belt 5, the torque is transmitted towards the second cogwheel 4 which is thereby brought into rotation. By means of drive shaft 3, locked by means of locking device 10, a defined alignment of the drive shaft 3 is achieved during centrifugation, on the other hand the equilibration mass or compensation weight 7 fastened to the drive shaft 3 is prevented from rotating (by bearing friction).

The orbital motion generator 2 to 5 is formed by the first cogwheel 2, the second cogwheel 4, the toothed belt 5 and additionally drive shaft 3. For executing the orbital motion mode, the first cogwheel 2 needs to be brought into a locked stationary mounted state as shown in FIG. 1. This is performed by the cogwheel locking element 9, which is embodied as some kind of displaceable pin, which is brought in engagement with a recess in the first cogwheel 2 as shown in FIG. 1 so that the first cogwheel 2 is stationary locked to the support body 1 as a result of the form closure with the cogwheel locking element 9.

As can furthermore be taken from FIG. 1, the first cogwheel 2 has a central first through hole 30. Also the second cogwheel 4 has a central second through hole 32. The above mentioned drive shaft 3 is guided through the first through hole 30 and is guided through the second through hole 32 and is coupled to the hollow shaft 11 via the first one-way clutch 12. The drive shaft 4 is constituted by different sections including a concentric first section 34 and an eccentric second section 36 (eccentricity r0). The first section 34 is guided through the first through hole 30, whereas the second section 36 is guided through the second through hole 32.

The toothed belt 5 is mounted with the first cogwheel 2 and with the second cogwheel 4 so as to engage part of the first cogs 80 and part of the second cogs 82 by part of the third cogs 84 also in the orbital motion mode to thereby generate the orbital motion of the second cogwheel 4 and the sample holder 14, 40 upon rotating the hollow shaft 11 in the first direction A. Again, the sample holder 14, 40 follows motion of the second cogwheel 4 since it is permanently fastened to the second cogwheel 4 by means of the fastening elements, in the shown embodiment the screws 73. This transmits force from the hollow shaft 11 via the first one-way clutch 12 to the drive shaft 3, and from the drive shaft 3 to the second cogwheel 4 and from the second cogwheel 4 to the sample holder 14, 40. The weak coupling between movable cogwheel 4 and fixed cogwheel 2 mediated via toothed belt 5 provides for two superposed rotation motions of the cogwheel 4, i.e. an orbital motion.

In the orbital motion mode, a coupling force resulting from the form closure of the toothed belt 5 with both the first cogwheel 2 and the second cogwheel 4 is larger than a friction force between contacting surfaces of the first cogwheel 2 and the second cogwheel 4. Hence, the toothed belt 5 is mounted with the first cogwheel 2 and with the second cogwheel 4 so as to form a form closure which superposes, to a rotating motion of the second cogwheel 4 transmitted by the drive shaft 3, a rolling motion of the second cogwheel 4 during which the second cogwheel 4 rolls up on the toothed belt 5 limited by a rolling motion during which the toothed belt 5 rolls up on the first cogwheel 2.

FIG. 1 also shows a non-rotationally symmetric compensation weight 7 (for instance shaped as a half disc) which is mounted asymmetrically on the drive shaft 3 and is configured to compensate for a mechanical load acting on the drive shaft 3 upon generating the orbital motion. The equilibration mass or compensation weight 7 is used for balancing out unbalanced masses. The compensation weight 7 is used for the shaking operation mode only, but not for centrifuging, because in the centrifuging mode the opposing sample holder sections automatically balances out the effects of uncompensated weights.

For mixing in the orbital motion mode, the locking device 9 connects cogwheel 2 with the support body 1, whereas locking device 10 is out of engagement with drive shaft 3. Via a rotary drive (direct drive or transmission by means of an additional gear) a rotation of the hollow shaft 11 in direction A is generated. The introduced torque is transmitted at an inner diameter of the hollow shaft 11 via one-way clutch 12 locking in this direction onto the drive shaft 3 with the eccentric section 36, which also rotates in direction A. The second one-way clutch 13 which is fastened to the cogwheel 2 transmits no torque in this direction and freewheels. In view of the toothed belt 5 being always in engagement, an orientation fixed orbital motion results at the shaking shelf board or sample holder 14. By the co-rotating equilibration or compensation weight 7, an unbalanced mass is at least partially compensated.

Thus, by the mere definition of the rotation direction (A or B) of the hollow shaft 11 powered by a not shown drive unit such as an electric motor, the complementary arrangement of the one-way clutches 12 and 13 ensures that at each time either the orbital motion mode or the rotary motion mode is activated. The apparatus 50 provides for a mechanism for generating an orientation fixed orbital movement when the drive shaft 3 is driven. In contrast to this, a centrifugation motion (rotation) can be activated by changing the rotation direction of the hollow shaft 11 by merely inverting the rotation direction of the drive unit powering the hollow shaft 11. Therefore, a single apparatus 50 is sufficient for providing both an orbital motion for shaking the fluidic sample 38 or a rotary motion for centrifuging the fluidic sample 38. Thus, the apparatus 50 provides for both, a gentle mixing of a sensitive biological sample 38 with an orbital motion, and an efficient separation of different fractions of the biological sample 38 by centrifugation. For adjusting a respective operation mode, a user merely has to adjust the rotation direction of the drive unit for driving the hollow shaft 11. The mechanism for generating the shaking motion along an orbital trajectory can be realized by the two cooperating cogwheels 2, 4 driven by drive shaft 3, wherein the cogwheels 2, 4 are weakly coupled by the toothed belt 5. By additionally providing the one-way clutches 12, 13 freewheeling into two opposite directions and therefore also blocking into opposite directions, the shaking function can be integrated in the same apparatus 50 as a centrifugation function. Thus, the operation of two separate devices is avoided and a sample transfer procedure to be performed by a user or an automatic handling device can be omitted.

The actual drive unit (not shown) such as an electric motor can be aligned with the axis of the drive shaft 3. However, it is alternatively possible to arrange the drive unit laterally displaced with regard to the drive shaft 3, for instance by transmitting the drive force of the drive unit via a force transmission belt or the like to the drive shaft 3. Such a lateral geometry may result in a low height of the apparatus 50.

FIG. 1 furthermore shows that an optional shaft locking element 10 can be provided which can also be embodied as a displaceable locking pin which can either be brought, for the rotary motion mode, in engagement with the drive shaft 3 for selective locking of the drive shaft 3 to the support body 1 (as shown in FIG. 1), or which can be brought, for the orbital motion mode, in a non-engaging state for unlocking the drive shaft 3 with respect to the support body 1.

As alternatives to the hollow shaft 11, another gear element such as a cylinder or a pin or shank may be implemented as well.

With regard to the cogwheel system, both cogwheels 2, 4 may have the same number of cogs or teeth. The eccentricity r0 of the drive shaft 3, i.e. the axis distance of shaft section 36 with regard to the rotation axis 49, can be a multiple integer of the distance of adjacent cogs or teeth on the circumferences of the cogwheels 2, 4. Some deviation from an integer value may be possible so as to provide for some clearance as well. The toothed belt 5 with the interior toothing may have a slightly larger inner diameter (for instance larger by about the eccentricity r0) as compared to the outer diameter of each of the cogwheels 2, 4. Then, the desired weak coupling between the two cogwheels 2, 4 can be mediated via the toothed belt 5.

Drive shaft 3 has its eccentric section 36 being eccentric with regard to rotation axis 49 around which the gear element 11 is rotatable when driven by the drive unit 42. The eccentric section 36 extends through recessed sample holder plate 14 of the sample holder 14, 40. The drive shaft 3 further has its concentric section 34 concentric with regard to the rotation axis 49, wherein the concentric section 34, but not the eccentric section 36, is surrounded by the one-way clutches 12, 13. The concentric section 34 forms a bottom part of the drive shaft 3 and the eccentric section 36 forms a top part of the drive shaft 3. The drive shaft 3 bridges and extends over the entire range from the drive unit 42 to the sample holder 14, 40.

Figure 2:
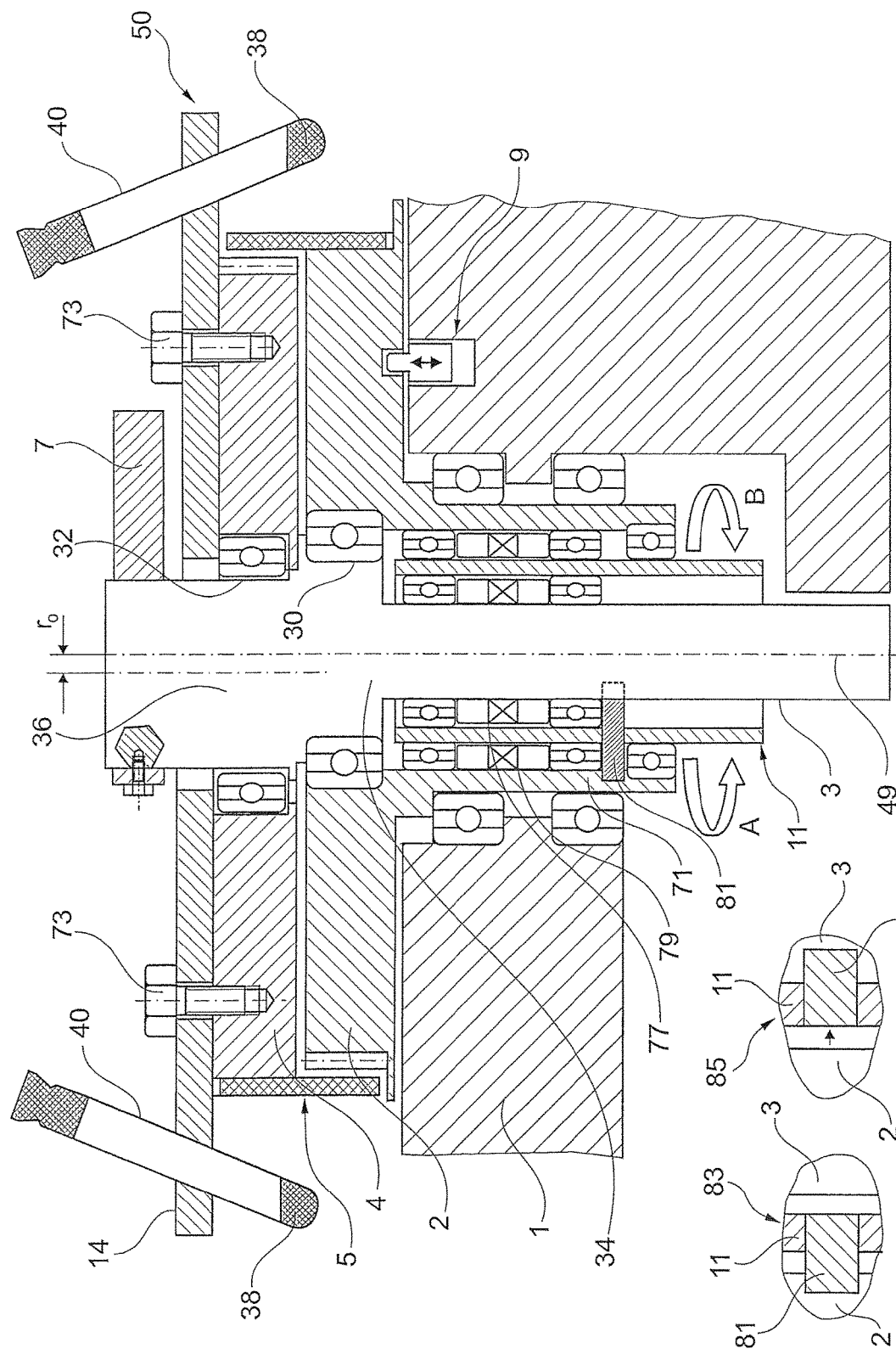
FIG. 2 shows a sample handling apparatus, which may be implemented in a sample processing arrangement according to another exemplary embodiment of the invention, for selectively operating a sample holder accommodating fluidic samples in an orbital motion mode for shaking or in a rotary motion mode for centrifuging.

FIG. 2 illustrates an apparatus 50 according to another exemplary embodiment of the invention.

In the embodiment of FIG. 2, the two one-way clutches 12, 13 are substituted by bearings 77, 79. Both bearings 77, 79 couple the hollow shaft 11 to the first cogwheel 2 and to the drive shaft 3 so that no force is transmitted via these freewheeling bearings 77, 79. In other words, the bearings 77, 79 freewheel in both opposing directions.

In the shown embodiment, the one-way clutch arrangement is realized by a one-way clutch pin 81 cooperating with the freewheeling bearings 77, 79. As can be taken from a detail shown in FIG. 2, the one-way clutch locking pin 81 can be brought in a first position 83 or in a second position 85. By shifting the pin towards the first position 83, the one-way clutch locking pin 81 rigidly couples the hollow shaft 11 with the first cogwheel 2, while in this operation moment the hollow shaft 11 is continuously freely rotatable relative to the drive shaft 3. In contrast to this, in the operation mode 85, the one-way clutch locking pin 81 has been shifted to the right hand side so that the hollow shaft 11 can freely rotate relative to the first cogwheel 2. In contrast to this, the drive shaft 3 is now rigidly coupled with the hollow shaft 11. In other words, the pin 81 in combination with the bearings 77, 79 freewheeling in both directions provide for the one-way clutch arrangement characteristic.

Furthermore, the optional shaft locking pin 10 is omitted in FIG. 2 but can be foreseen in this embodiment as well. Although not essential, shaft locking pin 10 may be advantageous as well since frictional forces in bearings might otherwise result in a rotation or torsion of the shaft 3. In a low friction or frictionless state, shaft locking pin 10 may be omitted.

Figure 3:
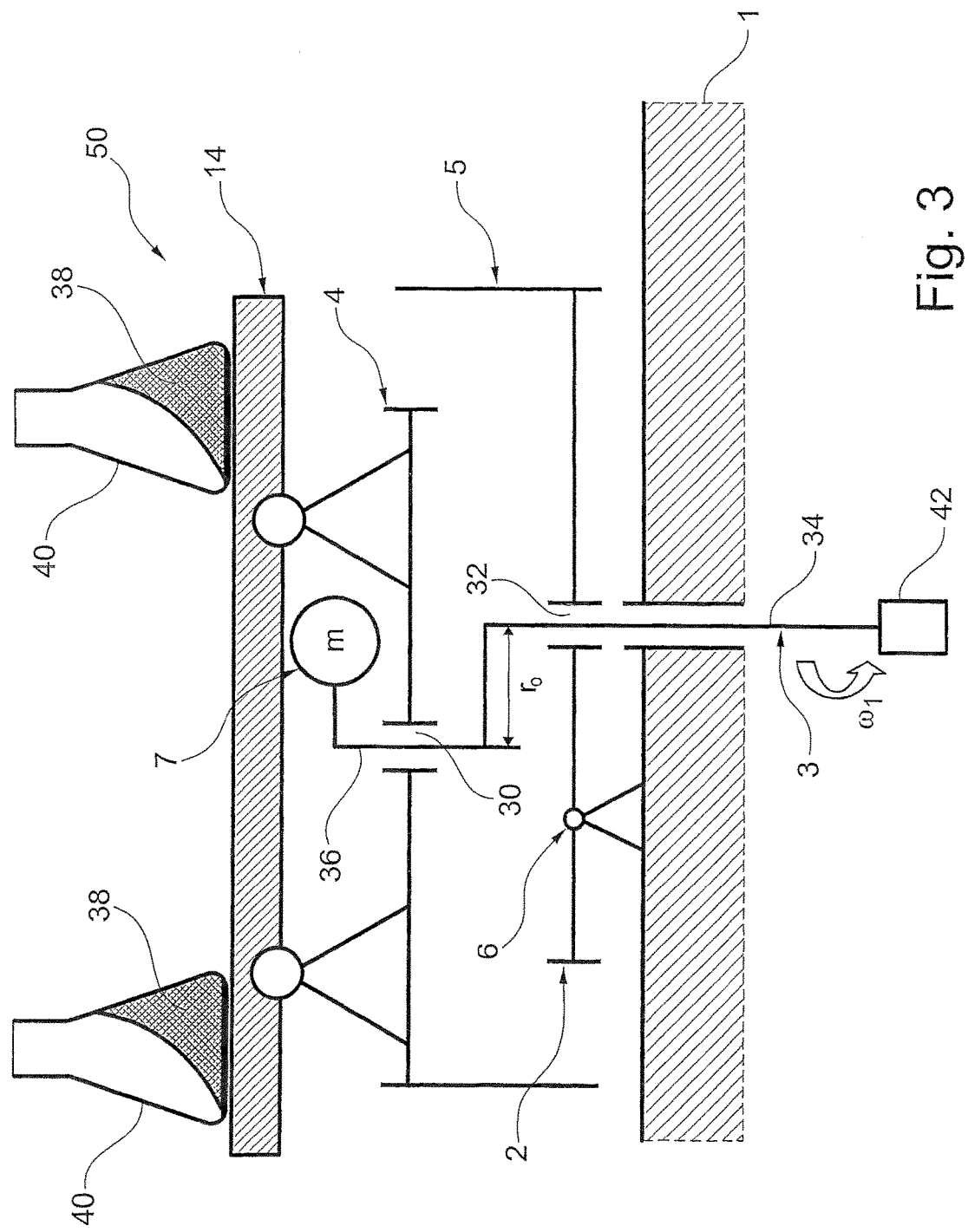
FIG. 3 illustrates schematically a functioning principle of mechanisms and apparatuses according to exemplary embodiments of the invention providing for an orbital motion mode.

FIG. 3 is a schematic illustration of an apparatus 50 according to an exemplary embodiment of the invention.

The mechanism shown in FIG. 3 is constituted by a spatially fixed support body 1, a locked or lockable first cogwheel 2 with a number $z_1$ of cogs or teeth, and a drive shaft 3 having an eccentric cross-section 36 and a concentric cross-section 34. The concentric cross-section 34 is guided through the first cogwheel 2. Further, a rotatably mounted cogwheel 4 with a number of cogs or teeth $z_1$ is mounted on the eccentric cross-section 36 of the drive shaft 3. Toothed belt 5 has a number of cogs or teeth $z_2 > z_1$. On the cogwheel 4, any desired shaking shelf board 14 (for instance for lab containers, vials or well plates) can be fastened. Cogwheel 2 is assembled torque proof on the support body 1 (for instance by fixation 6).

Alternatively, it is also possible that the toothing or cogging of the fixed cogwheel 2 is directly integrated in the support body 1. Cogwheel 2 and support body 1 then form a common integral member.

When using a toothed belt 5, its shape always deviates from a circular cross-section (x≠y in FIG. 5) due to the eccentricity r0. In another embodiment it is also possible that an interior toothed or cogged cogwheel (particularly from plastic material) is used rather than a toothed belt, so that in this scenario it is also possible that the condition x=y applies.

In order to at least partially equilibrate unbalanced masses, it is possible to provide the equilibration mass 7.

As an alternative to the arrangement of toothed belt 5 and cogwheels 2, 4, it is also possible to use two externally toothed and one internally toothed cogwheels, i.e. three cogwheels.

For instance, cogwheel 2 may have z=60 teeth or cogs, and cogwheel 4 may have z=60 teeth or cogs. The toothed belt 5 may for instance have z=62 teeth or cogs. The tooth pitch p may be characterized by p=2 mm, and the eccentricity or the orbital radius r0 may be 2.0 mm (in practice, the value of the eccentricity may vary, for instance may be 1.9 mm or 1.95 mm or 1.85 mm to provide for a slight clearance between the components). For the sake of providing a certain clearance, also for example r0=1.9 mm is possible.

In the scenario FIG. 3, the cogwheel 2 is fixed, and the cogwheel 4 remains orientation fixed during the entire rotation. Toothed belt 5 rotates at each rotation by two teeth or cogs in the rotation direction of the drive shaft 3.

Figure 4:
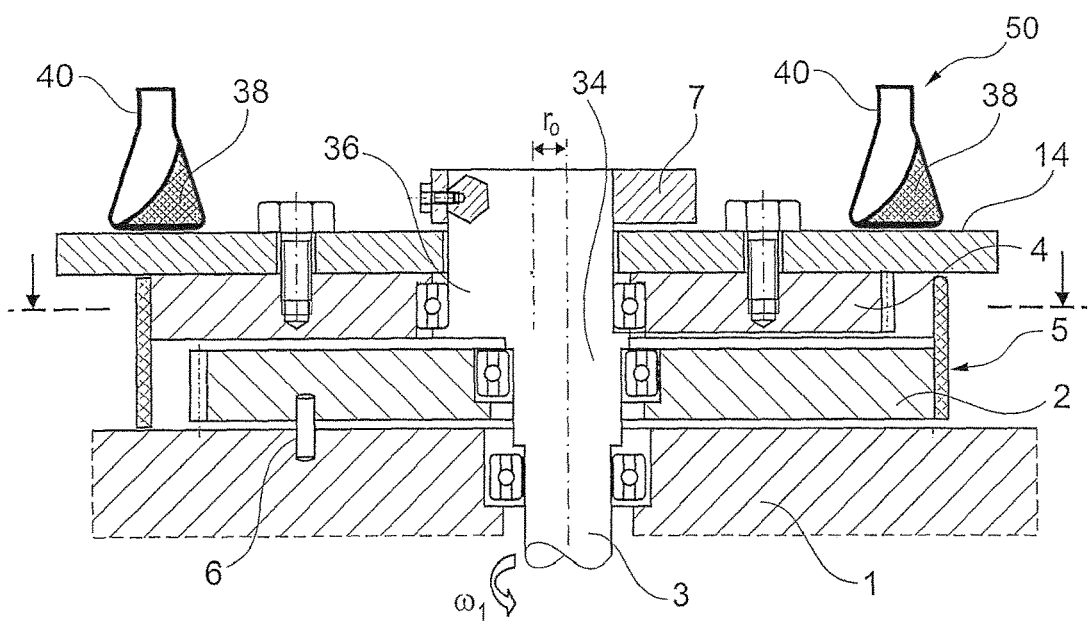
FIG. 4 illustrates part of a sample handling apparatus according to an exemplary embodiment of the invention providing for an orbital motion mode.

FIG. 4 shows a practical realization of an apparatus 50 according to the schematic illustration of FIG. 3.

Figure 5:
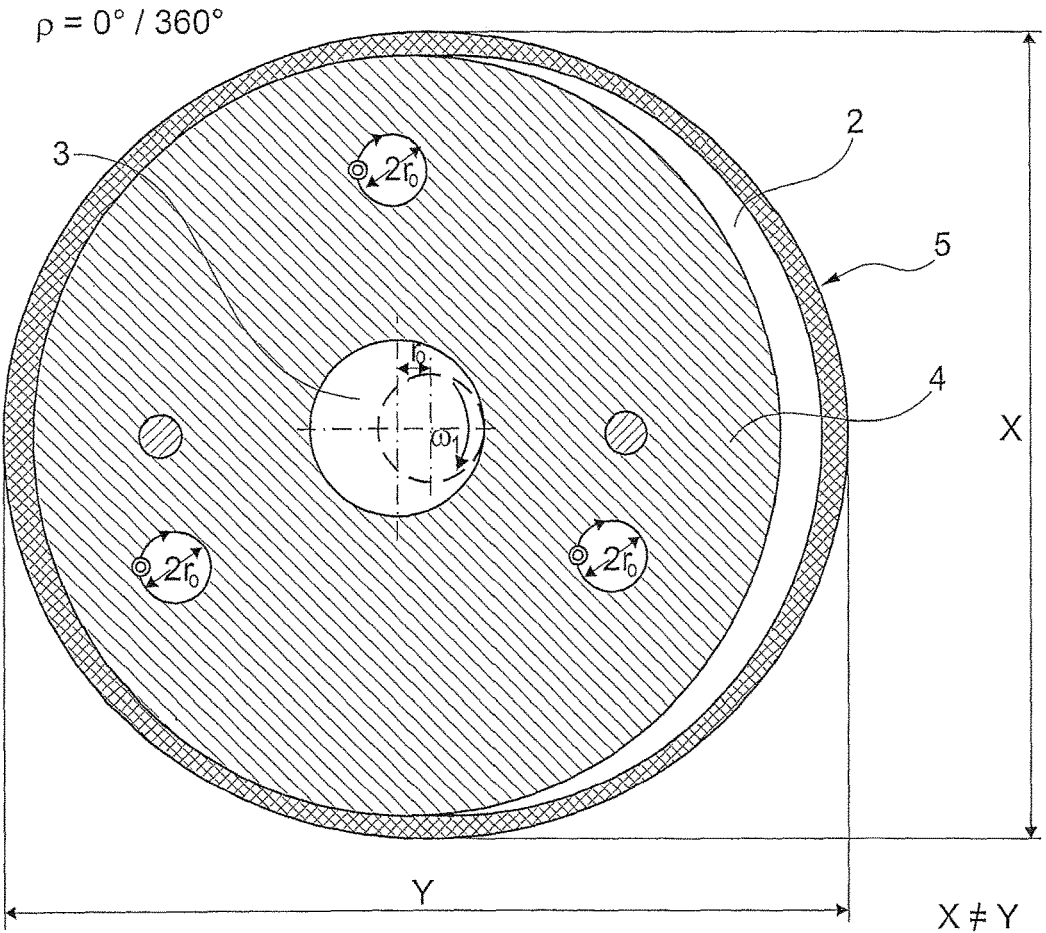
FIG. 5 illustrates cooperation between two cogwheels and a toothed belt according to an exemplary embodiment of the invention. It should be mentioned that the cogs of components are not illustrated in FIG. 5.
Figure 6:
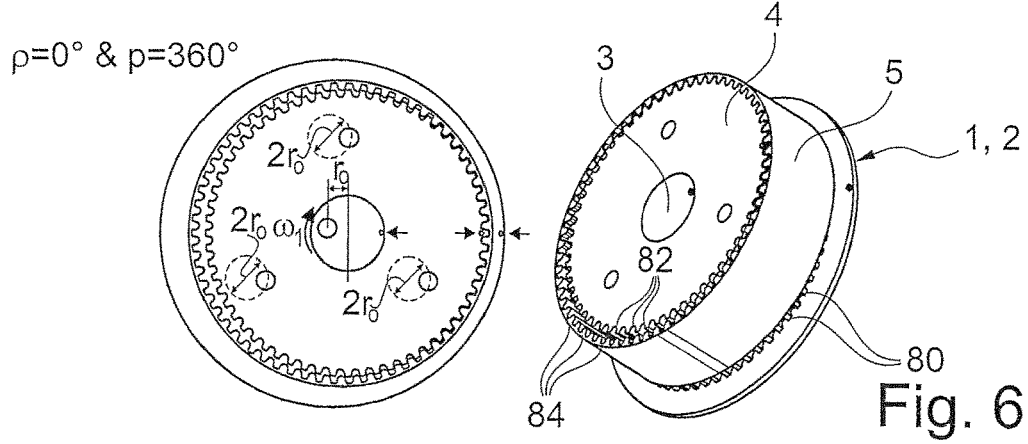
FIG. 6 to FIG. 9 show plan views and cross-sectional views illustrating cooperation between two cogwheels and a toothed belt in different angular states according to an exemplary embodiment of the invention.
Figure 7:
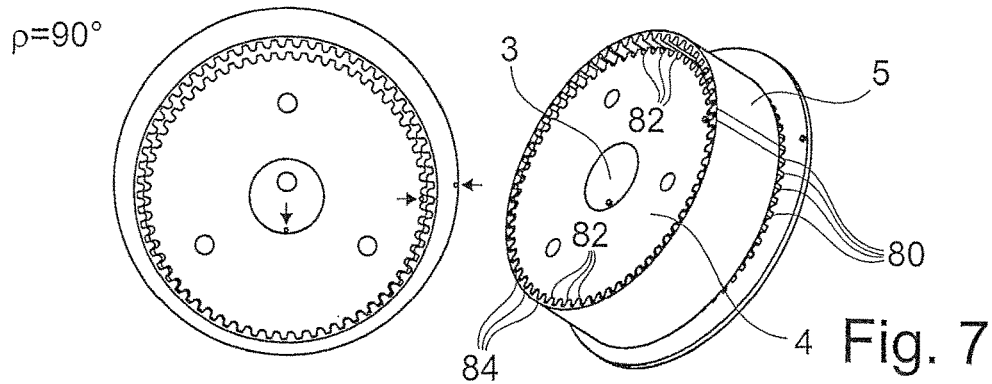
Figure 8:
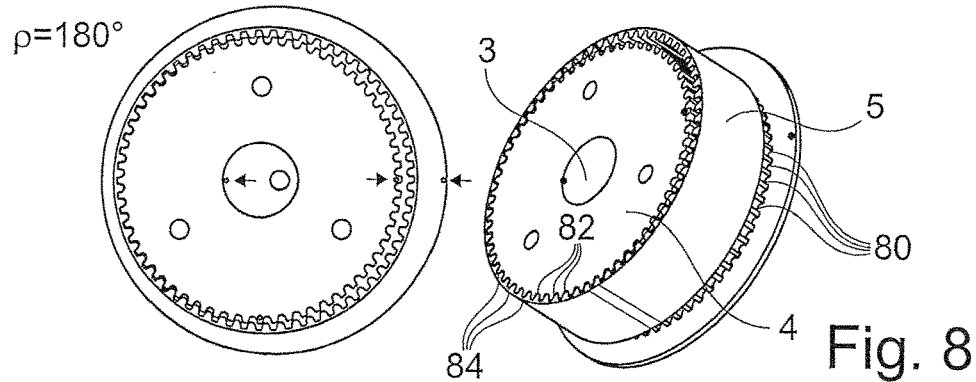
Figure 9:
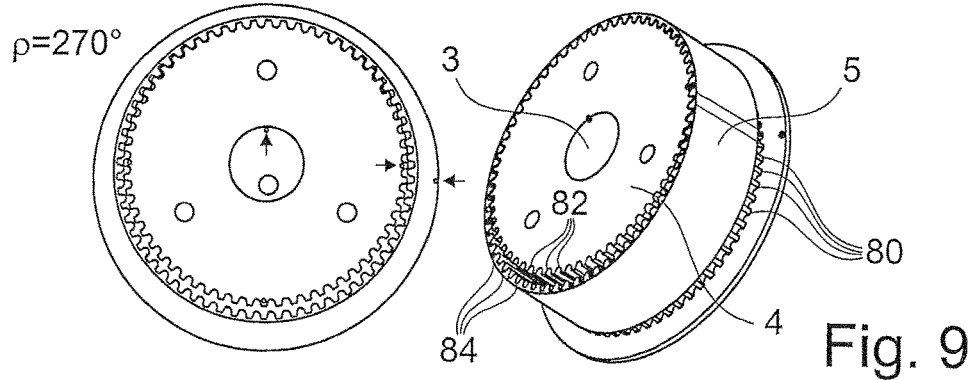

FIG. 5 shows a plan view of the cogwheels 2, 4 and of the toothed belt 5 as well as of the drive shaft 3. It should be mentioned that the cogs of components 2, 4, and 5 are not illustrated in FIG. 5.

FIG. 6 to FIG. 9 shows the relative orientation and cooperation of the cogwheels 2, 4 and the toothed belt 5 during an entire rotation. In this illustration, the spatially fixed support body 1 corresponds to the cogwheel 2. The interaction between the cogs 80, 82 and 84 can be retraced based on FIG. 6 to FIG. 9.

In the following, referring to FIG. 10 to FIG. 16, an apparatus 50 according to an exemplary embodiment of the invention will be explained. This apparatus 50 is compact in size and combines an orbital shaker with a centrifuge, for up to four sample containers (for instance Eppendorf Safelock 2.0 mm).

Apparatus 50 comprises the support body 1, a lid 45 and a rotor 89, see FIG. 10 and FIG. 11. The lid 45 is detachably connectable to the support body 1 by pairs of permanent magnets. Advantageously, it is possible to further increase the safety of the user by a mechanical locking element (for instance a bayonet closure). At the support body 1, a turning knob 91 for a user-defined adjustment of the revolution speed of the apparatus 50 is provided. Each of four accommodation sections 90, 92, 94, 96 is capable of accommodating a respective sample container.

In the following, an operation mode of using the apparatus 50 for an orbital motion (mixture of a fluidic sample) will be explained. The lid 45 is detached from the support body 1, see FIG. 11. In an edge of the support body 1, a Hall switch 93 is provided, see FIG. 12. In another edge, a locking device 95 is provided, which is shifted upwardly by a pair of permanent magnets 97. By this mechanism, disk 99 is connected to the support body 1.

Figure 14:
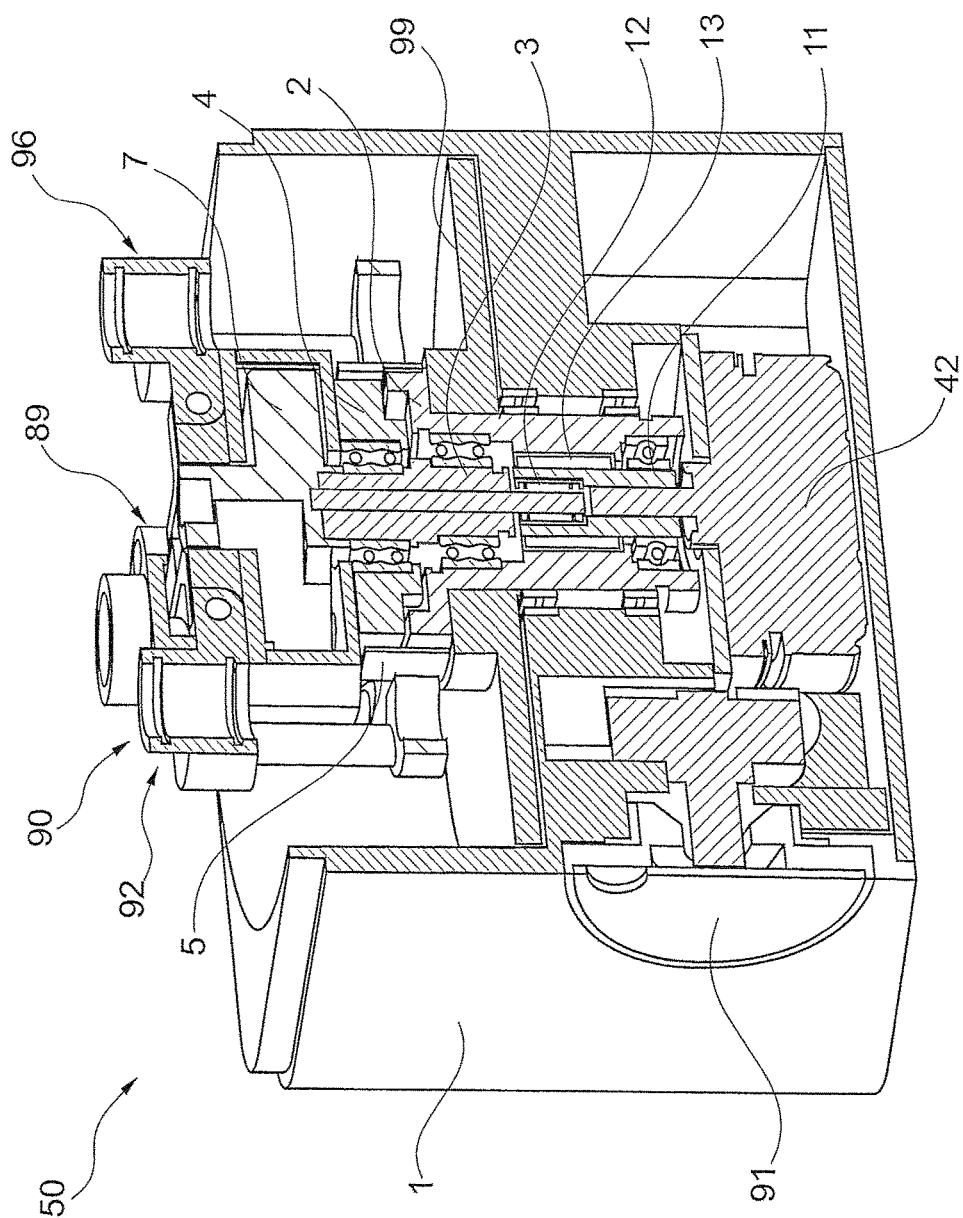
FIG. 14 is a cross-sectional view of the apparatus of FIG. 10 showing an internal constitution thereof.

The locked disk 99 is fixedly connected (for instance screwed) with the hollow shaft having toothed belt toothing 4, see FIG. 14. A drive engine 42 rotates in one direction. The hollow shaft 11 which is directly connected to the engine shaft has a one-way clutch 12 which transfers a torque onto the drive shaft 3 in this direction. The drive shaft 3 has a concentric cross-section and an eccentric cross-section. The second one-way clutch 13 which is assembled in the hollow shaft 11 freewheels in this direction and does not transfer torque. By the drive shaft 3, cogwheel 4 fastened via a ball bearing on the eccentric cross-section, as well as the equilibration mass 7 are orbitally elongated, wherein the two cogwheels 2, 4 are always connected via toothed belt 5. At the upper cogwheel 4, the rotor 89 is fastened.

For centrifugation, lid 45 is attached to the support body 1, see FIG. 15. One or more permanent magnets 107 integrated in the lid 45 unlock locking device 95 via opposingly (or antiparallel) poled permanent magnets (disk 99 and cogwheel 4 can be rotated with regard to the support body 1), see FIG. 13. Additionally, the equilibration mass 7 and consequently the drive shaft 3 with the eccentric cross-section 36 are connected to the lid 45 and the support body 1 in a torque proof way. As can be seen in FIG. 13 and FIG. 15, a pin 103 protrudes from a top plate 105 of the lid 45 and has an actuator 101 at an end thereof. By means of the actuator 101, a locking of the equilibration mass 7 to the lid 45 may be initiated. Hall switch 93 detects a permanent magnet 107 in the lid 45 and changes the rotation direction of the driving engine 42. Hollow shaft 11 transmits torque via one-way clutch 13 to cogwheel 2. Via the toothed belt 5, the introduced torque is transmitted onto the cogwheel 4 and hence to the rotor 89. One-way clutch 12 freewheels in this direction, i.e. no torque is transmitted to drive shaft 3. Rotor 89 rotates itself and the sample containers therein around its symmetry axis, whereby a centrifugation is started, see FIG. 16.

Figure 17:
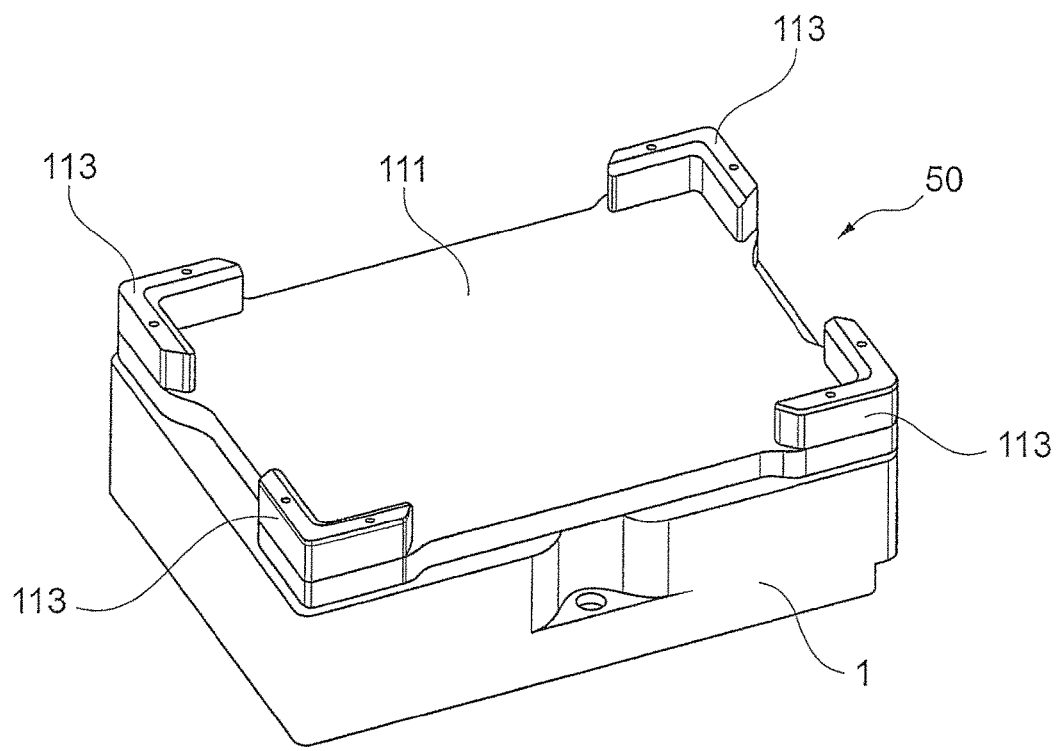
FIG. 17 shows a sample handling apparatus, which may be implemented in a sample processing arrangement according to an exemplary embodiment of the invention, in which well plates are selectively shaken or centrifuged.

FIG. 17 shows an apparatus 50 according to another exemplary embodiment of the invention in which the sample holder is realized by a plate 111 having positioning edges 113 in each of the edges of the apparatus 50 for clampingly engaging a well plate (not shown in FIG. 17) carrying various fluidic samples under examination.

Figure 18:
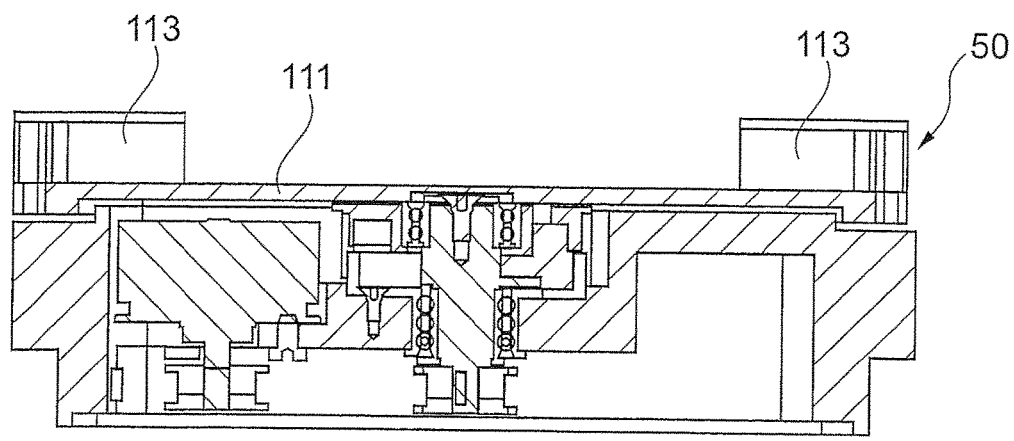
FIG. 18 is a cross-sectional view of the apparatus of FIG. 17 illustrating the internal construction thereof.

FIG. 18 shows a cross-section of the internal constitution of apparatus 50 of FIG. 17. The principles as shown and described above referring to FIG. 1 to FIG. 16 can be implemented here as well.

Figure 19:
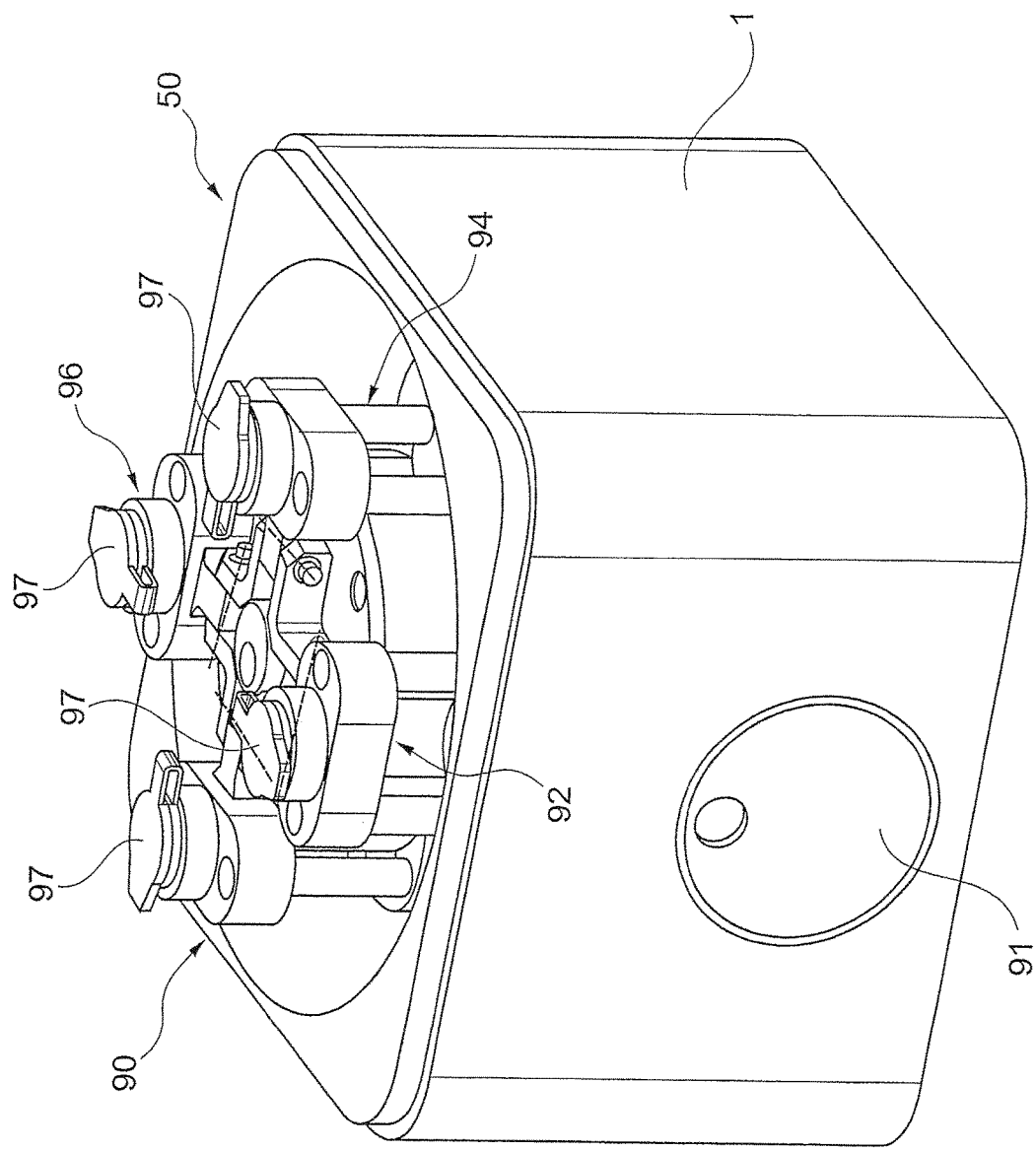
FIG. 19 is a three-dimensional view of an apparatus, which may be implemented in a sample processing arrangement according to an exemplary embodiment of the invention, with removed lid.
Figure 20:
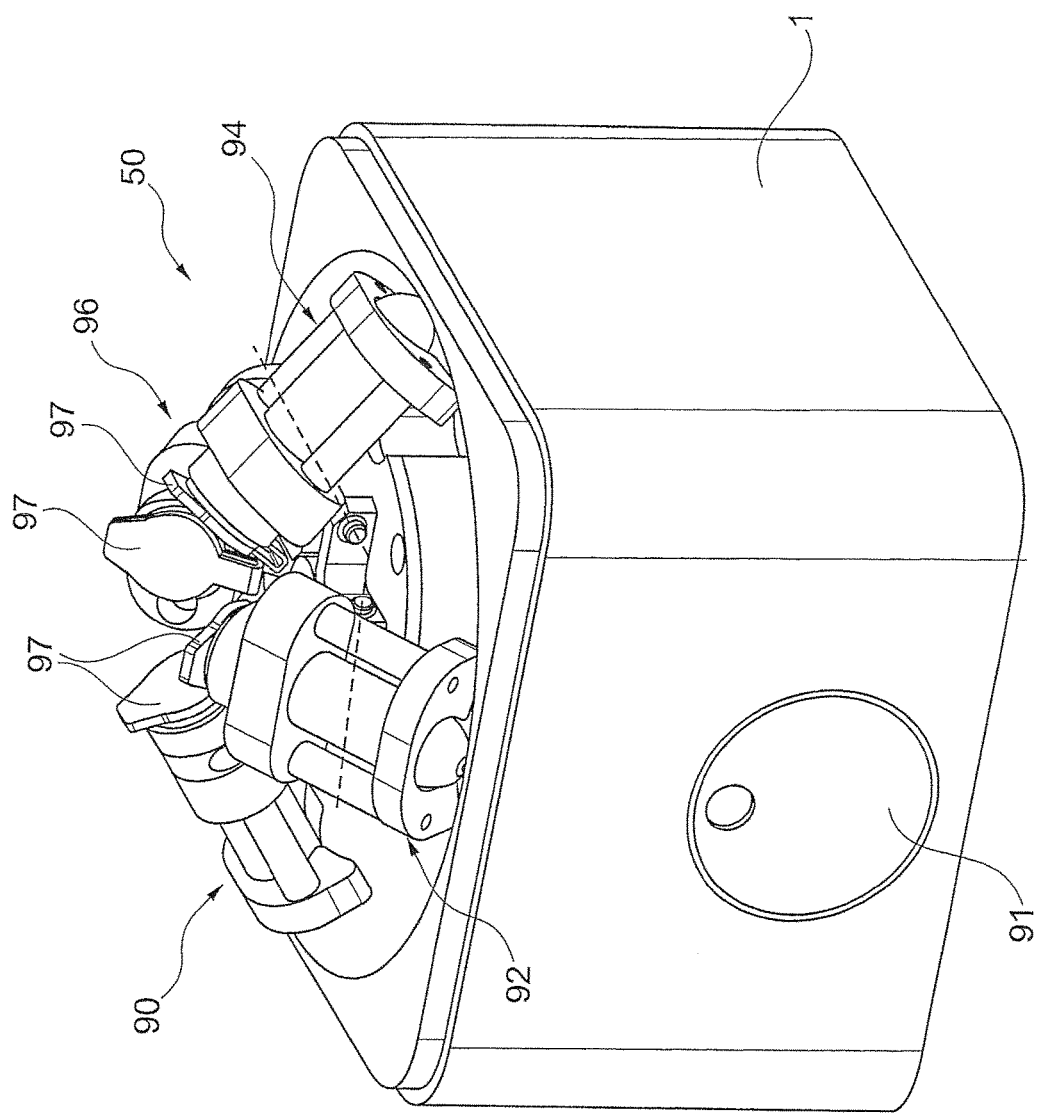
FIG. 20 shows the apparatus of FIG. 19 in an operation mode in which the accommodation sections are pivoted in response to an applied rotational force.

FIG. 19 and FIG. 20 show a further feature of an apparatus 50 according to an exemplary embodiment of the invention. As can be taken from dashed lines in FIG. 19 and FIG. 20, the (in this case four) accommodation sections 90, 92, 94, 96 are mounted to be pivotable around a pivoting axis (dashed sections) which are perpendicular to a vertical rotation axis of the orbital motion and of the rotary motion so as to be pivoted upon exceeding a predefined rotation force. As shown in FIG. 19, when the rotation of the rotor 89 is slow or the mechanism is in orbital motion mode, the centrifugal force acting on the accommodation sections 90, 92, 94, 96 is small as well. However, upon exceeding a predefined threshold value of the centrifugal force, the accommodation sections 90, 92, 94, 96 will move upwardly as shown in FIG. 20 so that the centrifugation can be performed efficiently. Thus, the accommodation sections 90, 92, 94, 96 are foldable and tilt upon exceeding a certain centrifugal force. Optionally, permanent magnets or other biasing force elements may be provided which tend to keep the accommodation sections 90, 92, 94, 96 in the position of FIG. 19 in orbital motion mode.

The vertical alignment of the accommodation sections 90, 92, 94, 96 may be maintained in the orbital motion mode by permanent magnets or resetting elements. In an embodiment, the accommodation sections 90, 92, 94, 96 do not pivot upon mixing, but only upon centrifuging (with a sufficiently high centrifuging force).

Figure 21:
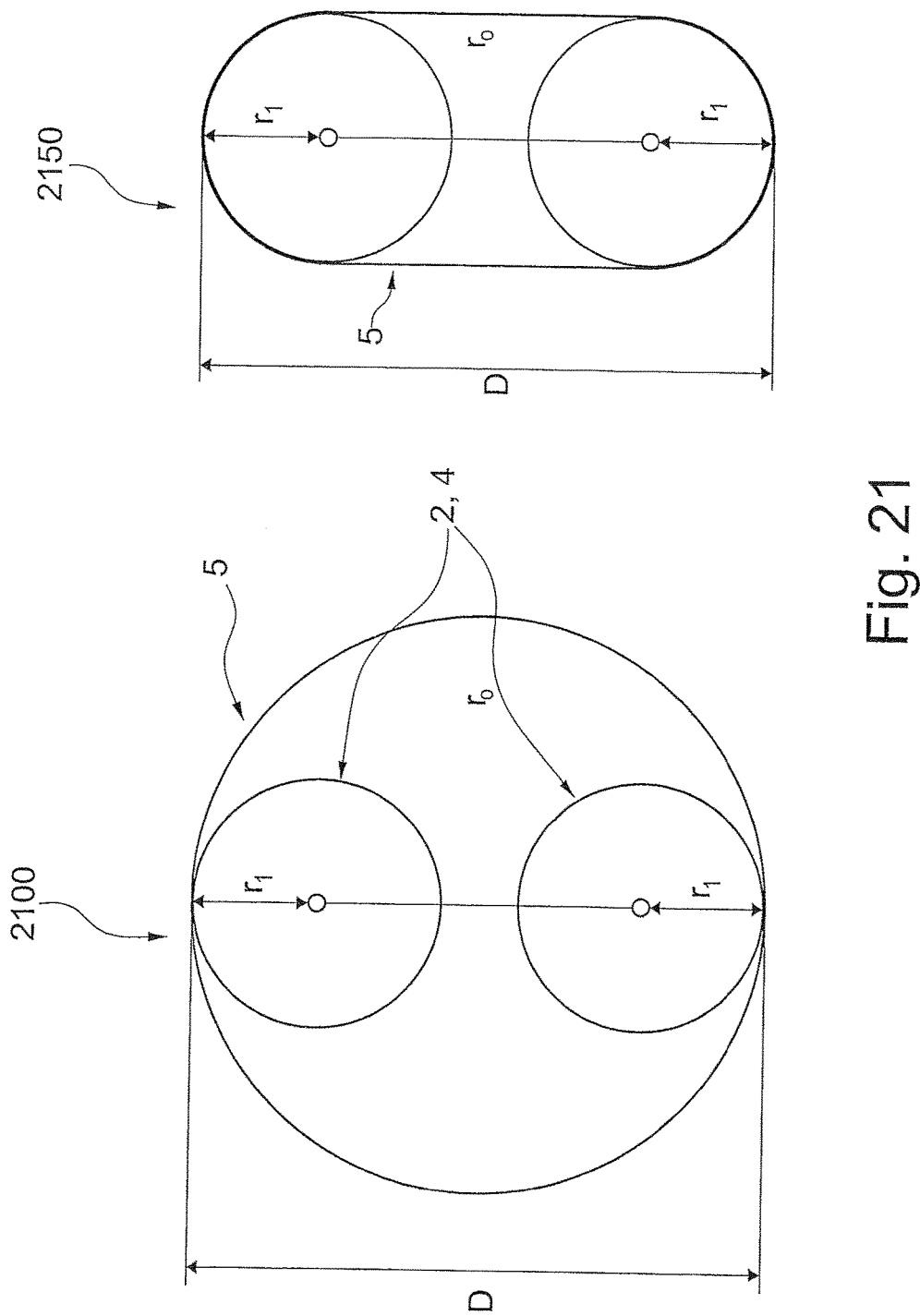
FIG. 21 shows geometrical conditions in a section of a device according to an exemplary embodiment of the invention in which a rigid or a deformable coupling body interacts with two cogwheels.

FIG. 21 shows geometrical conditions in a section of a device according to an exemplary embodiment of the invention in which a rigid coupling body 5 (see left hand side) or a deformable coupling body 5 (see right hand side) interacts with two cogwheels 2, 4.

If the coupling body 5 is a rigid structure (such as an internally toothed pinion or gearwheel) the scenario 2100 is obtained.

If the coupling body 5 is a deformable structure (such as a toothed belt) the scenario 2150 is obtained.

The inner diameter D (or more precisely the largest inner extension) of the coupling body 5 is larger, by the eccentricity $r_0$, than twice of the radius $r_1$ of the cogwheels 2, 4:

$$D = r_1 + r_1 + r_0 = d_1 + r_0$$

Figure 22:
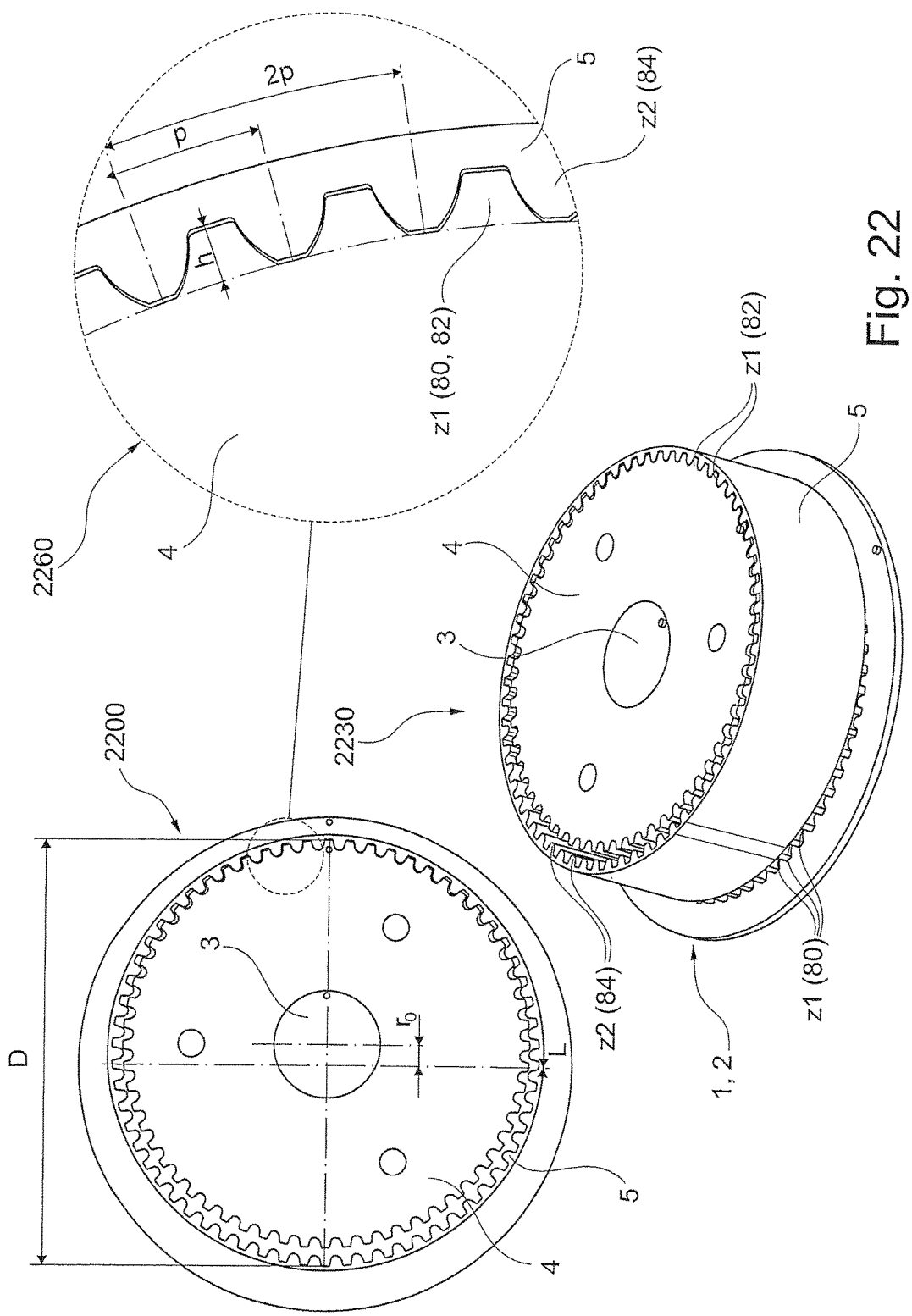
FIG. 22 shows a plan view, a three-dimensional view and a detail of a mechanism illustrating an interaction between a coupling body and two cogwheels according to an exemplary embodiment of the invention.

FIG. 22 shows a plan view 2200, a three-dimensional view 2230 and a detail 2260 of a mechanism illustrating an interaction between coupling body 5 and two cogwheels 2, 4 according to an exemplary embodiment of the invention.

For a proper orbital motion, the following conditions should be fulfilled:

a) Inner diameter D (in case of a rigid coupling body 5) or largest extension (in case of a deformable coupling body 5) of the coupling body 5 should ideally be the sum of the outer diameter of one of the cogwheels 2, 4 ($d_1 = r_1 + r_1$) plus the eccentricity $r_0$, i.e. $D = r_1 + r_1 + r_0 = d_1 + r_0$.

b) The number $z_2$ of teeth of the coupling body 5 should be larger, by at least one tooth, than the number $z_1$ of teeth of the cogwheels 2, 4: $z_2 > z_1 + 1$ c) The eccentricity $r_0$ should be larger than the height h of the teeth (in order to enable a decoupling of the teeth from the coupling body 5): $r_0 > h$ d) The eccentricity $r_0$ should be selected so that the number $z_2$ of teeth of the coupling body 5 is integer (plus some clearance, as the skilled person will understand): $r_0 = (L - z_1 * p) / 2$, wherein $L = z_2 * p$ is the circumferential length of the coupling body 5 and p is the tooth pitch.

Figure 23:
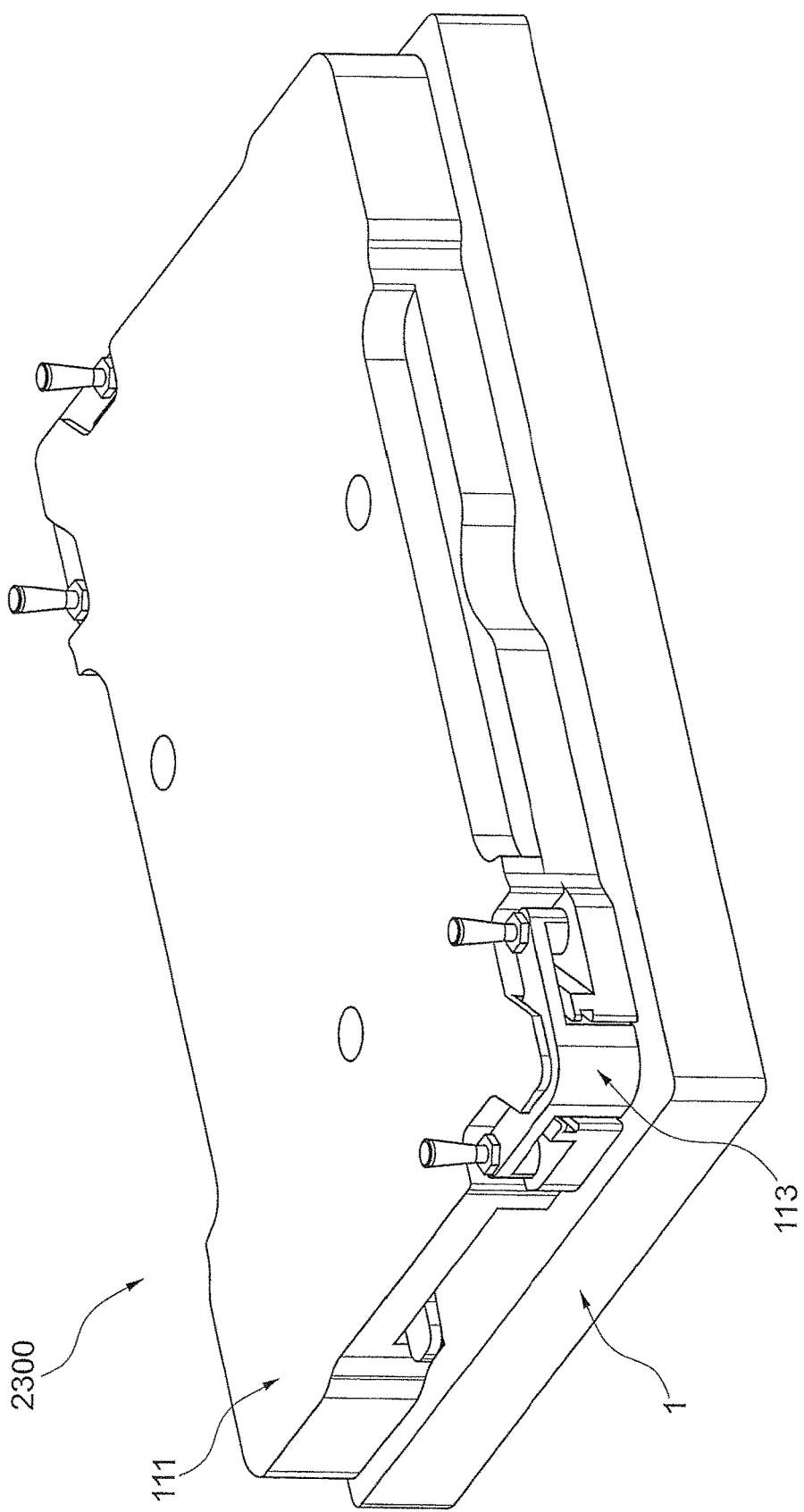
FIG. 23 and FIG. 24 show a sample handling apparatus, which may be implemented in a sample processing arrangement according to an exemplary embodiment of the invention, in which well plates can be shaken.
Figure 24:
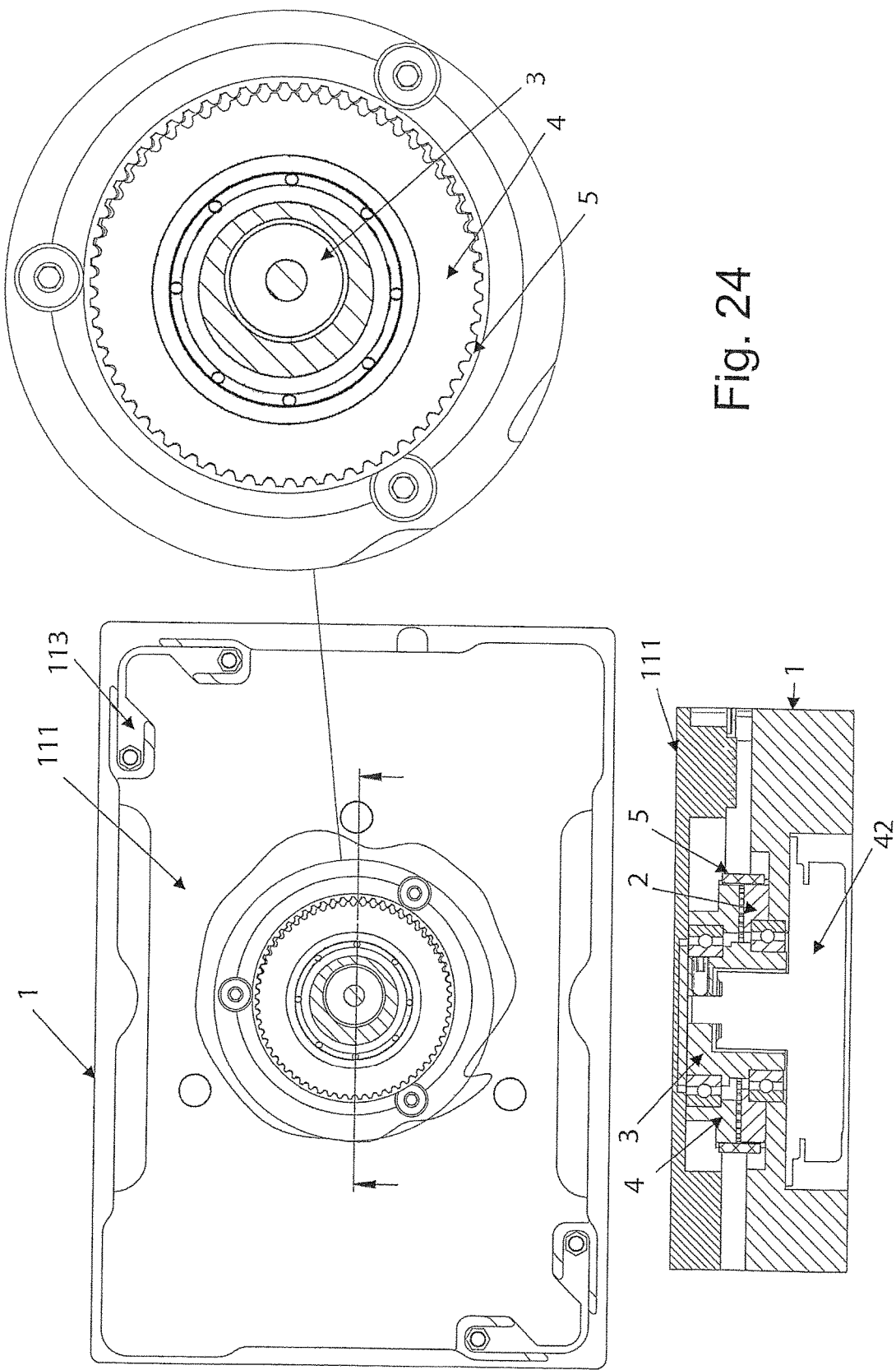

FIG. 23 shows a plan view and FIG. 24 shows detailed views of a sample handling apparatus 2300 according to an exemplary embodiment of the invention in which well plates (not shown) can be shaken.

The functionality of the sample handling apparatus 2300 equals to that of the embodiment of FIG. 17, i.e. it is an orbital shaker with a flat construction for handling well plates. The shown embodiment has implemented the function "shaking by orbital motion". In contrast to the embodiment of FIG. 17, the embodiment of FIG. 23 has a direct driving mechanism for drive shaft 3, wherein FIG. 17 and FIG. 18 implement an indirect drive. Additionally, the positioning edges 113 have an edge locking mechanism (of the type as disclosed in WO 2011/113858). In this embodiment, a compensation weight 7 (not shown) can be advantageously attached on drive shaft 3.

Figure 25:
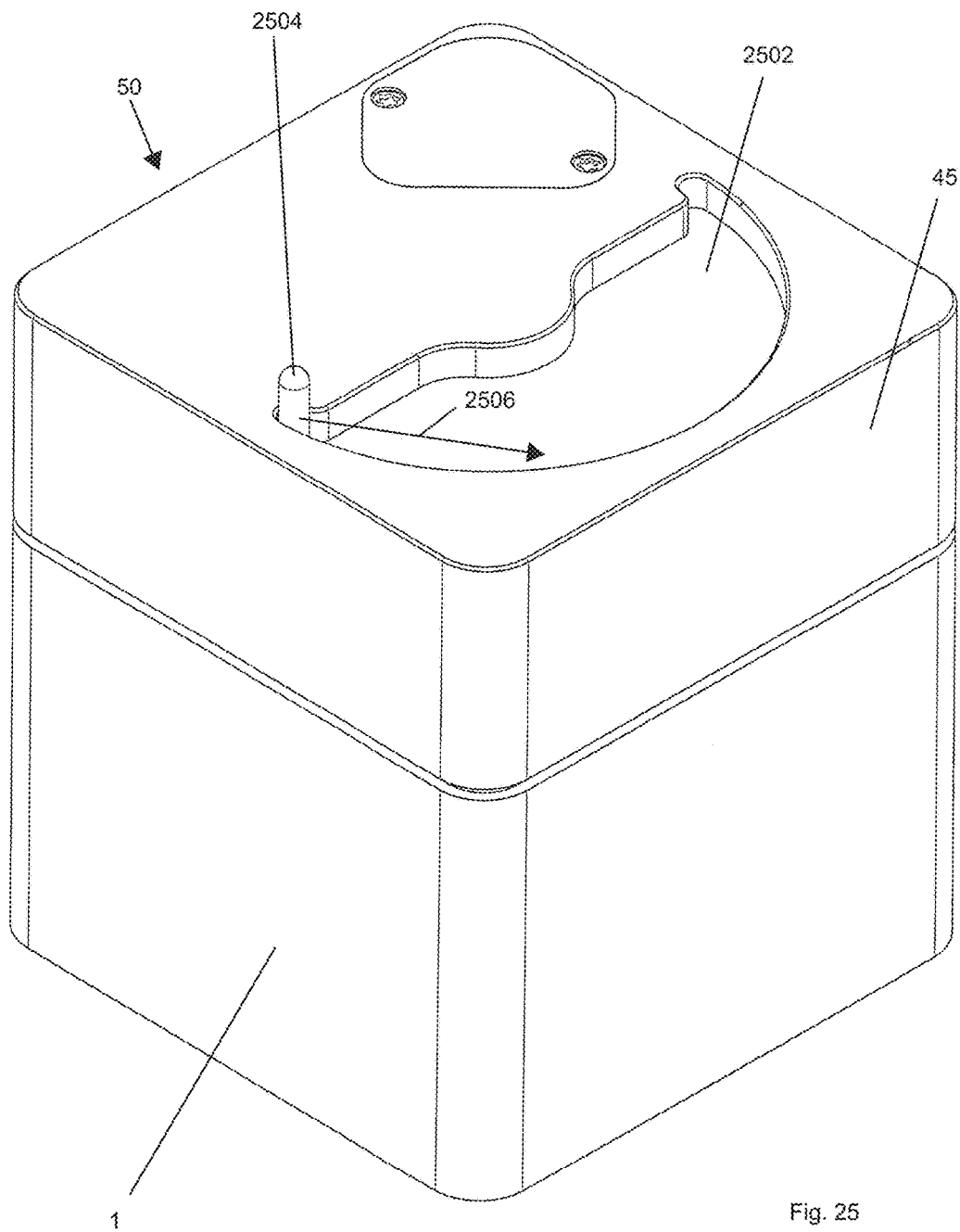
FIG. 25 shows a three-dimensional view of a sample handling apparatus, which may be implemented in a sample processing arrangement according to an exemplary embodiment of the invention.

FIG. 25 shows a three-dimensional view of a sample handling apparatus 50 according to another exemplary embodiment of the invention. Construction of the sample handling apparatus 50 is similar to FIG. 10. The sample handling apparatus 50 has a support body 1 and a removable lid 45. However, the lid has a recess in a top surface thereof which is selectively closable openable by moving a slidable plate 2502. In the shown configuration, plate 2502 covers the recess in lid 45 so that the lid 45 is in a closed state. By operating an actuation pin 2504 along a rotation trajectory 2506, the plate 2502 is slid below the outer surface of the lid 45, thereby exposing an interior of the sample handling apparatus 50 to an external environment. This also allows to handle sample containers in accommodation sections 90, 92, 94, 96.

Figure 26:
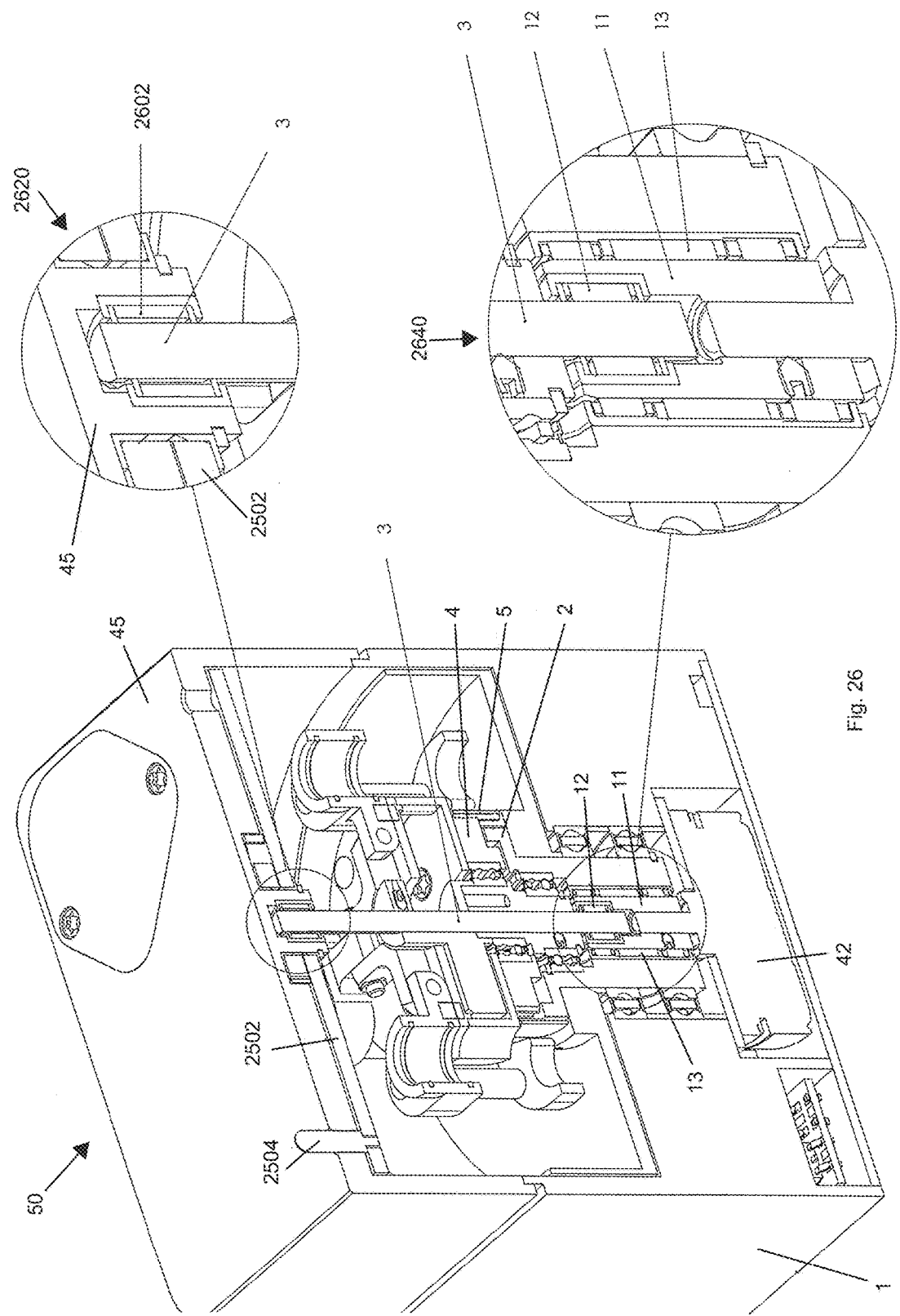
FIG. 26 shows a three dimensional cross-sectional view of the sample handling apparatus of FIG. 25 together with two details illustrating certain features thereof.
Figure 27:
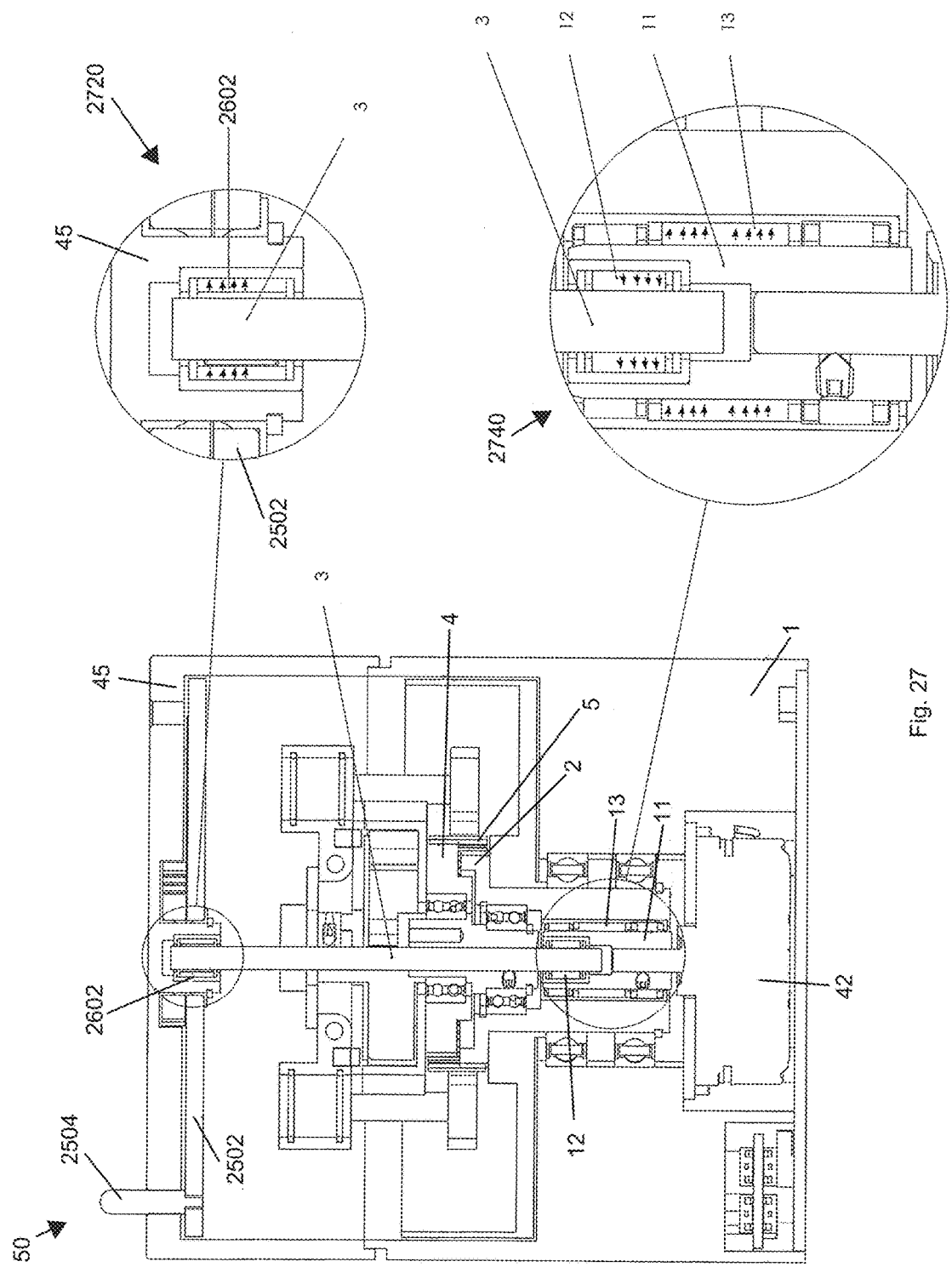
FIG. 27 shows a planar cross-sectional view of the sample handling apparatus of FIG. 25 together with two details illustrating certain features thereof.

FIG. 26 shows a three dimensional cross-sectional view of the sample handling apparatus 50 of FIG. 25 together with two details 2620, 2640 illustrating certain features thereof. FIG. 27 shows a corresponding planar cross-sectional view of the sample handling apparatus 50 together with two details 2720, 2740 illustrating certain features thereof.

In the following, reference is made to the differences of the embodiment of FIG. 26 and FIG. 27 as compared to the embodiments described above. In the embodiment of FIG. 26 and FIG. 27, a shaft locking element 10 is omitted. In contrast to this, the sample handling apparatus 50 further comprises a locking one-way clutch 2602 configured for coupling drive shaft 3 of the orbital motion generator 2 to 5 with lid 45 on support body 1 so as to selectively lock the drive shaft 3 with the lid 45 on the support body 1 to a locked stationarily mounted state when the gear element 11 is driven in direction B (compare FIG. 1), or to freewheel in an unlocked movably mounted state of the drive shaft 3 when the gear element 11 is driven in the other direction A.

As in the above embodiments, the second one-way clutch 13 is arranged to circumferentially surround the first one-way clutch 12. The first one-way clutch 12 and the second one-way clutch 13 are arranged concentrically around a rotation axis of drive shaft 3 of the orbital motion generator 2 to 5. The first one-way clutch 12 and the second one-way clutch 13 are arranged at overlapping height ranges in relation to the rotation axis of the drive shaft 3 of the orbital motion generator 2 to 5. As in the previously described embodiments, the gear element 11 comprises a hollow shaft being located between the first one-way clutch 12 and the second one-way clutch 13 so as to surround the first one-way clutch 12 and to be surrounded by the second one-way clutch 13.

Also in FIG. 25 to FIG. 27, the mechanism comprises cooperating cogwheels 2, 4 forming part of both the orbital motion generator 2 to 5 and the rotary motion generator 2, 4, 5. Drive shaft 3 which is to be coupled to the gear element 11 via the one-way clutch 12 forms part of the orbital motion generator 2 to 5, but not of the rotary motion generator 2, 4, 5.

In contrast to the previously described embodiments, the FIG. 26 and FIG. 27 embodiment omits shaft locking element and implements instead of this a third one-way clutch, i.e. locking one-way clutch 2602. The outer ring of the locking one-way clutch 2602 is connected to the stator housing (here lid 45, alternatively support body 1) of the sample handling apparatus 50 in a rotatably fixed or torque-proof way. Clamping elements of the locking one-way clutch 2602 run on drive shaft 3. By the locking one-way clutch 2602, rotation of the drive shaft 3 is disabled in one direction and is enabled in the opposite direction. In order to enable the locking one-way clutch 2602 to fulfil the function of the shaft locking element 10, locking one-way clutch 2602 freewheels in the same direction as the second one-way clutch 13 and freewheels in the opposite direction than the first one-way clutch 12. An advantage of the shown embodiment in contrast to the provision of shaft locking element 10 is that an automatic (i.e. without the need of an active control) locking and unlocking of the drive shaft 3 with regard to the stator housing is made possible with simple means.

Figure 28:
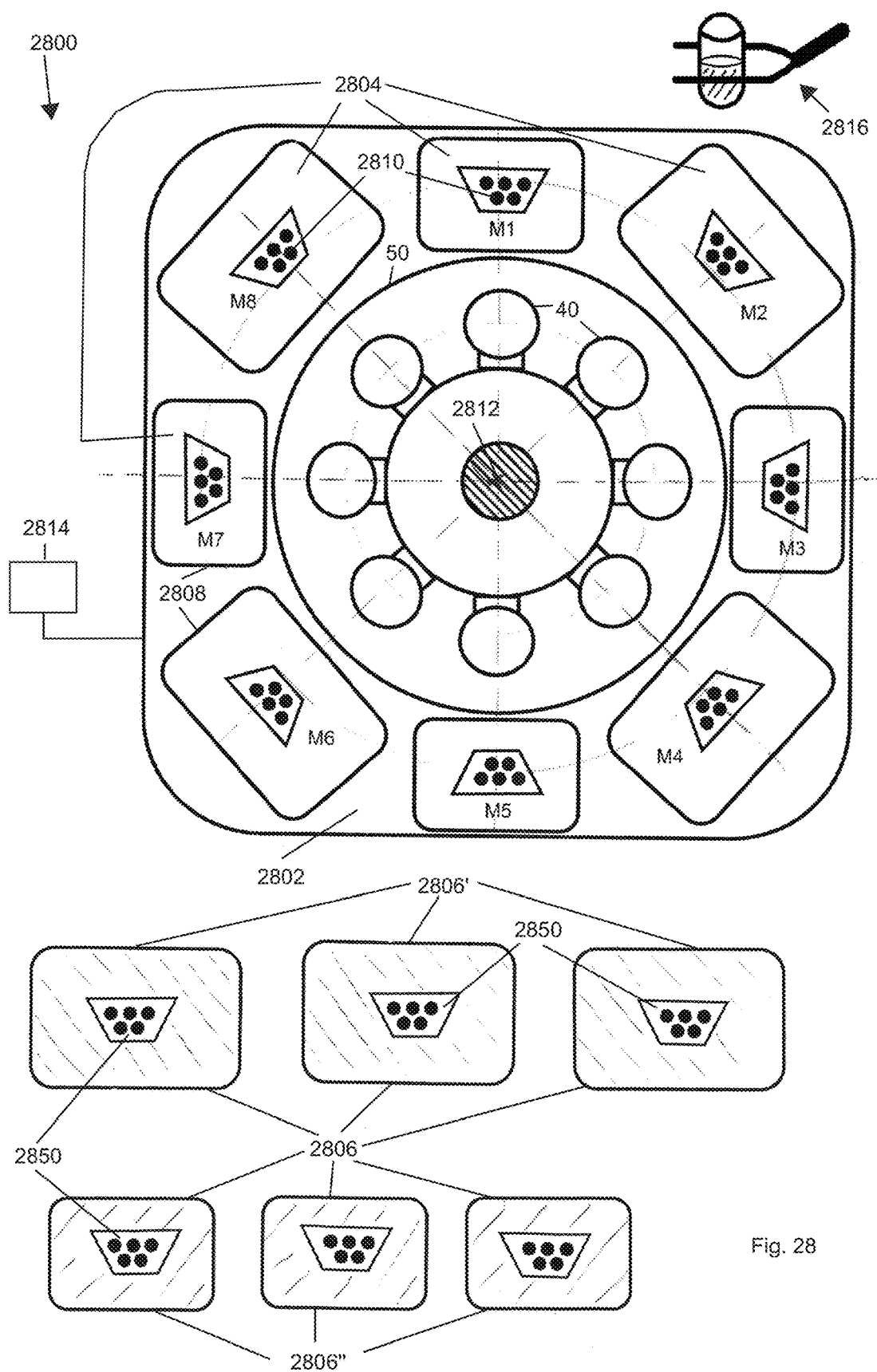
FIG. 28 is a schematic plan view of a sample processing arrangement according to an exemplary embodiment of the invention implementing a mechanism/an apparatus as described referring to the previous figures.

In the following, referring to FIG. 28, a sample processing arrangement 2800 according to an exemplary embodiment of the invention will be explained. FIG. 28 shows the sample processing arrangement 2800 in a plan view.

The sample processing arrangement 2800 comprises a plurality of sample containers 40, here in the form of basically cylindrical tubes being closed at a tapering bottom, each being configured for accommodating a corresponding amount of fluidic sample (for instance in a range between 500 μm to 10 ml). The sample containers 40 are circumferentially distributed, angularly spaced by 45° with regard to the next neighbors, around a rotation axis 2812 of the sample processing arrangement 2800. As an alternative to an angle of 45°, another angle may be implemented which is dependent on the number of container positions within the rotor. The rotation axis 2812 relates to the rotary motion mode of the rotor mechanism illustrated schematically in FIG. 28 which may for instance be implemented as shown in FIG. 1. It is noted that a further rotary axis is arranged slightly displaced but parallel to the rotor axis 2812 and relates to an orbital motion mode. Both the rotor axis 2812 and the slightly parallel shifted other rotor axis (not shown in FIG. 28) extend out of the paper plane of FIG. 28. As indicated by a dashed circle, the sample containers 40 are concentrically arranged around the rotor axis 2812, i.e. each having the same radio distance from the rotor axis 2812.

The rotor mechanism forms part of an apparatus 50 (compare the previously described embodiments) being configured for selectively operating the sample containers 40 either in the orbital motion mode for sample mixing or in the rotary motion mode for sample separation by centrifuging.

Furthermore, a mounting platform 2802 is provided having a support body or a solid basically rectangular ground plate. Other shapes than a rectangular ground plate are possible. A central portion of the mounting platform 2802 around a center of gravity of the ground plate is equipped with the apparatus 50. It is however not necessary that the rotation axis is positioned in a center of gravity of the ground plate. The rotation axis can rather be arranged apart from a center of the ground plate. Moreover, in the shown embodiment eight plug-in positions 2804 are circumferentially distributed in a symmetric way around the rotor axis 2812 in a circumferential portion of the mounting platform 2802. As mentioned above, the rotor with the sample containers 40 mounted thereon can be rotated around rotor axis 2812. In the present state of the sample containers 40, each of the sample containers is spatially aligned with a respective one of the plug-in positions 2804. However, by further rotating the rotor 50 by 45°, each of the sample containers 40 is aligned to another, adjacent one of the plug-in positions 2804. As can be taken from FIG. 28, the arrangement of the plug in positions 2804 is also concentric around the rotor axis 2812. The plug in positions 2804 and the sample containers 40 are furthermore arranged so that when one of the containers 40 is in alignment or in flush with one of the plug-in positions 2804, each other of the sample containers 40 is also in alignment or in flush with a respective other one of the plug-in positions 2804.

FIG. 28 furthermore shows schematically various sample processing modules 2806 which are shown basically as "black boxes" symbolizing blocks which, in view of their not shown interior constitution, are capable of fulfilling certain sample processing tasks. Such processing tasks may include sample pipetting into the fluid containers 40, temperature adjustment of the fluidic samples in the sample containers 40, analysis of reaction products resulting from chemical reactions involving the fluidic sample within the sample containers 40, etc.

The modular configuration of the mounting platform 2802 in combination with the sample processing modules 2806 allows to detachably accommodate a respective sample processing module 2806 in a selectable one of the plug-in positions 2802. As can be taken from FIG. 28, two different kinds of sample processing modules 2806 are provided which differ regarding their form factor, shape and dimension. Thus, a first type of sample processing modules 2806' can be plugged into a first type of plug-in positions 2804 arranged in the four corners of the rectangular plate constituting the mounting platform 2802. A second type of smaller sample processing modules 2806" is to be received in four smaller plug-in positions 2802 arranged along the sides of the rectangular plate constituting the mounting platform 2802. Since only sample processing modules 2806 having a certain form factor can be received in corresponding plug-in positions 2804 having a matching corresponding form factor, erroneous combinations of sample processing modules 2806 and plug-in positions 2804 may be safely prevented.

The shape of a sample processing module 2806 must match to a corresponding counter-shape or inverse shape of a corresponding plug-in position 2804 to establish a mechanical connection. Moreover, as can be taken from FIG. 28, electrical interfaces 2810 are arranged within the plug-in positions 2804. Hence, plugging a respective sample processing module 2806 (having an electric counter-interface, see reference numeral 2850) into a matching plug-in position 2804 will also establish an electrical connection between the sample processing module 2806 and the corresponding plug-in position 2804. Via the matching electrical interfaces 2810, 2850, both an energy supply of the plugged in sample processing module 2806 (which may itself be free of an internal energy supply unit) and/or a data communication between the plugged in sample processing module 2806 and the mounting platform 2802 can be established.

As can be taken from FIG. 28, the centers of the plug-in positions 2804 are arranged positioned along a circumferential surrounding of the rotor axis 2812, concentrically therewith. Therefore, the rotationally symmetric geometry of the rotor is repeated by the circumferential arrangement of the plug-in positions 2804 and, in a mounted state, of the sample processing modules 2806. By taking this measure, the distance between the sample processing modules 2806 and the fluidic samples in the sample containers 40 to be processed using the sample processing modules 2806 is kept very small so that the processing of the fluids by means of the sample processing modules 2806 can be performed rapidly and accurately.

FIG. 28 furthermore shows a control unit 2814 which may be embodied as a microprocessor or a central processing unit (CPU). The control unit 2814 centrally controls operation of the entire sample processing arrangement 2800. Particularly, the control unit 2814 may control operation of the sample processing arrangement 2800 in three different operation modes. A first operation mode is the rotary motion mode for sample separation, for instance by centrifugation. A second operation mode is the orbital motion mode in which the fluidic samples in the sample containers 40 are mixed by an orbital motion. A third operation mode is a sample container alignment mode in which the rotor mechanism is rotated until a defined one of the sample containers 40 is aligned to or faces an assigned one of the sample processing modules 2806. Thus, by a selective rotation of the sample containers 40 around a predefined rotation angle selected specifically to bring a specific sample container 40 in alignment with an assigned sample processing module 2806, any desired processing protocol may be worked off. Thus, one and the same sample in a sample container 40 may be subjected to sample separation, sample mixing and/or sample processing by a selectable one of the plugged in sample processing modules 2806. It is also possible that a specific sample container 40 is brought in the alignment subsequently with different ones of the sample processing modules 2806 to thereby undergo a freely definable sequence of processing steps.

The integrated sample processing arrangement 2800 may be operated in combination with a sample handling robot 2816 which is schematically illustrated in FIG. 28 and can be operated to supply a sample to the sample holder 14 or to sample containers 40 located therein. The sample handling robots 2816 may also remove sample from the sample holder 14 or from sample containers 40. Thus, only sample supply and removal has to be handled by the sample handling robot 2816, whereas all other fluid processing tasks are performed by the integrated sample processing arrangement 2800.

Figure 29:
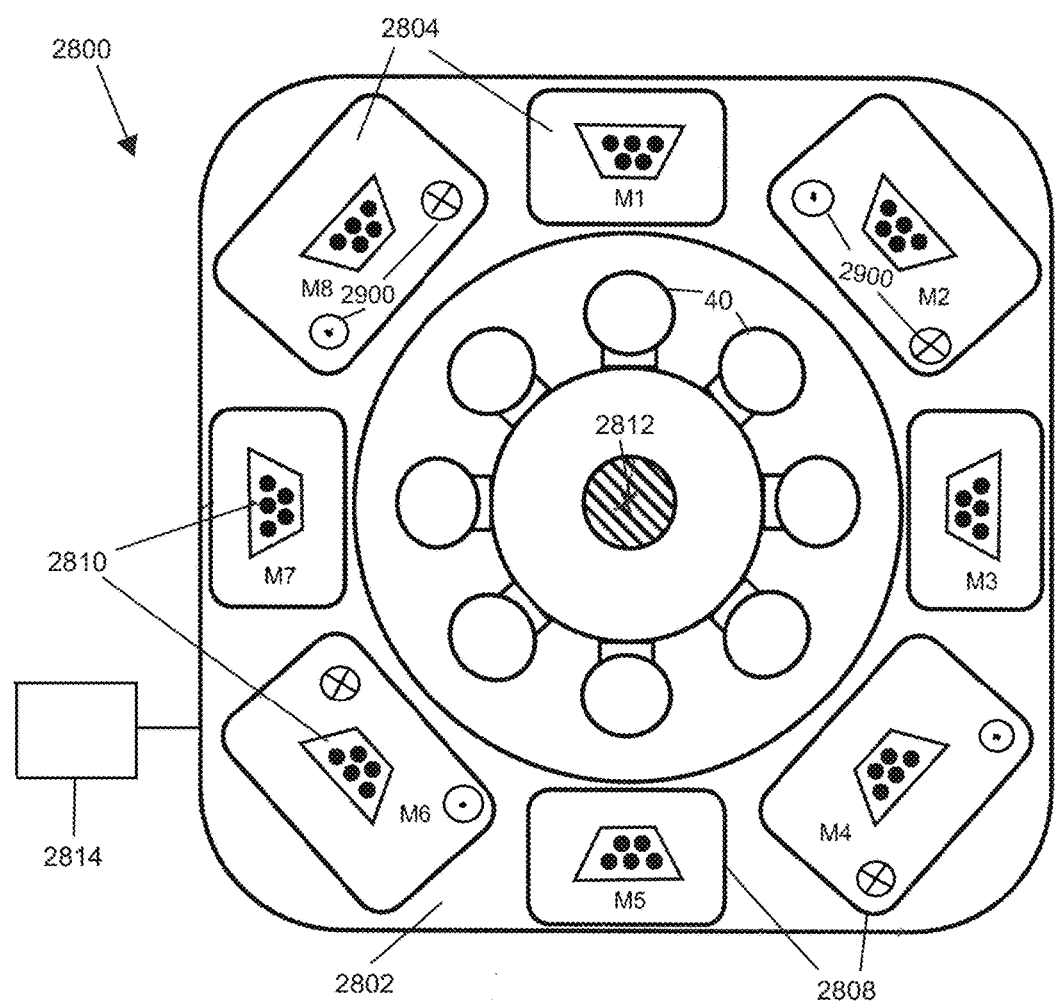
FIG. 29 is a schematic plan view of a sample processing arrangement according to another exemplary embodiment.

A sample processing arrangement 2800 according to another exemplary embodiment of the invention shown in FIG. 29 particularly differs from the sample processing arrangement 2800 shown in FIG. 28 in that the plug-in positions 2804 in FIG. 29 additionally comprise fluidic interfaces 2900. More precisely, each of the plug-in positions 2804 is provided with a fluid supply interface for supplying fluid to the sample processing module 2806 when being plugged in the corresponding plug-in position 2804, and another of the fluidic interfaces 2900 is provided for draining fluid from the attached sample processing module 2806 towards a waste container (not shown).

Figure 30:
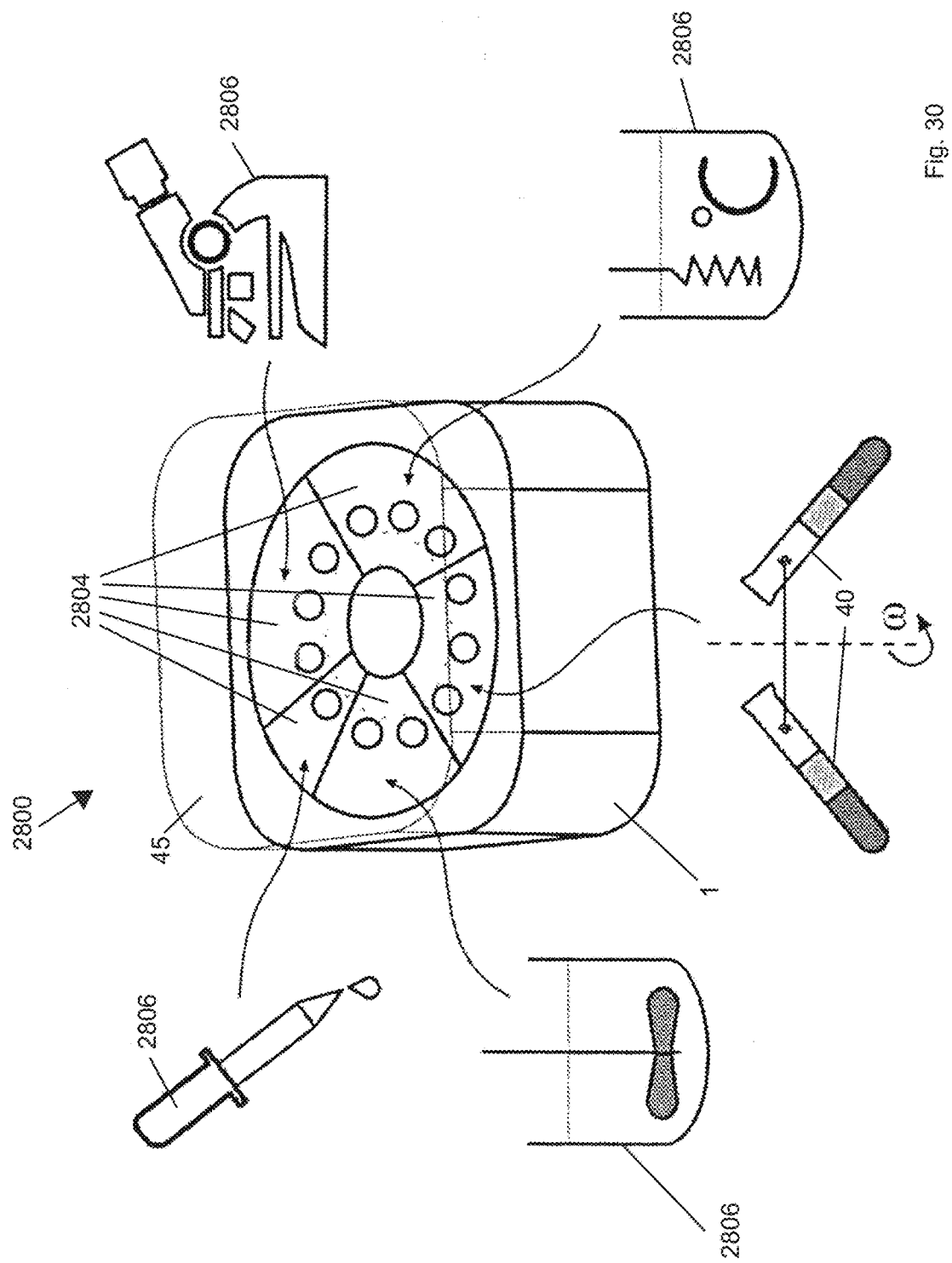
FIG. 30 is a three-dimensional view of a sample processing arrangement according to an exemplary embodiment of the invention having all sample processing tasks integrated within a casing formed by a stationary housing and a cover lid.

FIG. 30 shows a sample processing arrangement 2800 according to yet another exemplary embodiment of the invention. Particularly, a pipetting unit, a stirring unit, a microscope unit, and a tempering unit are provided as examples for sample processing modules 2806 plugged in the respective plug-in positions 2804 of the sample processing arrangement 2800. As can be furthermore taken from FIG. 30, all components described referring to FIGS. 28 and 29 (except the sample handling robot 2816) are mounted within a two-part casing constituted by a stationary support body 1 and a lid 45 covering the support body 1. Thus, the interior volume delimited by the stationary support body 1 and the lid 45 is hermetically sealed with regard to an environment. Therefore, particularly during centrifugation and mixing, the sample containers 40, which may move with a frantic speed, are kinetically decoupled from the environment of the sample processing arrangement 2800, therefore providing a high degree of operation safety. Particularly, the entire mounting platform 2802, the entire plug-in positions 2804 and the entire mounted sample processing modules 2806 may all be located between the stationary support body 1 and the lid 45.

Figure 31:
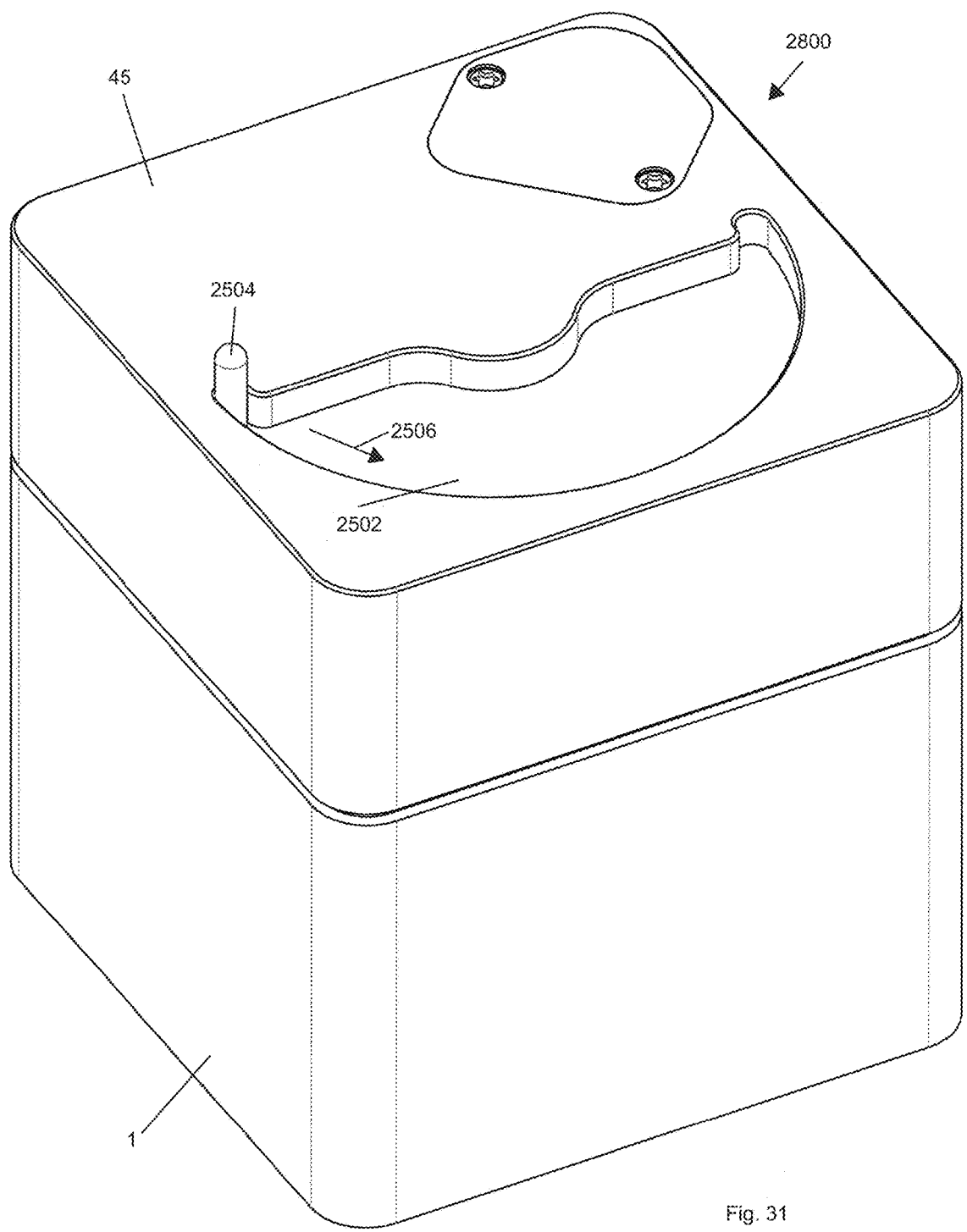
FIG. 31 shows a sample processing arrangement according to an exemplary embodiment of the invention with a cover lid which has an access recess being shown in a state in which it is closed by a movable cover plate.

As can be taken from FIG. 31, the lid 45 covering the support body 1 may completely separate an interior of the sample processing arrangement 2800 against an environment. In the operation mode shown in FIG. 31, a slidable cover plate 2502 completely covers a recess in an upper surface of the lid 45 to therefore disable access to an interior volume delimited by the lid 45 and the support body 1.

Figure 32:
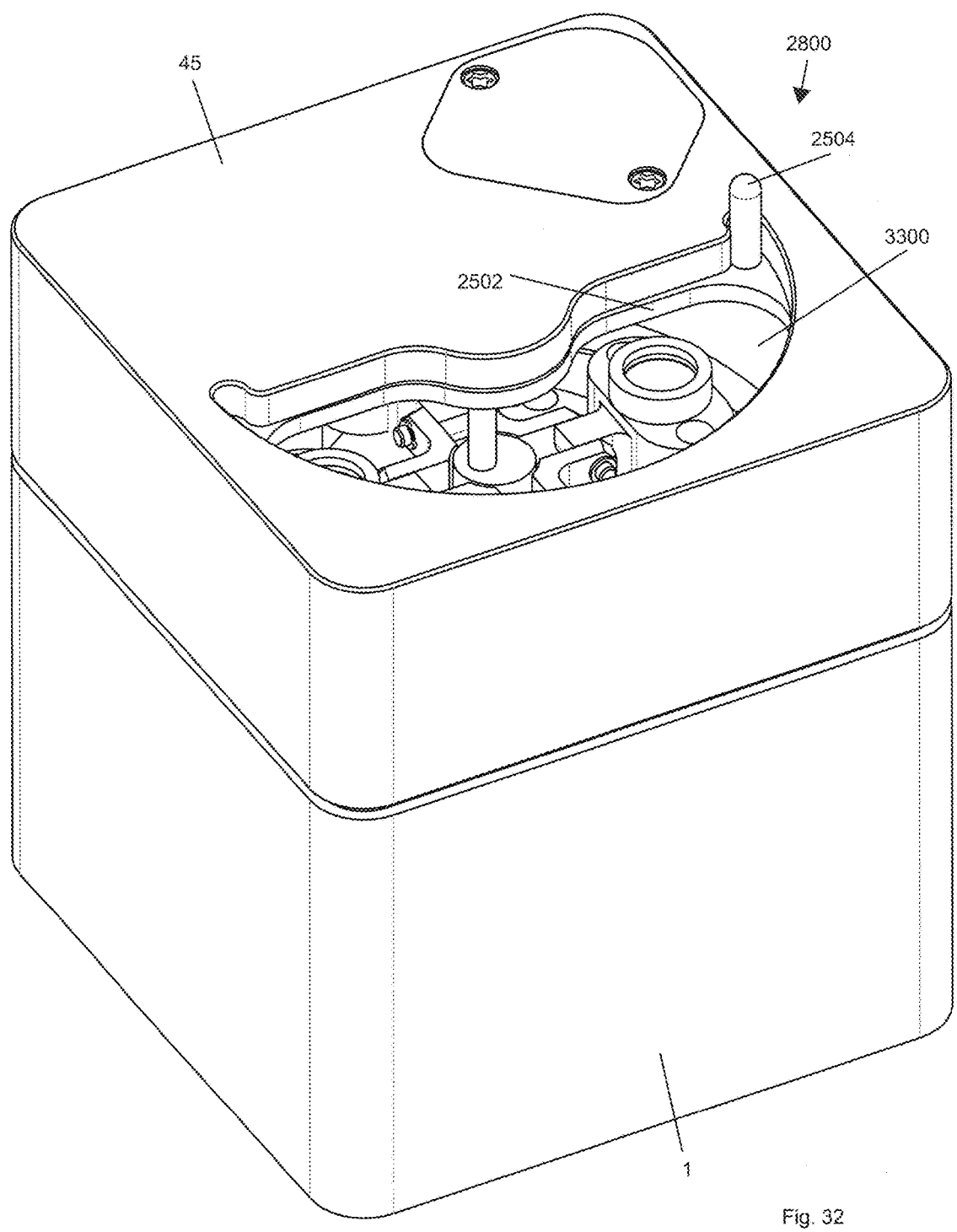
FIG. 32 shows the sample processing arrangement of FIG. 31 in an operation mode in which the recess of the lid is opened to enable access to sample containers in an interior of the outer casing of the sample processing arrangement.

An actuation pin 2504 can be gripped and actuated manually by a user so as to slide plate 2502 along a rotation trajectory 2506. When an end stop of the actuation pin 2504 is reached, the plate 2502 has been completely removed from the recess 3300 so that an interior of the sample processing arrangement 2800 is now accessible. The latter described state is illustrated in FIG. 32.

Figure 33:
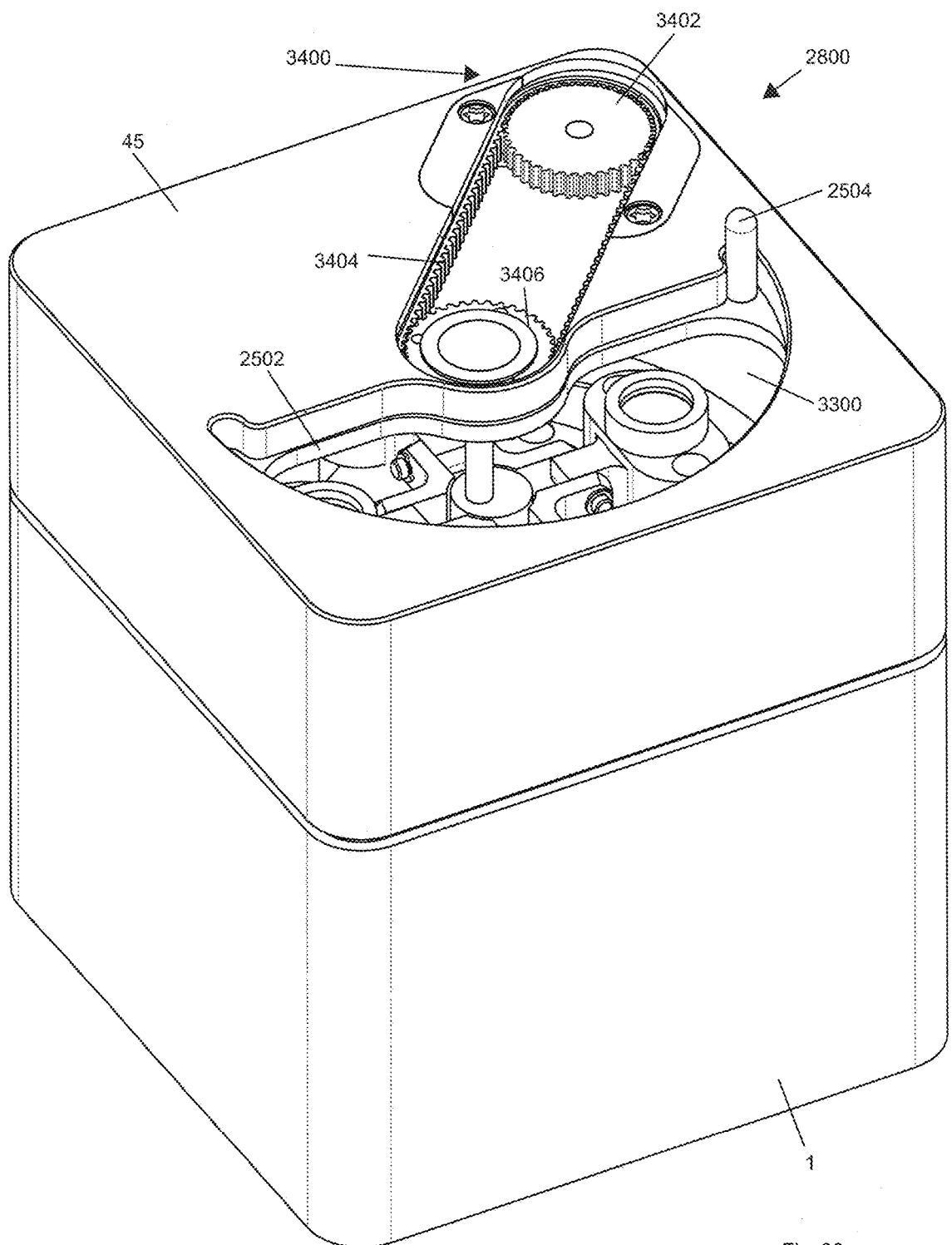
FIG. 33 illustrates a sample processing arrangement similar to FIG. 32 but additionally showing a belt drive mechanism for operating and moving the cover plate by a motor for selectively covering the recess of the lid or exposing an interior of the sample processing arrangement below the recess by sliding the cover plate away from the recess.
Figure 34:
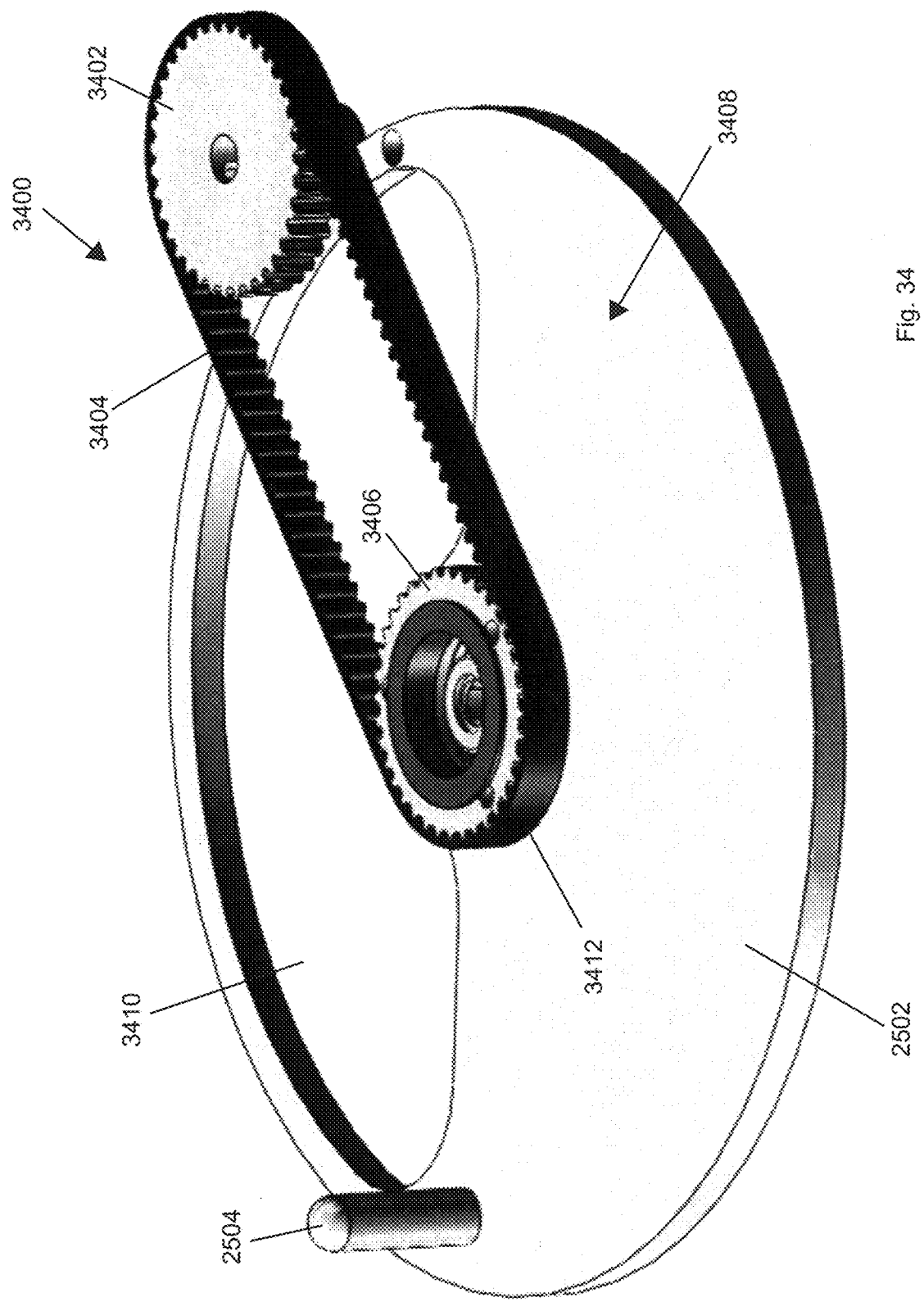
FIG. 34 and FIG. 35 show details of the belt drive mechanism of FIG. 33 for selectively covering or uncovering the lid.
Figure 35:
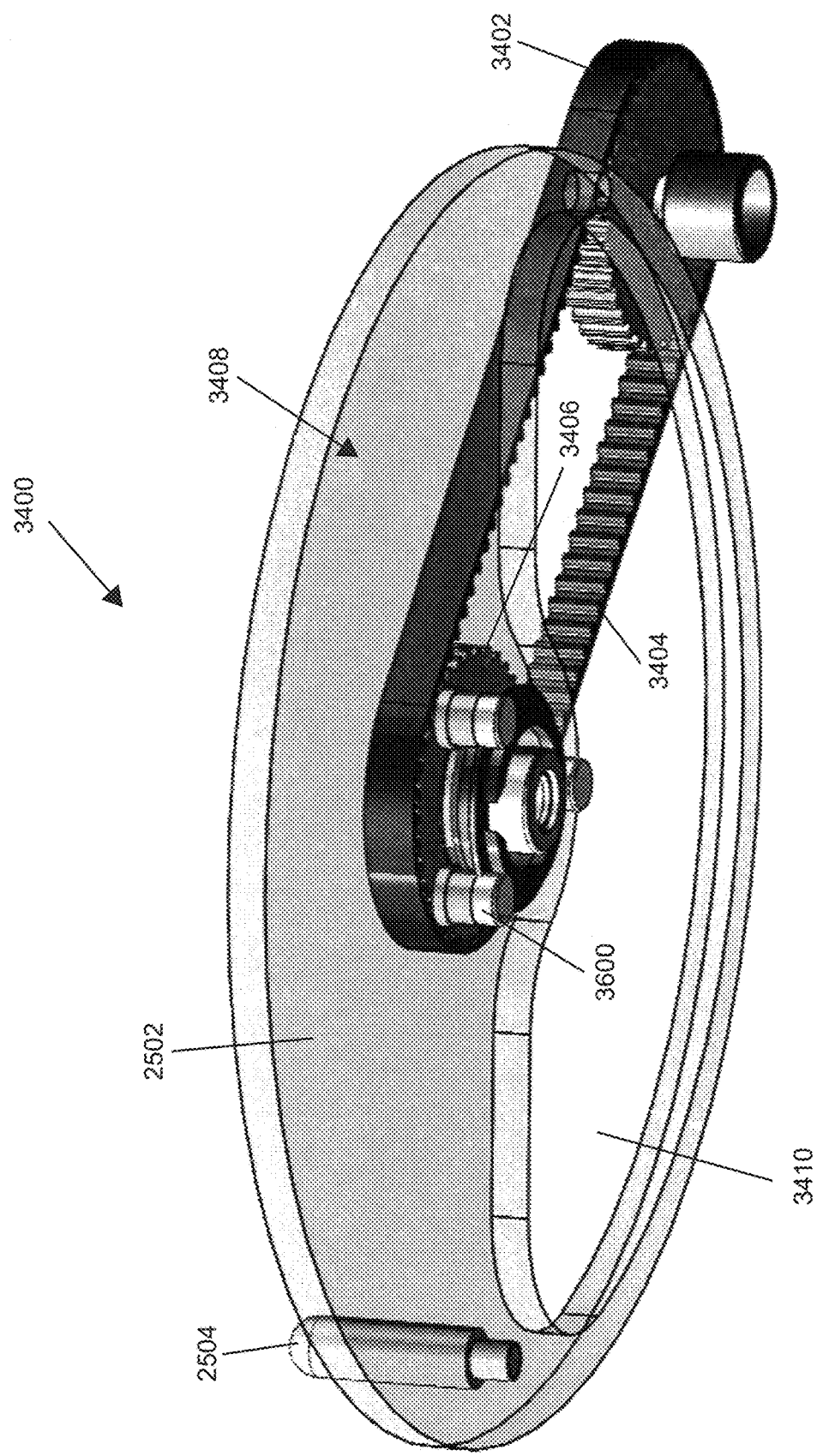

FIG. 33 shows a belt drive mechanism 3400 configured for automatically actuating the cover plate 2502 to automatically convert the sample processing arrangement 2800 between an open lid state (corresponding to FIG. 32 and FIG. 33) and a closed lid state (corresponding to FIG. 31). FIG. 34 and FIG. 35 show details of the belt drive mechanism 3400.

FIG. 33 shows a motor driven lid motion mechanism. A corresponding drive motor may apply torque via a belt gear mechanism having a belt pulley 3402, a belt 3404 and a further belt pulley 3406. By this force coupling mechanism, the force is transmitted in a synchronized way to slidable or rotatable plate member 3408 being constituted by the plate 2502 and a recessed portion 3410. The plate member 3408 and the belt pulley 3402 are connected to one another to enable force coupling therebetween. More specifically, the plate member 3408 is coupled via asymmetrically mounted spring-like elements 3600 with asymmetrically arranged bores 3412 of the belt pulley 3406. These components form a gliding coupling which separates, in case of an overload, belt pulley 3406 from plate member 3400. By means of this kind of sliding coupling it becomes possible to either open or close the lid 45 manually or automatically. Furthermore, this gliding coupling prevents injury of a user when the lid 45 is erroneously closed.

By the asymmetric bores 3412, the belt pulley 3406 and the plate member 3408 are coupled to one another only in one defined mutual position so that in case of an automatic motion of the plate member 3408 following a manual motion the appropriate end positions are reached rapidly.

An integrated Hall sensor (or any other appropriate sensor for position detection) may continuously detect whether the lid 45 is opened or is closed. Also this guarantees safety for a user and juxtaposed other apparatuses.

Figure 37:
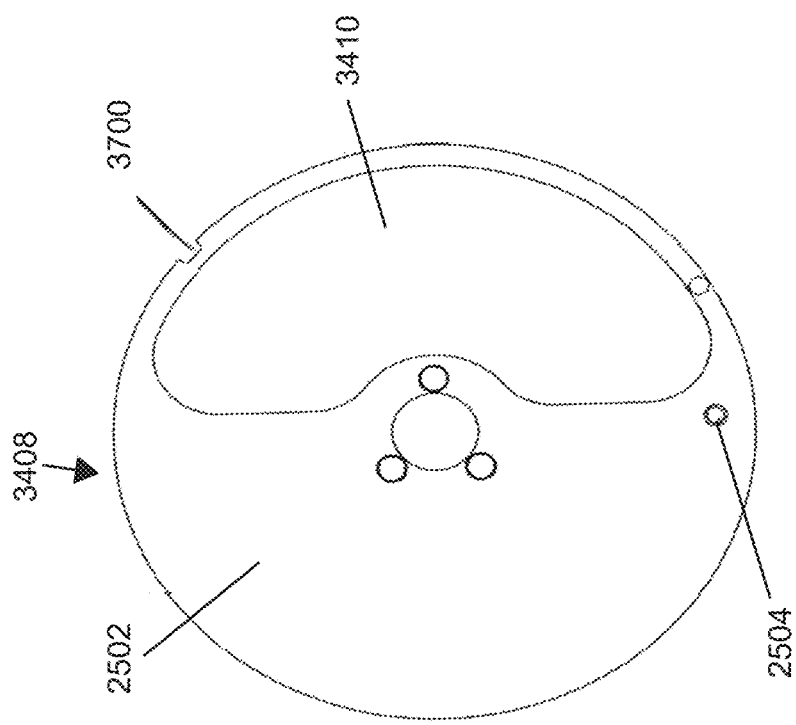
FIG. 36 shows a plan view of a lid and FIG. 37 shows a slidable cover plate cooperating with the lid of FIG. 36 for selectively covering or uncovering a through hole in the lid, wherein the lid has implemented a latch mechanism for selectively disabling exposure of an interior of a sample processing arrangement according to an exemplary embodiment by locking the cover plate to the lid in an active operation mode of the sample processing arrangement.
Figure 36:
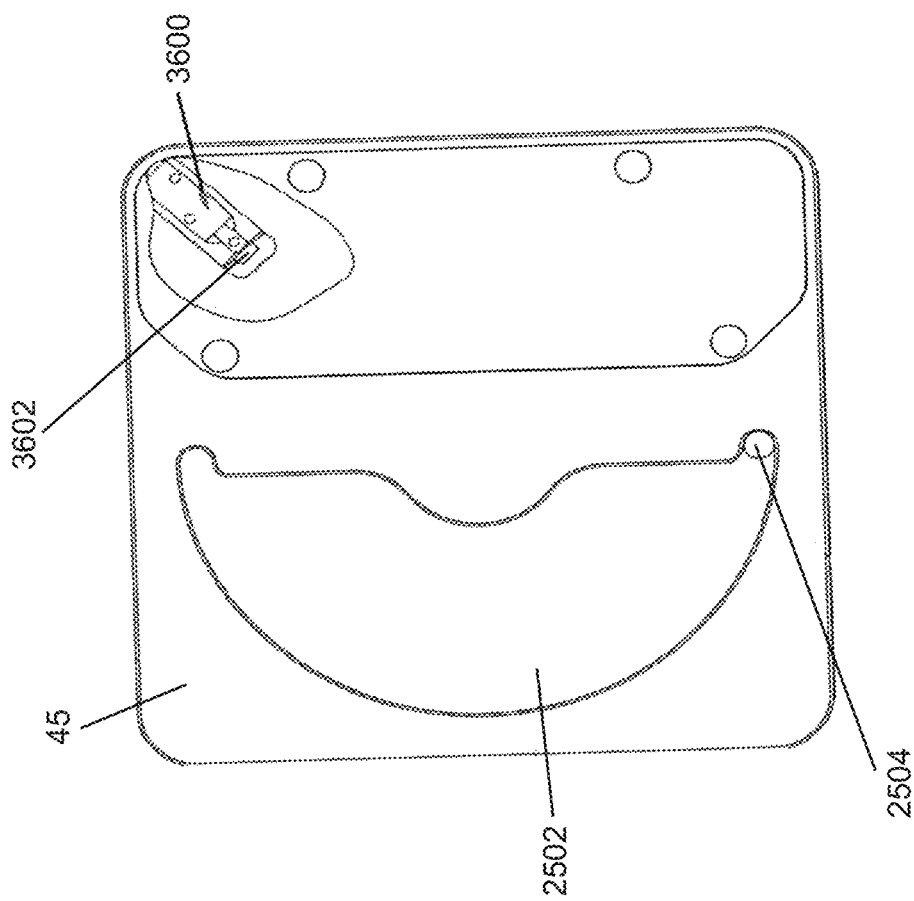

FIG. 36 shows a lid 45. FIG. 37 shows a slidable cover plate 2502 cooperating with the lid 45 for selectively covering or uncovering a recessed portion of the lid 45. The lid 45 has a latch mechanism for selectively disabling exposure of an interior of the corresponding sample processing arrangement by locking the cover plate 2502 to the lid 45 in an active operation mode of the sample processing arrangement (i.e. when a centrifugation or mixing of the sample(s) is performed).

For this purpose, the lid 45 is provided with an actuator 3600 in form of a lifting solenoid configured for moving forwardly or backwardly to thereby actuate a movably mounted latch 3602. The latch 3602 may be moved inside an indentation 3700 or outside the indentation 3700 of the cover plate 2502. Hence, it is possible to selectively lock the latch 3602 within the indentation 3700 in the slidable plate 2502 so that the latch 3602 locks the plate 2502 to the lid 45. In order to allow a user access to an interior of the sample processing arrangement as a result of a sliding operation of the slidable plate 2502, it is possible to selectively unlock the latch 3602 by retracting the latch 3602 from the indentation 3700.

Figure 38:
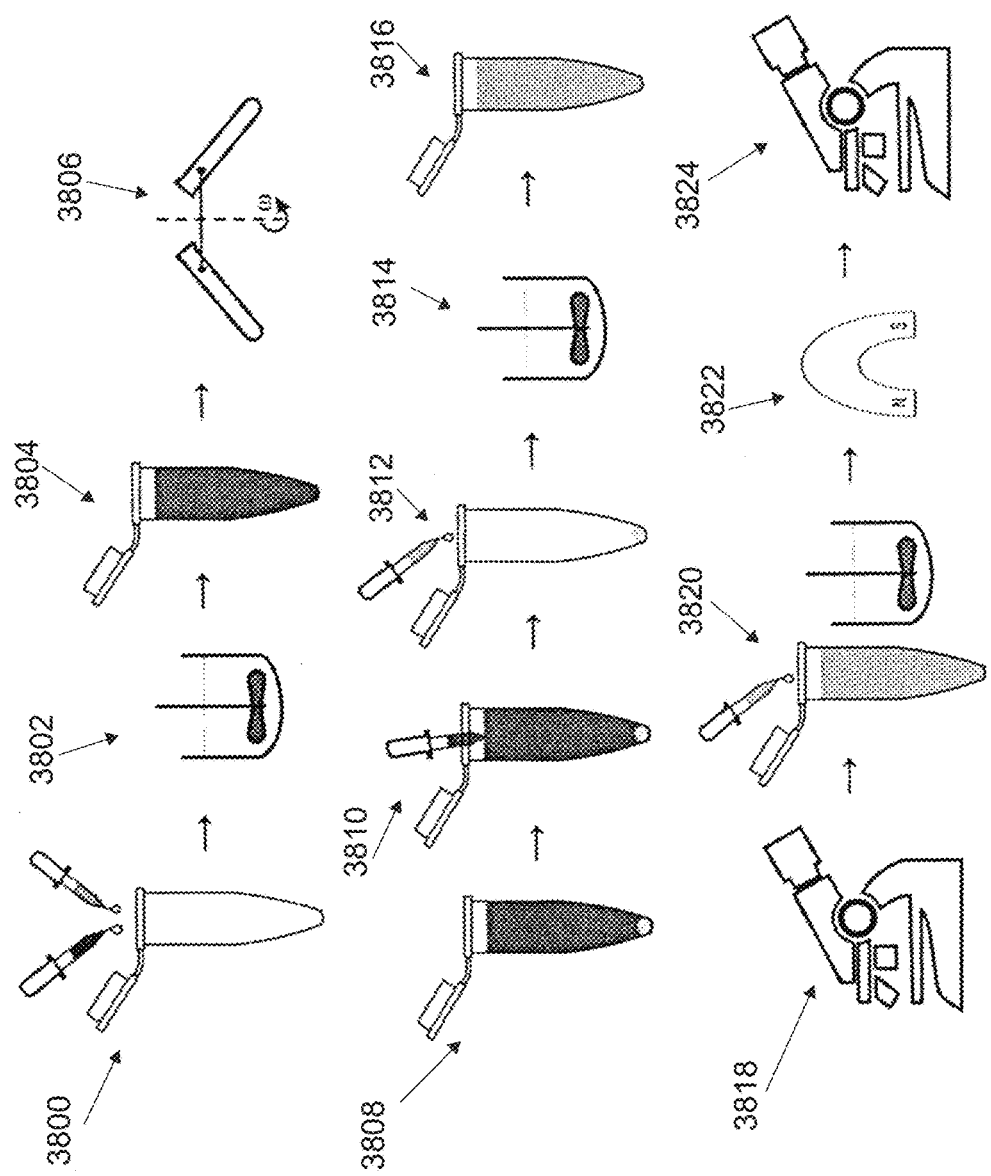
FIG. 38 illustrates individual procedures of a complex process to be carried out by a sample processing arrangement according to an exemplary embodiment by correspondingly equipping module accommodation positions by appropriately configured sample processing modules.

FIG. 38 illustrates individual procedures of a complex process to be carried out by a sample processing arrangement 2800 according to an exemplary embodiment by correspondingly equipping module accommodation positions 2804 by appropriately configured sample processing modules 2806.

Each of the procedures described in the following can be carried out by a respective one of multiple sample processing modules 2806. Each of these sample processing modules 2806 has to be placed at an appropriately located module accommodation position 2804, compare for instance FIG. 28.

In a procedure 3800, a blood and lysis buffer solution is prepared. For this purpose, a blood sample and a lysis buffer are inserted into a sample holder. In a subsequent procedure 3802, mixing is performed while blood cell lysis takes place. In a subsequent procedure 3804, a lysed sample in a sample container is obtained. In a subsequent procedure 3806, a centrifugation task is performed. The lysed blood sample is centrifuged, and a cell pellet (for instance leucocyte) may be generated during the centrifugation. Hence, as can be taken from reference numeral 3808, a cell pellet is formed. In a subsequent procedure 3810, supernatant is removed. The supernatant may be guided into a waste container. In a subsequent procedure 3812, a wash buffer is added. In a subsequent procedure 3814, resuspension by mixing is performed. In other words, the cell pellet is dissolved in the wash buffer by mixing. In a subsequent procedure 3816, the prepared sample is obtained. In a subsequent procedure 3818, a first cell counting procedure is carried out, i.e. the number of cells is estimated. In a subsequent procedure 3820, an incubation with magnetic nanoparticles is performed, and the solution is mixed. The magnetic particles may serve as markers. In a subsequent procedure 3822, a magnetic separation is carried out. Magnetic separation of those cells is performed which have accommodated the marker. In a subsequent procedure 3824, a second cell counting procedure is carried out. The number of marked/separated cells is estimated here.

FIG. 39 is a schematic plan view of a sample processing arrangement 2800 according to an exemplary embodiment of the invention in which all twelve module accommodation positions 2804 of identical dimension are presently not occupied by sample processing modules.

FIG. 40 is another view of the sample processing arrangement 2800 of FIG. 39 in an operation mode in which six module accommodation positions 2804 are presently not occupied by sample processing modules, one module accommodation position 2804 is presently occupied by one sample processing module 2806 (denoted as M1), two module accommodation positions 2804 are presently occupied by another sample processing module 2806 (denoted as M2), and three further module accommodation positions 2804 are presently occupied by still another sample processing module 2806 (denoted as M3).

FIG. 41 illustrates the sample processing modules 2806 according to FIG. 40, denoted as M1, M2 and M3.

Hence, FIG. 39 to FIG. 41 show that it is also possible in an embodiment of the invention to place a single sample processing module 2806 onto multiple module accommodation positions 2804. Thus, it is possible in an embodiment that one sample processing module 2806 occupies more than one module accommodation position 2804. Such an embodiment is advantageous when a certain complex module requires more space, more communication channels, more fluid channels and/or a higher electric power than provided by a single module accommodation position 2804.

It should be noted that the term "comprising" does not exclude other elements or features and the "a" or "an" does not exclude a plurality. Also elements described in association with different embodiments may be combined.

It should also be noted that reference signs in the claims shall not be construed as limiting the scope of the claims.

The invention claimed is:

1. A sample processing arrangement for processing a fluidic sample, the sample processing arrangement comprising:
   a sample holder for accommodating the fluidic sample;
   an apparatus having a rotor mechanism having a rotor axis and being configured for selectively operating the sample holder in an orbital motion mode for sample mixing or in a rotary motion mode for sample separation;
   wherein the orbital motion of the sample holder defines a motion along a trajectory which is obtained when being rotated with a first angular frequency around a first central rotation axis with a superposed additional rotation with a second angular frequency around a second rotation axis, which is parallel to the first rotation axis;
   a mounting platform having a central portion on which the apparatus and the sample holder are mounted and having a surrounding portion circumferentially surrounding the central portion; and
   a plurality of module accommodation positions circumferentially distributed in the surrounding portion to surround the rotor mechanism and the sample holder, the respective centers of the plurality of module accommodation positions being circularly and concentrically distributed and arranged around a circumferential surrounding of the rotor axis of the rotor mechanism;
   wherein each of the module accommodation positions is configured for detachably accommodating a selectable one of a plurality of sample processing modules, each being configured for fulfilling an assigned sample processing task, by accommodating the respective sample processing module in the respective one of the module accommodation positions.

2. The sample processing arrangement of claim 1, wherein at least a part of the plurality of module accommodation positions has a mechanical interface configured for accommodating the respective sample processing module by a form closure and/or by a force closure.

3. The sample processing arrangement of claim 1, wherein at least a part of the plurality of module accommodation positions has an electrical interface configured for supplying electric energy and/or configured for an electrical data exchange with the respective sample processing module when being accommodated in the respective module accommodation position.

4. The sample processing arrangement) of claim 1, wherein at least a part of the plurality of module accommodation positions has a fluidic interface configured for an exchange of a fluid with the respective sample processing module when being accommodated in the respective module accommodation position.

5. The sample processing arrangement of claim 2, wherein the respective interface between the respective module accommodation position and the respective sample processing module is activated by accommodating the respective sample processing module in the respective module accommodation position.

6. The sample processing arrangement of claim 1, wherein the fluidic sample, when accommodated in the sample holder, is arranged between the plurality of module accommodation positions and the rotor axis.

7. The sample processing arrangement of claim 1, wherein at least two of the plurality of module accommodation positions are configured for accommodating the same sample processing module.

8. The sample processing arrangement of claim 1, wherein the plurality of module accommodation positions is grouped into multiple groups of module accommodation positions, each group being configured for accommodating only an assigned group of same sample processing modules.

9. The sample processing arrangement of claim 1, wherein the sample holder comprises a plurality of sample containers each configured for accommodating a respective fluidic sample and each configured for being rotatable around a common rotor axis of the rotor mechanism.

10. The sample processing arrangement of claim 9, wherein the apparatus is configured for selectively operating the sample holder in a module alignment mode in which the rotor mechanism is operated to move a predefined one of the plurality of sample containers in alignment with a predefined one of the plurality of module accommodation positions so as to align the predefined sample container with a sample processing module in the predefined module accommodation position for subsequently executing the assigned sample processing task.

11. The sample processing arrangement of claim 10, comprising a control unit configured for operating the apparatus in the rotary motion mode, the orbital motion mode and the module alignment mode and for operating at least one sample processing module accommodated in an assigned module accommodation position for executing the assigned sample processing task so as to perform a fluidic sample processing in accordance with a predefined processing protocol.

12. The sample processing arrangement of claim 1, comprising the plurality of sample processing modules each being configured for being accommodated in one or more of the plurality of module accommodation positions.

13. The sample processing arrangement of claim 12, wherein at least one of the plurality of sample processing modules is configured for being accommodated in at least two of the plurality of module accommodation positions at the same time.

14. The sample processing arrangement of claim 12, wherein the plurality of sample processing modules comprise at least one of the group consisting of a temperature adjustment module configured for adjusting a temperature of the fluidic sample, a metering module configured for metering substance to be inserted into the sample holder, a collection module configured for collecting at least a part the fluidic sample from the sample holder, a sensing module configured for sensing at least one parameter of the fluidic sample in the sample holder, an analysis module configured for analyzing the fluidic sample in the sample holder, a magnetic separation module configured for magnetically separating the fluidic sample in the sample holder, a waste module configured for removing a waste substance from the fluidic sample in the sample holder, and a storage module configured for storing at least one substance.

15. The sample processing arrangement of claim 1, comprising a sample and/or sample container handling unit configured for handling fluidic sample with regard to the sample holder and/or configured for handling one or more sample containers of the sample holder.

16. The sample processing arrangement of claim 15, wherein the sample and/or sample container handling unit comprises at least one of the group consisting of a sample supply robot, a sample container handling robot, a pipetting system and a metering pump.

17. The sample processing arrangement of claim 15, wherein the sample and/or sample container handling unit forms at least one of the plurality of sample processing modules.

18. The sample processing arrangement of claim 1, wherein the apparatus has a support body being stationarily mounted in the central portion of the mounting platform and has an accessible lid covering the sample holder in a closed state and exposing the sample holder with regard to an environment in an open state.

19. The sample processing arrangement of claim 18, wherein the lid has a recess in a top surface thereof which is selectively closable or openable by moving a slidable plate so that the plate covers the recess in lid in a closed state and exposes the recess in lid in an opened state.

20. The sample processing arrangement of claim 19, wherein the plate comprises an actuation pin being operable along a rotation trajectory for sliding the plate below an upper surface of the lid for exposing an interior of the apparatus to an external environment and for sliding the plate to cover the recess of the lid for closing the apparatus.

21. The sample processing arrangement of claim 18, comprising a lid actuation unit configured for actuating the lid to bring the lid selectively in the closed state or in the open state.

22. The sample processing arrangement of claim 21, wherein the lid actuation unit is a belt drive mechanism.

23. The sample processing arrangement of claim 18, wherein the sample holder, the rotor mechanism, the mounting platform and the plurality of module accommodation positions are arranged within a volume delimited by the support body and the lid.

24. The sample processing arrangement of claim 19, wherein the lid has an actuator configured for actuating a movably mounted latch so as selectively lock the latch within an indentation in the slidable plate so that the latch locks the plate to the lid in a closed state of the recess in the top surface of the lid.

25. The sample processing arrangement of claim 1, wherein the apparatus comprises:
a gear element being drivable by a drive unit to rotate selectively in a first direction (A) or in a second direction (B) being inverse to the first direction (A);
an orbital motion generator configured for generating the orbital motion of the sample holder when being operated in the orbital motion mode;
a rotary motion generator configured for generating the rotary motion of the sample holder when being operated in the rotary motion mode;
a one-way clutch arrangement configured for selectively:
coupling the gear element with the orbital motion generator to transfer a driving force from the gear element to the orbital motion generator for generating the orbital motion when the gear element is driven in the first direction (A) and to freewheel when the gear element is driven in the second direction (B); or
coupling the gear element with the rotary motion generator to transfer a driving force from the gear element to the rotary motion generator for generating the rotary motion when the gear element is driven in the second direction (B) and to freewheel when the gear element is driven in the first direction (A).

26. The sample processing arrangement of claim 25, wherein the one-way clutch arrangement comprises:
a first one-way clutch configured for coupling the gear element with the orbital motion generator to transfer the driving force from the gear element to the orbital motion generator for generating the orbital motion when the gear element is driven in the first direction (A) and to freewheel when the gear element is driven in the second direction (B);
a second one-way clutch configured for coupling the gear element with the rotary motion generator to transfer the driving force from the gear element to the rotary motion generator for generating the rotary motion when the gear element is driven in the second direction (B) and to freewheel when the gear element is driven in the first direction (A).

27. The sample processing arrangement of claim 25, wherein the first one-way clutch and the second one-way clutch freewheel in mutually opposite directions and transmit force in mutually opposite directions.

28. The sample processing arrangement of claim 25, wherein the gear element is configured as a hollow shaft.

29. The sample processing arrangement of claim 28, wherein the first one-way clutch is arranged between an interior curved surface of the hollow shaft and an exterior curved surface of a drive shaft of the orbital motion generator.

30. The sample processing arrangement of claim 28, wherein the second one-way clutch is arranged between an exterior curved surface of the hollow shaft and an interior curved surface of a movably mounted cogwheel of the rotary motion generator.

31. The sample processing arrangement of claim 25, wherein the rotary motion generator comprises:
a selectively lockable first cogwheel in an unlocked movably mounted state, coupled to the gear element via the one-way clutch arrangement and having a plurality of first cogs arranged along an outer circumference of the first cogwheel;
a movably mounted second cogwheel having a plurality of second cogs arranged along an outer circumference of the second cogwheel;
a coupling body having a plurality of third cogs arranged along an inner circumference of the coupling body;
wherein the coupling body is mounted with the first cogwheel and with the second cogwheel to engage part of the first cogs and part of the second cogs by part of the third cogs to thereby generate the rotary motion of the second cogwheel and the sample holder to be mounted so as to follow a motion of the second cogwheel upon rotating the gear element in the second direction (B).

32. The sample processing arrangement of claim 31, wherein the orbital motion generator comprises:
the selectively lockable first cogwheel in a locked stationarily mounted state and having a first through hole;
the second cogwheel having a second through hole;
a drive shaft coupled to the gear element via the one-way clutch arrangement and having a concentric first section and an eccentric second section, wherein the first section is guided through the first through hole and the second section is guided through the second through hole;
wherein the coupling body is mounted with the first cogwheel and with the second cogwheel to engage part of the first cogs and part of the second cogs by part of the third cogs to thereby generate the orbital motion of the second cogwheel and the sample holder to be mounted so as to follow a motion of the second cogwheel upon rotating the gear element in the first direction (A).

33. The sample processing arrangement of claim 31, further comprising a cogwheel locking element configured for selectively locking the first cogwheel in the locked stationarily mounted state or for unlocking the first cogwheel in the unlocked movably mounted state.

34. The sample processing arrangement of claim 31, further comprising a shaft locking element configured for selectively locking the drive shaft in a locked stationarily mounted state, particularly in the rotary motion mode, or for unlocking the drive shaft in an unlocked movably mounted state, particularly in the orbital motion mode.

35. The sample processing arrangement of claim 31, wherein each of the first cogwheel and the second cogwheel is a toothed belt disc and the coupling body is a toothed belt.

36. The sample processing arrangement of claim 31, wherein the coupling body is a flexible structure being deformable but non-elongatable upon rotating the drive shaft so as to adapt its shape to follow motion of the second cogwheel while maintaining the coupling between the first cogwheel and the second cogwheel.

37. The sample processing arrangement of claim 25, comprising a drive unit being configured for rotating, the gear element.

38. The sample processing arrangement of claim 25, further comprising a locking one-way clutch configured for coupling a drive shaft of the orbital motion generator with a stationary housing so as to selectively lock the drive shaft with the stationary housing to a locked stationarily mounted state when the gear element is driven in one direction (B), or to freewheel in an unlocked movably mounted state of the drive shaft when the gear element is driven in another direction (A).

39. The sample processing arrangement of claim 38, wherein the stationary housing comprises a lid detachably connectable to and/or pivotably mounted on a spatially fixed support body of the stationary housing, wherein the locking one-way clutch is configured for coupling the drive shaft with the lid.

40. The sample processing arrangement of claim 38, wherein the one direction equals to the second direction (B) and the other direction equals to the first direction (A).

41. A method of configuring a sample processing arrangement for processing a fluidic sample in accordance with a user selection, the method comprising:
accommodating the fluidic sample in a sample holder;
selectively operating the sample holder accommodating the fluidic sample in an orbital motion mode for sample mixing or in a rotary motion mode for sample separation using an apparatus having a rotor mechanism with a rotor axis and being mounted, together with the sample holder, on a central portion of a mounting platform,
wherein the orbital motion of the sample holder defines a motion along a trajectory which is obtained when being rotated with a first angular frequency around a first central rotation axis with a superposed additional rotation with a second angular frequency around a second rotation axis, which is parallel to the first rotation axis; and
detachably accommodating selected ones of a plurality of sample processing modules, each being configured for fulfilling an assigned sample processing task, in a plurality of module accommodation positions being circumferentially distributed in a surrounding portion of the mounting platform circumferentially surrounding the central portion to surround the rotor mechanism and the sample holder;
wherein respective centers of the plurality of module accommodation positions are circularly and concentrically distributed and arranged around a circumferential surrounding of the rotor axis of the rotor mechanism;
processing the fluidic sample by the sample processing modules being accommodated in the module accommodation positions.

42. The method of claim 41, wherein the method further comprises rearranging at least a part of the plurality of sample processing modules over the plurality of module accommodation positions by detaching at least one of the accommodated sample processing modules from the respective module accommodation position and/or by accommodating another one of the plurality of sample processing modules in an unoccupied one of the plurality of module accommodation positions.

* * * * *